United States Patent [19]
Zaun et al.

[11] Patent Number: 6,068,978
[45] Date of Patent: *May 30, 2000

[54] APPARATUS AND METHOD FOR TRANSFER OF A FLUID SAMPLE

[75] Inventors: Peter Zaun, Libertyville; Stanley R. Bouma, Grayslake; Julian Gordon, Lake Bluff; John J. Kotlarik, Vernon Hills; Natalie A. Solomon, Buffalo Grove, all of Ill.

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/859,552

[22] Filed: May 20, 1997

Related U.S. Application Data

[63] Continuation of application No. 08/697,403, Aug. 23, 1996, abandoned, which is a continuation of application No. 08/495,124, Jun. 27, 1995, abandoned, which is a continuation of application No. 08/140,730, Oct. 21, 1993, abandoned.

[51] Int. Cl.[7] .................................................... C12Q 1/68
[52] U.S. Cl. .............. 435/6; 435/91.1; 435/91.2; 435/290; 435/808; 422/50; 422/61; 422/63; 422/68.1; 422/81; 422/99; 422/141; 422/145; 422/146; 422/149; 935/1; 935/16; 935/17
[58] Field of Search ............................ 435/6, 91.1, 91.2, 435/290, 808; 422/50, 61, 63, 68.1, 81, 99, 141, 145, 146, 149; 935/1, 16, 17

[56] References Cited

U.S. PATENT DOCUMENTS

| | | | |
|---|---|---|---|
| 4,116,631 | 9/1978 | Trinel et al. | 23/230 B |
| 5,160,413 | 11/1992 | Allison | 203/35 |
| 5,176,203 | 1/1993 | Larzul | . |
| 5,210,015 | 5/1993 | Gelfand et al. | . |
| 5,229,297 | 7/1993 | Schnipelsky et al. | 436/94 |

FOREIGN PATENT DOCUMENTS

| | | |
|---|---|---|
| 0 381 501 | 8/1990 | European Pat. Off. . |
| 0 504 435 | 10/1990 | European Pat. Off. ........... C12Q 1/68 |
| 0 469 441 A1 | 7/1991 | European Pat. Off. . |
| 0 504 435 A1 | 9/1992 | European Pat. Off. . |
| 2 672 301 | 1/1991 | France . |
| 2 238 005 | 5/1991 | United Kingdom . |
| WO 92/20778 | 11/1992 | WIPO . |

OTHER PUBLICATIONS

Higuchi, Russell, Simultaneous Amplification and Detection of Specific DNA Sequences, Bio/Technology, Research, vol. 10, Apr. 1991, pp. 413–417.

Higuchi, Russell, Kinetic PCR Analysis: Real–Time Monitoring of DNA Amplification Reactions, Bio/Technology, Research, vol. 11, Sep. 11, 1993, pp. 1026–1030.

*Primary Examiner*—Kenneth R. Horlick
*Assistant Examiner*—Janell E. Taylor
*Attorney, Agent, or Firm*—Paul D. Yasger

[57] ABSTRACT

Methods, devices, apparatus and kits for amplifying and detecting nucleic acid are provided. The apparatus is a one or two-tier thermal cycling device that operates in conjunction with a reaction/detection unit. A sample is loaded into a reaction chamber of the device which is then mated with a detection chamber to form the reaction/detection unit. A first heating element of the thermal cycling apparatus applies a desired temperature to the reaction/detection device to amplify target nucleic acid in the sample. The reaction mixture is then transferred to the detection chamber by the second heating element and amplified target nucleic acid is immobilized on a support in the detection chamber. Microprocessor control controls the heat applied by the second element independently of the heat applied by the first element. A detection system associated with the apparatus detects and analyzes the immobilized amplified nucleic acid target. Images are captured and digitized and subjected to statistical analysis to improve the accuracy of the method.

21 Claims, 26 Drawing Sheets

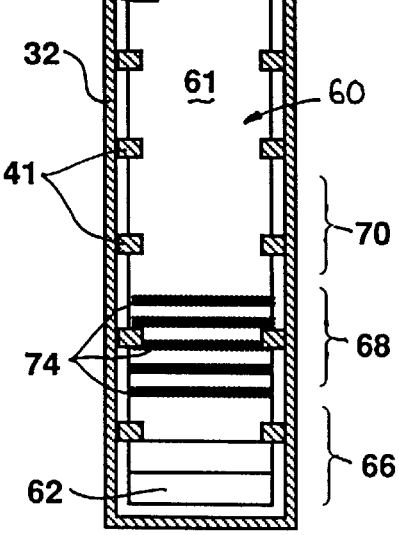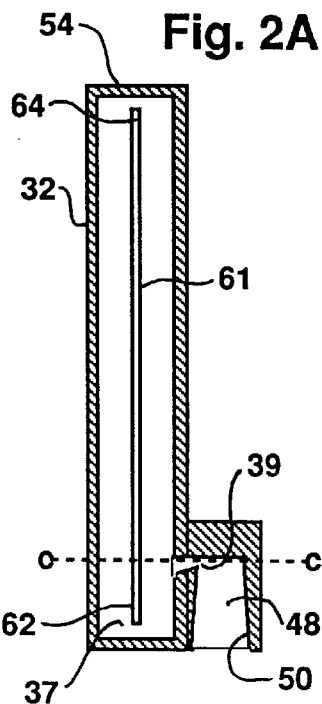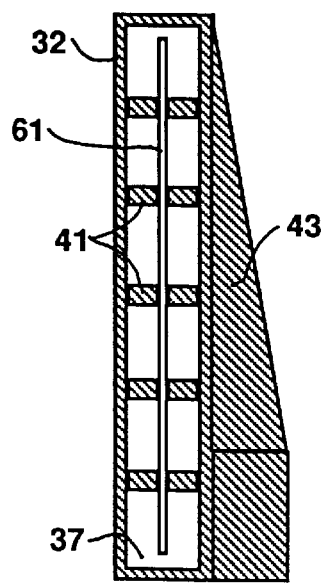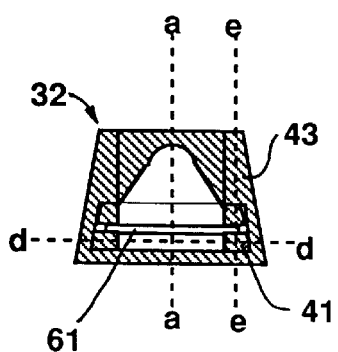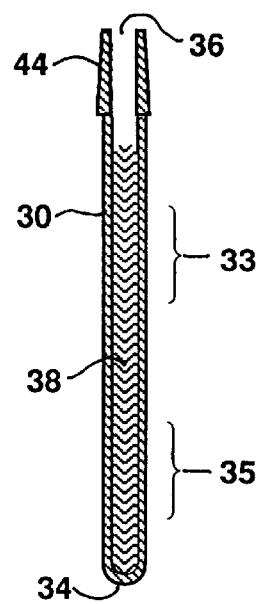
Fig. 2A  Fig. 2D  Fig. 2E  Fig. 2C  Fig. 2B

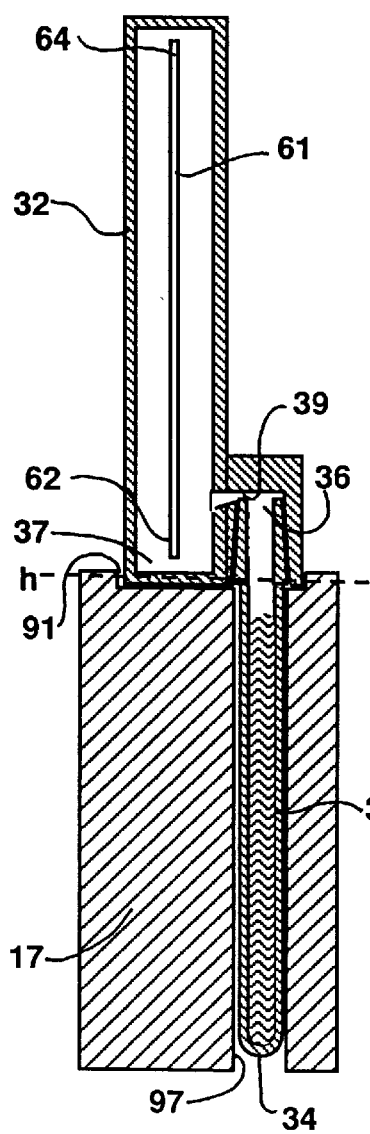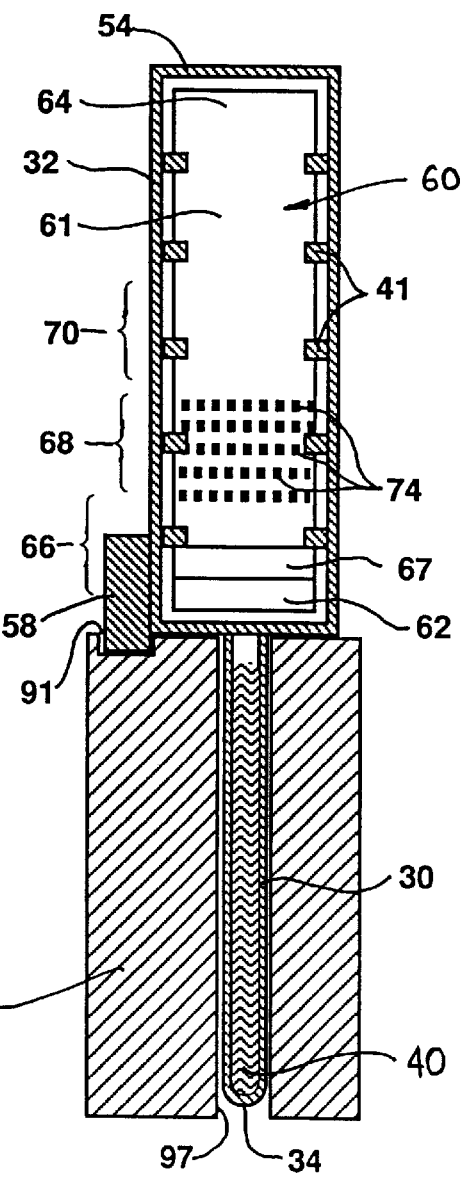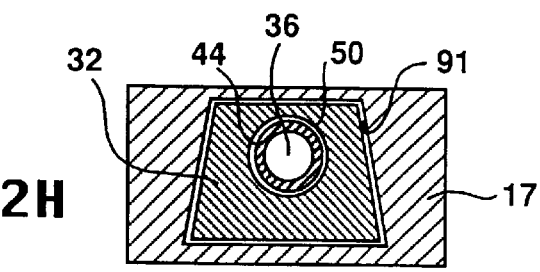

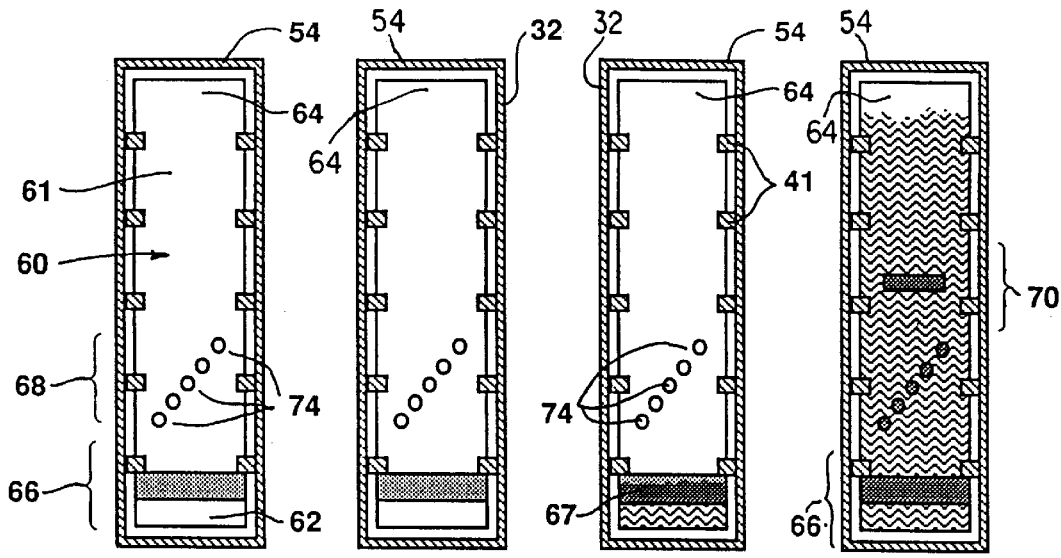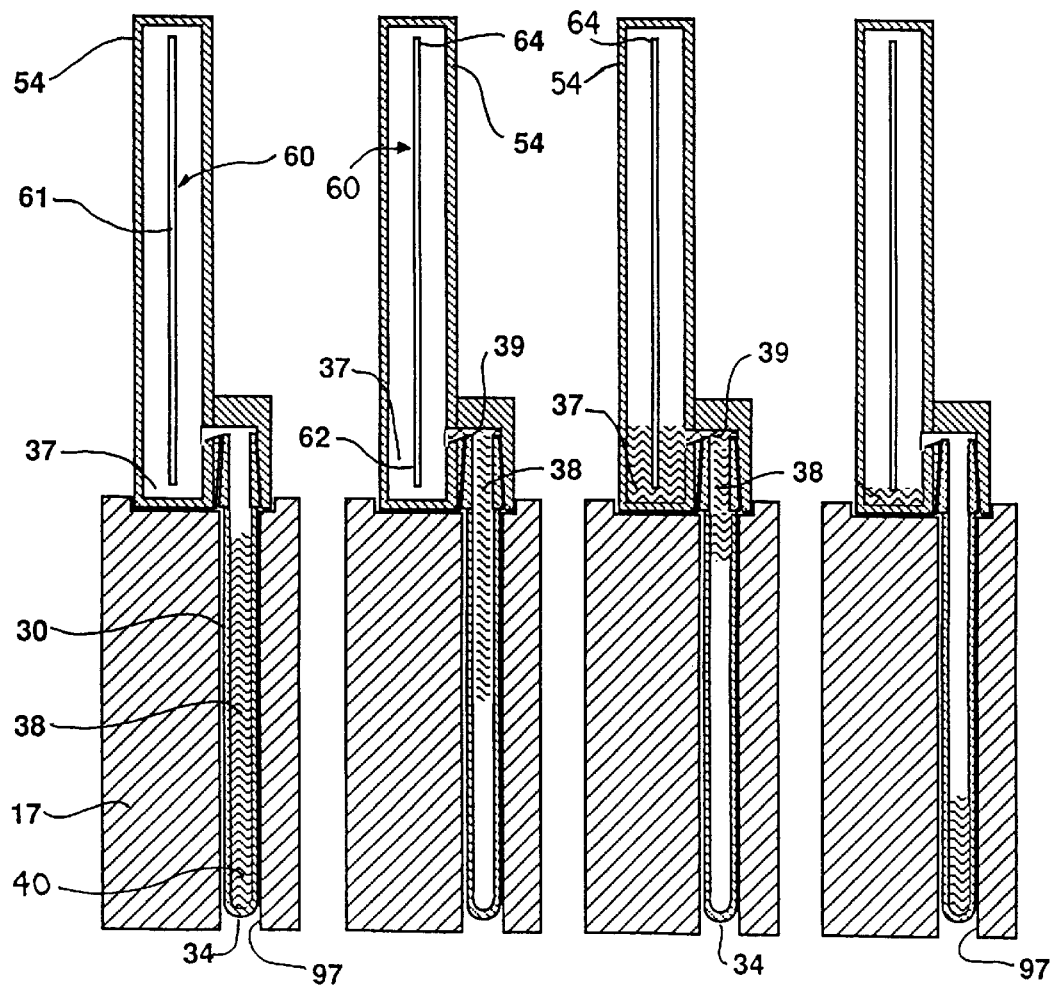

CYCLE/SUPER-HEAT - 208

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 19
      (B) TYPE: nucleic acid
      (C) STRANDEDNESS: single
      (D) TOPOLOGY: linear (ii) MOLECULE TYPE: Other nucleic acid (synthetic DNA)

(xi) SEQUENCE DESCRIPTION: SEQ ID NO: 1:

GTGTCAGGAC CAGCATTCC                                          19

(2) INFORMATION FOR SEQ ID NO: 2:

(i) SEQUENCE CHARACTERISTICS:
      (A) LENGTH: 20
      (B) TYPE: nucleic acid
      (C) STRANDEDNESS: single
      (D) TOPOLOGY: linear (ii) MOLECULE TYPE: Other nucleic acid (synthetic DNA)

(xi) SEQUENCE DESCRIPTION: SEQ ID NO: 2:

GTAAAGGGGA GCAATAAGGT                                       20

(2) INFORMATION FOR SEQ ID NO: 3:

(i) SEQUENCE CHARACTERISTICS:
      (A) LENGTH: 18
      (B) TYPE: nucleic acid
      (C) STRANDEDNESS: single
      (D) TOPOLOGY: linear (ii) MOLECULE TYPE: Other nucleic acid (synthetic DNA)

(xi) SEQUENCE DESCRIPTION: SEQ ID NO: 3:

GAATGCTGGT CCTGACAC                                            18

(2) INFORMATION FOR SEQ ID NO: 4:

(i) SEQUENCE CHARACTERISTICS:
      (A) LENGTH: 21
      (B) TYPE: nucleic acid
      (C) STRANDEDNESS: single
      (D) TOPOLOGY: linear (ii) MOLECULE TYPE: Other nucleic acid (synthetic DNA)

(xi) SEQUENCE DESCRIPTION: SEQ ID NO: 4:

ACCTTATTGC TCCCCTTTAC C                                                     21

(2) INFORMATION FOR SEQ ID NO: 5:

(i) SEQUENCE CHARACTERISTICS:
            (A) LENGTH: 50
            (B) TYPE: nucleic acid
            (C) STRANDEDNESS: double stranded
            (D) TOPOLOGY: linear (ii) MOLECULE TYPE: genomic DNA (xi) SEQUENCE DESCRIPTION: SEQ ID NO: 5:

ATATTGTTGT GTCAGGACCA GCATTCCGGG AAAGGGGAGC AATAAGGTCA                      50

(2) INFORMATION FOR SEQ ID NO: 6:

(i) SEQUENCE CHARACTERISTICS:
            (A) LENGTH: 18
            (B) TYPE: nucleic acid
            (C) STRANDEDNESS: single
            (D) TOPOLOGY: linear (ii) MOLECULE TYPE: Other nucleic acid (synthetic DNA)

(xi) SEQUENCE DESCRIPTION: SEQ ID NO: 6:

GGGCAAGGTG AACGTGGA                                                         18

(2) INFORMATION FOR SEQ ID NO: 7:

(i) SEQUENCE CHARACTERISTICS:
            (A) LENGTH: 18
            (B) TYPE: nucleic acid
            (C) STRANDEDNESS: single
            (D) TOPOLOGY: linear (ii) MOLECULE TYPE: Other nucleic acid (synthetic DNA)

(xi) SEQUENCE DESCRIPTION: SEQ ID NO: 7:

GAAGTTGGTG GTGAGGCC                                                         18

(2) INFORMATION FOR SEQ ID NO: 8:

(i) SEQUENCE CHARACTERISTICS:
            (A) LENGTH: 17
            (B) TYPE: nucleic acid
            (C) STRANDEDNESS: single
            (D) TOPOLOGY: linear (ii) MOLECULE TYPE: Other nucleic acid (synthetic DNA)

(xi) SEQUENCE DESCRIPTION: SEQ ID NO: 8:

CCACGTTCAC CTTGCCC                                                          17

(2) INFORMATION FOR SEQ ID NO: 9:

(i) SEQUENCE CHARACTERISTICS:
            (A) LENGTH: 19
            (B) TYPE: nucleic acid
            (C) STRANDEDNESS: single
            (D) TOPOLOGY: linear (ii) MOLECULE TYPE: Other nucleic acid (synthetic DNA)

(xi) SEQUENCE DESCRIPTION: SEQ ID NO: 9:

```
GGCCTCACCA CCAACTTCA                                                             19

(2) INFORMATION FOR SEQ ID NO: 10:

(i) SEQUENCE CHARACTERISTICS:
         (A) LENGTH:  47
         (B) TYPE:  nucleic acid
         (C) STRANDEDNESS:  double stranded
         (D) TOPOLOGY:  linear (ii) MOLECULE TYPE:  genomic DNA (xi) SEQUENCE DESCRIPTION: SEQ ID NO: 10:

CCTGTGGGGC AAGGTGAACG TGGATGAAGT TGGTGGTGAG GCCCTGG                               47
```

APPARATUS AND METHOD FOR TRANSFER OF A FLUID SAMPLE

This application is a continuation of U.S. patent application Ser. No. 08/697,403, filed Aug. 23, 1996, now abandoned, which is a continuation of Ser. No. 08/495,124, filed Jun. 27, 1995, now abandoned, which is a continuation of Ser. No. 08/140,730 filed Oct. 21, 1993, now abandoned.

FIELD OF THE INVENTION

The present invention relates generally to methods for fluid transfer, and in particular to a method for transferring amplified nucleic acid from a reaction chamber to a detection chamber within a closed and sealed container.

BACKGROUND OF THE INVENTION

The amplification of nucleic acids is useful in a variety of applications. For example, nucleic acid amplification methods have been used in clinical diagnostics and in typing and quantifying DNA and RNA for cloning and sequencing.

Devices for performing nucleic acid amplification reactions are known generally as thermal cycling devices or thermal cyclers. One example of such a device is described in published PCT Application, WO 92/20778. The PCT application's cycling device is useful in performing DNA amplification by techniques. The device described in WO 92120778 includes a ring-shaped holder having a plurality of wells for accepting pipette tips containing samples. The samples are contained within the tips by heat sealing an open end of each tip. Means are provided for heating and cooling the ring, thereby allowing the device to cyclically heat and cool samples in the pipette tips. The means for cooling the ring includes a fan for drawing cool air over the ring, and cooling fins positioned radially inward from the ring to assist in directing cool air over the ring. The entire disclosure of PCT Application WO 92120778 is incorporated herein by reference.

Methods of amplifying nucleic acid sequences are known in the art. For example, the polymerase chain reaction ("PCR") method utilizes a pair of oligonucleotide sequences called "primers" and thermal cycling techniques wherein one cycle of denaturation, annealing, and primer extension results in a doubling of the target nucleic acid of interest. PCR amplification is described further in U.S. Pat. No. 4,683,195 and U.S. Pat. No. 4,683,202. The entire disclosures of both of these patents are incorporated herein by reference.

Another known method of amplifying nucleic acid sequences is the ligase chain reaction ("LCR"). In LCR, two primary probes and two secondary probes are employed instead of the primers used in PCR. By repeated cycles of hybridization and ligation, amplification of the target is achieved. The ligated amplification products are functionally equivalent to either the target nucleic acid of interest or its complement. This technique was described in EP-A-320 308, and subsequently in EP-A-336-731, WO 89/09835, WO 89/12696, and Barany, *Proc. Natl. Acad. Sci.*, 88:189–193 (1991). Variations of LCR are described in EP-A-439-182 and in WO 90/01069.

Other known methods of amplifying nucleic acids employ isothermal reactions. Examples of such reactions include 3SR (Self-sustained Sequence Replication) E. Fahy, D. Y. Kwoh & T. R. Gingeras, in PCR Methods and Applications 1:25 (1991); and SDA (Strand Displacement Amplification) G. T. Walker, M. C. Little, J. G. Nadeau & D. D. Shank, in *Proc. Nat Acad. Sci. U.S.A.*, 89:392 (1992).

Amplification of nucleic acids using such methods is usually performed in a closed reaction vessel such as a snap-top vial or a sealable pipette as disclosed in WO 92/20778. After the amplification reaction is completed, the reaction vessel is opened, and the amplified product is transferred to a detection apparatus where standard detection methodologies are used.

Typically, the amplified product is detected by denaturing the double stranded amplification products and treating the denatured strands with one or more hybridizing probes attached to a detectable label. The unhybridized labelled probes usually must be separated from the hybridized labelled probe, and this requires an extra separation step. In other detection methods, the amplification products may be detected by gels stained with ethidiun bromide. Thus, $^{32}P$ tracings; enzyme immunoassay [Keller et al., *J. Clin. Microbiology*, 28:1411–6 (1990)]; fluorescence [Urdea et al., *Nucleic Acids Research*, 16:4937–56 (1988); Smith et al., *Nucleic Acids Research*, 13:2399–412 (1985)]; and chemiluminescence assays and the like can be performed in a heterogenous manner [Bornstein and Voyta, *Clin. Chem.*, 35:1856–57 (1989); Bornstein et al., *Anal. Biochem.*, 180:95–98 (1989); Tizard et al., *Proc. Natl. Acad. Sci.*, 78:4515–18 (1990)] or homogenous manner [Arnold et al., U.S. Pat. No. 4,950,613; Arnold et al., *Clin. Chem.*, 35:1588–1589 (1989); Nelson and Kacian, *Clinica Chimica Acta*, 194:73–90 (1990)].

These detection procedures, however, have serious disadvantages. When the reaction vessel containing a relatively high concentration of the amplified product is opened, a splash or aerosol is usually formed. Such a splash or aerosol can be a source of potential contamination, and contamination of negative, or not-yet amplified, nucleic acids may lead to erroneous results.

Similar problems concerning contamination may involve the work areas and equipment used for sample preparation, reaction reagent preparation, amplification, and analysis of the reaction products. Such contamination may also occur through contact transfer (carryover), or by aerosol generation.

Furthermore, these previously described detection procedures are time-consuming and labor intensive. Probe hybridization techniques typically require denaturing the extension products, annealing the probe, and in some cases, separating excess probe from the reaction mixture. Gel electrophoresis is also disadvantageous because it is an impractical detection method if rapid results are desired.

U.S. Pat. No. 5,229,297 and corresponding EP 0 381 501 A2 (Kodak) discloses a cuvette for carrying out amplification and detection of nucleic acid material in a closed environment to reduce the risk of contamination. The cuvette is a closed device having compartments that are interconnected by a series of passageways. Some of the compartments are reaction compartments for amplifying DNA strands, and some of the compartments are detection compartments having a detection site for detecting amplified DNA. Storage compartments may also be provided for holding reagents. Samples of nucleic acid materials, along with reagents from the storage compartments, are loaded into the reaction compartments via the passageways. The passageways leading from the storage compartment are provided with one-way check valves to prevent amplified products from back-flowing into the storage compartment. The sample is amplified in the reaction compartment, and the amplified products are transferred through the interconnecting passageways to detection sites in the detection compartment by applying external pressure to the flexible compartment walls to squeeze the amplified product from the reaction compartments through the passageways and into the detection compartments. Alternatively, the cuvette may be provided with a piston arrangement to pump reagents and/or amplified products from the reaction compartments to the detection compartment.

Although the cuvette disclosed in EP 0 381 501 A2 (Kodak) provides a closed reaction and detection environment, it has several significant shortcomings. For example, as illustrated in FIGS. 1 to 18 of the application, the multiple compartments, multiple passageways, check valves and pumping mechanisms present a relatively complicated structure that requires some effort to manufacture. Also, the shape and configuration of the cuvette disclosed in EP 0 381 501 A2 do not allow it to be readily inserted into conventional thermal cycling devices. In addition, the fluid transfer methods utilized by the cuvette call for a mechanical external pressure source, such as a roller device applied to flexible side walls or the displacement of small pistons. Conventional thermal cycling devices are not readily adapted to include such external pressure sources. Finally, the apparatus described in this reference is quite limited in terms of throughput of the disclosed devices. The system does not provide the desired flexibility for manufacturing.

French patent publication No. FR 2 672 301 (to Larzul) discloses a similar hermetically closed test device for amplification of DNA. It also has multiple compartments and passages through which sample and/or reagents are transferred. The motive forces for fluid transport are described as hydraulic, magnetic displacement, passive capillarity, thermal gradient, peristaltic pump and mechanically induced pressure differential (e.g. squeezing).

Methods for performing homogeneous amplification and detection have been described in a limited manner. Higuchi et al., *Bio/Technology*, 10:413–417 (1992) describe a method for performing PCR amplification and detection of amplified nucleic acid in an unopened reaction vessel. Higuchi et al. teach that simultaneous amplification and detection is performed by adding ethidium bromide to the reaction vessel and the reaction reagents. The amplified nucleic acid produced in the amplification reaction is then detected by increased fluorescence produced by ethidium bromide binding to ds-DNA. The authors report that the fluorescence is measured by directing excitation through the walls of the amplification reaction vessel before, after or during thermal cycling.

U.S. Pat. No. 5,210,015 also discloses a method of amplifying and detecting target nucleic acid wherein detection of the target takes place during a PCR amplification reaction. The reference teaches adding to the reaction mixture labeled oligonucleotide probes capable of annealing to the target, along with unlabeled oligonucleotide primer sequences. During amplification, labeled oligonucleotide fragments are released by the 5 to 3' nuclease activity of a polymerase in the reaction mixture. The presence of target in the sample is thus detected by the release of labeled fragments from hybridized duplexes.

Co-owned and co-pending application Ser. No. 07/863, 553, filed Apr. 6, 1992 entitled "Method and Device for Detection of Nucleic Acid or Analyte by Total Internal Reflectance" also discloses a reaction vessel wherein amplification and detection are accomplished in the same vessel. Amplification products are captured on an optic element via specific binding to immobilized capture reagents. Combination of the amplification product with the capture reagent brings a fluorescent label within the penetration depth of an evanescent wave set up in the optic element. A change in fluorescence results from the coupling of the fluorescent label and is detected.

In spite of these disclosures, neither closed reaction vessels nor homogeneous assays have gained wide commercial use. Thus, there is a need for an amplification and detection system that avoids the shortcomings of the prior art, and also provides an efficient, reliable and sterile testing environment, in an easily manufactured format.

SUMMARY OF THE INVENTION

In general, the present invention is directed to methods for transferring a fluid sample from a reaction area to a detection area. In the preferred method the reaction area is a thermocycling chamber for nucleic acid amplification analysis, but it will be understood that the invention has broad application to many other target ligands, assay configurations and/or types of chambers.

In one aspect, the invention relates to a method for transferring a fluid sample between a reaction chamber and a detection chamber within a device, comprising the steps of:

a) providing a device having a reaction chamber and a detection chamber connected by means for fluid communication between the reaction and detection chambers, and having a reaction sample disposed in said reaction chamber, wherein a propellant is also disposed in said reaction chamber such that the propellant and sample are intermixed or such that the sample is between the propellant and the means for fluid communication, and wherein further the propellant is inducible to expand; and b) inducing the propellant to expand to occupy a larger volume, thereby forcing the sample through the means for fluid communication into the detection chamber.

Preferably, the reaction chamber is an elongated or tubular construction having at least one or two longitudinal segments and being closed at one end and having an opening into the detection chamber at the opposite end. The propellant, which may be any substance which can be induced to expand, may be the reaction sample itself or it may be a distinct substance lodged at or near the closed end of the reaction chamber. Ideally, the propellant may be induced to expand by a non-mechanical stimulus, such as light or heat. Expansion of a propellant should be distinguished from mechanical pressure increases arising from non-expansion events, such as hydraulic pressure or deformable septums.

Although not required by the invention, expansion of the propellant may encompass a phase change, such as the vaporization of a liquid to a gas. In such a situation, it is convenient to localize the vaporization by using a nucleation site in the reaction chamber. Such a nucleation site may include inert particulate matter, such as boiling chips or glass or plastic microbeads, in the range of about 1.0 to 0.1 mm in diameter, or a grooved, ridged or roughened surface inside the reaction chamber. Preferably, the nucleation site is localized at or near the bottom of the reaction sample to more efficiently force the sample from the reaction chamber.

A preferred use of the method of the invention is for transferring a reaction sample containing nucleic acid that has been amplified by a thermal cycling process such as the ligase chain reaction or the polymerase chain reaction to a detection chamber without opening the sealed reaction/ detection unit, thereby avoiding or significantly reducing the possibility of contamination of the work area by amplified nucleic acid. Thus, a cycling reaction can be effected by applying intermittent heat to a first longitudinal segment and transfer can be effected by applying heat to a second longitudinal segment closer to the closed end. The means for applying heat to the two segments may be the same or different. Alternatively, in the case of a single longitudinal segment and a single means for applying heat, cycling can be effected by intermittently applying a first maximum amount of heat, and transfer can be effected by applying heat in excess of said first maximum to "superheat" the propellant.

BRIEF DESCRIPTION OF THE DRAWINGS

FIG. 2A to 2H illustrate several views of one variation of the reaction/detection unit prior to assembly. FIG. 2A, a partial cross-section taken along line a—a in FIG. 2C, shows the upper or detection chamber. FIG. 2B shows the lower or reaction chamber aligned for insertion into the detection unit FIG. 2C is a cross sectional view taken along lines c—c in FIG. 2A. FIGS. 2D and 2E are cross sectional views taken along lines d—d and e—e, respectively, in FIG. 2C. It can be seen that FIG. 2D represents a front angle, while FIGS. 2A and 2E represent side angles. FIGS. 2F, 2G and 2H show the reaction/detection unit after sealably engaging the reaction chamber to the detection chamber, and inserting it into the thermal cycler holder. FIG. 2F is a side cross sectional view like 2A, while FIG. 2G is a front cross sectional view and shows a variation in the keying means. FIG. 2H is a cross section taken along line h—h in FIG. 2F.

FIGS. 3A to 3D illustrate several embodiments and variations of a reaction/detection unit in accordance with the invention. FIGS. 3A and 3B illustrate a snap-fit embodiment of the reaction/detection unit after sealably engaging the reaction chamber to the detection chamber. FIGS. 3C and 3D show in cross-section a variation of the reaction/detection unit, wherein the engaging means and detection configuration differ from those of FIGS. 3A and 3B.

FIG. 4A shows a standard friction or Luer fit in cross-section; FIG. 4B shows a pawl or snap fit seal in cross-section; FIG. 4C shows a different variation of a pawl or snap fit seal in schematic; and FIG. 4D shows a screw thread type seal in cross-section.

FIGS. 5A to 5D illustrate the transfer of an amplification reaction sample from the reaction chamber to the detection chamber of the unit, according to methods of the invention. Above each side view of the detection chamber is a front view of same.

FIG. 8A shows an embodiment with a motorized ring; FIG. 8B shows a stationary ring with motorized mirror and lamp; FIG. 8C depicts a reflectance detection arrangement; and FIG. 8D depicts a transmission detection arrangement.

DETAILED DESCRIPTION OF SOME EMBODIMENTS OF THE INVENTION

OUTLINE OF DETAILED DISCLOSURE

Figure 1:
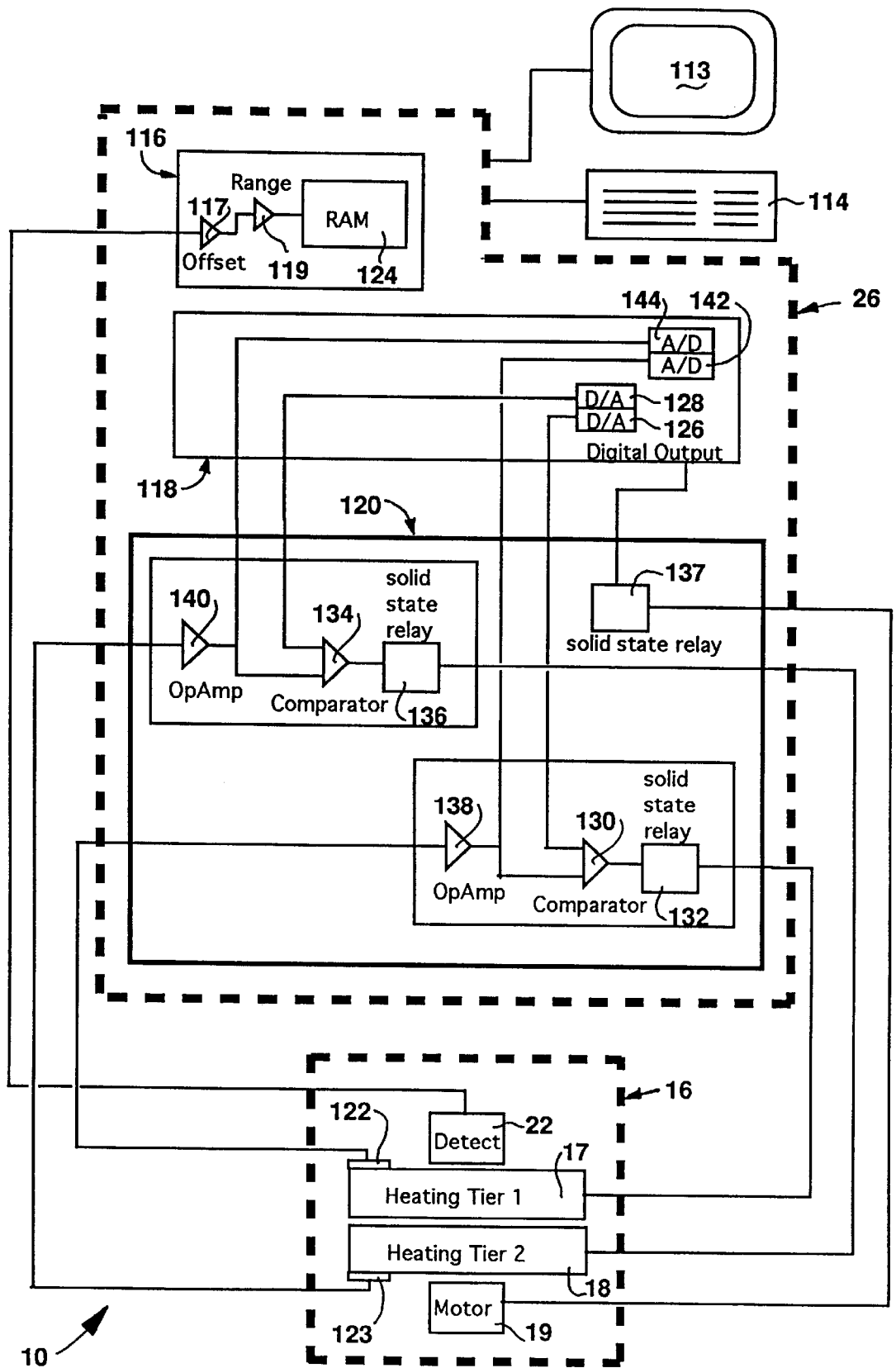
FIG. 1 illustrates by block diagram the general components of the system of the present invention.

1. System Overview
2. Reaction/Detection Units
   a. Reaction Chambers
   b. Detection Chambers
   c. Detection Supports
   d. Sealing Mechanisms
3. Thermal Cycling and Transfer Device
   a. Cycler Devices
   b. Transfer Methods
4. Detection Systems
5. Computer/Circuit Controls
6. Heat Control
   a. Hardware
   b. Software
7. Video Processing
8. Methods for Amplifying and Detecting Nucleic Acids
9. Kits of the Invention
10. Examples
11. Sequence Listing
1. System Overview FIG. 1 is a generalized schematic diagram of an amplification and detection apparatus configured in accordance with the invention. The apparatus 10 includes a thermal cycling device 16, including first and second heating element tiers 17 and 18 and associated thermosensors 122, 123, a fan motor 19 and a detection system 22, each of which will be described in more detail below. The apparatus 10 also includes a computer controller 26 coupled to the thermal cycling device 16. In general, the thermal cycling device 16, under control of the computer 26 which sends independent signals to each of heater tier 1 (17) and heater tier 2 (18), is capable of independently delivering prescribed temperature (s) to localized segments of reaction containers housed inside the thermal cycler device 16, in order to amplify and/or transfer target nucleic acid present in the reaction samples. Details of the computer control of the device 16 are described in later sections.

Figure 3A:
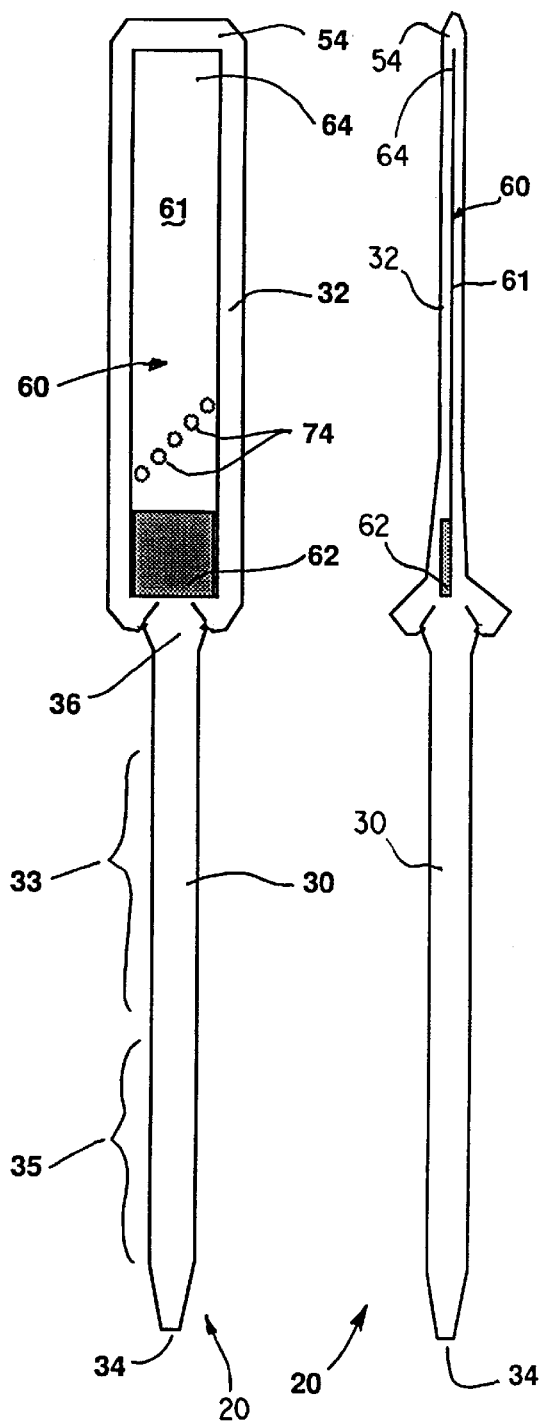
Figure 3B:
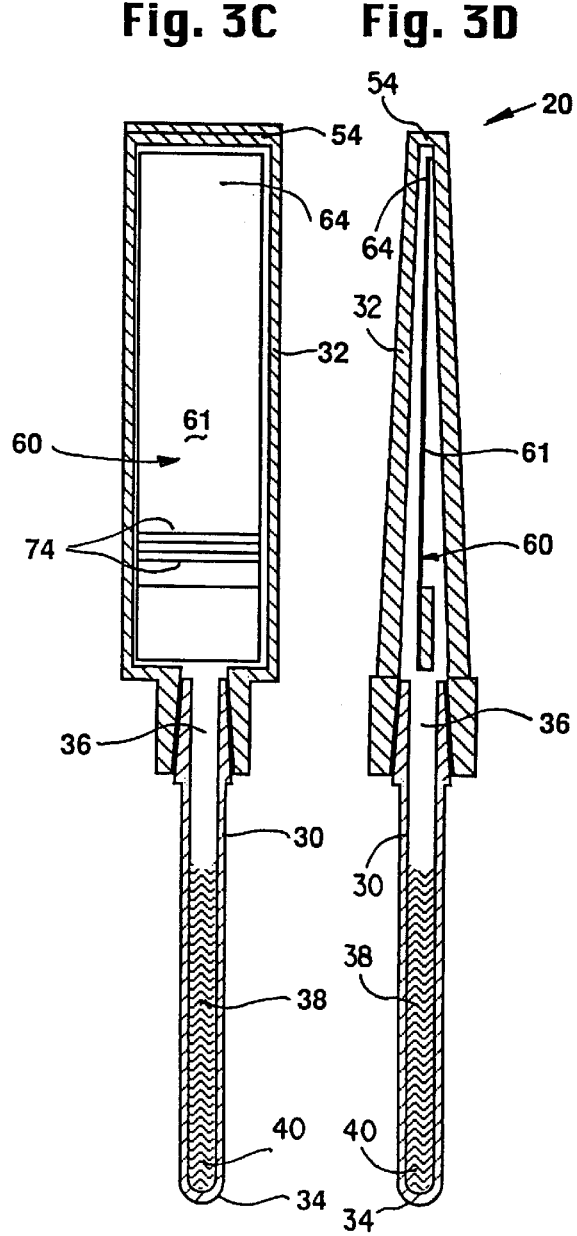

The apparatus 10 also includes a plurality of reaction/detection units 20 (see FIGS. 2–3). The units 20 have a two-part, sealable construction that includes a reaction chamber 30 and a detection chamber 32, as shown in FIGS. 2A to 2H and 3A to 3D. The reaction chamber 30 houses the reaction sample for carrying out the desired amplification reactions. The detection chamber 32 is provided with means for generating a detectable indication of the results of the amplification reaction. Specific aspects and variations of these reaction/detection units 20 are described in detail later in this disclosure.

The amplification reaction methods begin by inserting a reaction sample 38 into the reaction chamber 30, along with desired amplification reagents. The detection chamber 32 is then mated with the reaction chamber 30 to form the sealed unit 20 which is then placed into the heating tiers 17, 18 of the thermal cycling device 16 as best shown in FIGS. 2F and 5A–5D. After the reaction and detection chambers 30, 32 are mated, the unit 20 remains sealed, thus providing a closed environment for carrying out both amplification and detection.

The computer 26 controls the temperature settings and the timing of any temperature cycles, depending on the type of amplification reaction that is being performed. For amplification reactions such as PCR or LCR, the computer 26 is programmed to take the heating tiers through one or more cycles of a high/denaturing temperature, followed by a low/annealing temperature. Where two tiers are provided, the computer 26 is capable of controlling the temperature of the upper heating tier 17 independently of the lower heating tier 18, although they may also follow identical protocols.

At the end of the amplification reaction and without opening the sealed reaction/detection unit, the reaction sample is transferred from the reaction chamber 30 to the detection chamber 32 of the sealed unit 20. The reaction sample is preferably transferred by expanding a propellant in the reaction chamber 30 to force the sample and reagents into the detection chamber.

The detection chamber 32 includes detection means for generating a detectable indication of the results of the amplification reaction. Generally, the detection means includes a support 60 having one or more capture sites 74 for immobilizing and accumulating amplified target nucleic acid present in the reaction sample 38. The immobilized amplified target nucleic acid is associated with a detectable indicator at the capture sites 74, and this indicator is detected and analyzed by the detection system 22 and the computer 26.

The various components of the apparatus 10 will now each be described in greater detail, including multiple variations on the general overview set forth above.

2. Reaction/Detection Unit a. Reaction Chambers

Reaction/detection units 20 of the present invention are shown in FIGS. 2A to 2E, 3A to 3D and in other figures as well. Each unit 20 includes a reaction chamber 30 and a detection chamber 32. The unit 20 may be disposable.

The nucleic acid amplification reaction takes place in the reaction chamber 30. The reaction chamber 30 is made of a material such as glass or plastic that can withstand the temperatures necessary for denaturation of nucleic acids, typically 80–110° C. The bottom end 34 of elongated reaction chamber 30 is closed, and the top end 36 is open to accept a reaction sample 38 and, if desired, amplification reaction reagents. Such reaction reagents may be added to the reaction chamber 30 by the user, but they are preferably included during manufacture and enclosed by a removable or rupturable seal (not shown), in which case only the test sample is added by the user. Test sample can be inserted in the reaction chamber 30 by any known means. For example, it can be placed in a syringe (not shown) and inserted into the reaction chamber 30 by removing the seal or puncturing it with a hollow-bore syringe tip. Thus, reaction sample 38 in the chamber 30 includes both the test sample and amplification reagents. It may additionally include a propellant 40 and one or more components of the detection system.

The size of the chamber 30 should be selected so as to barely contain the relatively small quantities of reaction sample 38. Preferably, the chamber 30 is dimensioned to hold a reaction sample of about 10 μL to about 200 μL. Even more preferably, the chamber 30 holds about 50 μL to about 120 μL. The reaction chamber should also be of suitable dimensions so that surface tension in the reaction chamber 30 is reduced and bubbling of the reaction sample during heating is avoided. Further, the reaction chamber 30 should have a high surface area to volume ratio to enhance the rate of heat transfer to the reaction sample. Preferably, the reaction chamber 30 is an elongated tubular shape having a longitudinal axis. In one preferred embodiment, the reaction chamber 30 is a microsyringe tube or capillary tube sealed at the bottom end.

It has been found that smooth interior-walled reaction chambers perform poorly compared to chambers that have irregular surfaces in the interior, particularly at the closed or bottom end 34. For example, open microsyringe or capillary tubes that are heated to seal one end perform well, the heating apparently introducing irregularities in the interior surface; while a closed-end capillary tube (e.g. from Varivest, Grass Valley, Calif.: see example 4) performed less well unless it too was melted first. It is hypothesized that the irregular surface provides a nucleation site for vaporization to begin at or near the bottom of the sample. However, applicants do not intend to be limited to or bound by any particular theory or mechanism of operation.

Mechanically grinding or roughening of the interior of the tubes will also improve performance as will grooves or ridges in the interior. Performance may also be improved by the addition of small boiling chips or sticks, or microparticle beads to the bottom of the reaction tube. For example, beads of polystryene, glass, ceramic, stainless steel or other suitable inert material ranging in size from about 1.0 to 0.1 mm diameter are useful as nucleation sites. Particle size is not thought to be critical, provided the particles fit within the reaction chamber. Such particles should be inert to the reaction reagents and should be more dense than the reaction sample.

b. Detection Chambers

The separation of amplified target nucleic acid from the reaction sample takes place in the detection chamber 32, as shown in FIGS. 2 and 3. The detection chamber 32 is made of a transparent material, such as plastic or glass, and has an open end 48 and a closed end 54. Reaction sample 38 flows into the detection chamber 32 via the open end 48, where it encounters a detection support 60 (described in detail below).

In a preferred embodiment (FIG. 2) the detection chamber includes a reservoir 37 for holding sample fluid delivered from the reaction chamber. This may be accomplished, for example, by directing the sample fluid into open end 48 and through a flow path having an orifice 39 above the level of the floor of the detection chamber 32, so that fluid enters from the side of the chamber. Alternatively, a standpipe inlet can create a reservoir. The reservoir 37 maintains a supply of reaction sample fluid available to the detection support means 60, even in the face of cooling and receding of the fluid sample within the reaction chamber 30 (Compare FIGS. 5C and 5D, in which fluid in the reservoir is absorbed by the strip 61 rather than receding back down the reaction tube). For elongated detection chambers having reservoirs and a side entry orifice 39, it may also be helpful to mold angled fins 43 to bestow additional strength on the entire detection chamber.

In another preferred feature, the cross sectional shape (FIG. 2C) of the detection chamber is polygonal or asymmetric such that it may be seated in a matching groove in the heating tier in only one possible orientation. This is best shown in FIGS. 2F and 2H, which depicts a trapezoidal shaped seat. For transmission detection configurations (see infra) it is preferable that the front and rear faces of the chamber remain substantially parallel. A trapezoid is the simplest polygon that does this while still dictating a fixed orientation. However, other polygonal or asymmetric shapes may be envisaged. For reflectance detection configurations (see infra), the front and rear faces need not be parallel and other polygons are suitable. If a rounded seat configuration is employed it may possess a cam or a flat side to dictate a single orientation. The seat need not have the same configuration as the optical face(s).

The detection chamber 32 (and/or the reaction chamber 30) may include tab members 58 (shown in FIGS. 2G and 7) which support the chamber within the thermal cycling device 16 and which provide for easy handling. The tab member 58 may also include means for engaging a key groove 91 (shown in FIGS. 2G and 7) located in the heating tier 17. This alternative to the polygon shape also ensures a prescribed orientation for the detection chamber 32 with respect to the heating tier; and also with respect to the detection system 22 provided the detection system is fixed with regard to the heating tier.

FIGS. 3A–3D show alternative embodiments to the preferred embodiment of FIG. 2. These embodiments have similar components and features and these have been given the same reference numeral as in the embodiment of FIG. 2. The embodiments of FIG. 3 do not, however, include the reservoir feature.

The unit 20 can also be provided with a bar code (not shown) which is preferably located on the detection chamber 32. A bar code reader (not shown) provided on the thermal cycling device 16 for reading the bar code can then communicate the encoded information to the computer 26. The bar code can identify the particular unit 20 and can provide other pertinent information about the sample and the reaction to be performed. Some of this information may include the patient identity and/or the configuration of the capture sites 74 as described later in this disclosure in connection with the video processing program implemented by the computer 26.

c. Detection Supports

The detection chamber 32 also includes detection support means 60 for accepting the reaction sample, separating the amplified target DNA and generating a visible indication of the results of the amplification reaction. Typically the detection support means includes a solid support on which signal indicative of the presence of target can be accumulated, as is well known in heterogeneous assays.

Such solid supports include, for example, plastics, glass, natural and synthetic polymers and derivatives thereof, including cellulose esters, microporous nylon, polyvinylidine difluoride, paper and microporous membranes. Supports may be shaped, for example, as fibers, beads, slides, cylindrical rods or strips. In a preferred embodiment, the detection support means 60 is a microporous strip 61 shown in FIGS. 2, 3 and 5 capable of supporting capillary migration. More preferably, the porous support is nitrocellulose, such as nitrocellulose having pore size of about 2 µm to about 20 µm, usually 5 or 10 µm. Preferably, the porous support is inert, or rendered inert through the use of blocking agents and/or transport facilitating agents (see, e.g. U.S. Pat. No. 5,120,643) and does not generally react physically or chemically with any of the reagents or target nucleic acid in the reaction sample. The use of transport facilitating agents is known in the art, and is further discussed in Example 3. Porous and microporous supports exhibit wicking by capillarity and chromatographic properties; however, non-chromatographic supports and non-porous supports are contemplated by the invention as well.

The detection support means 60 can be any suitable shape, including a round or disc shape, or rectangular shape. The size or dimensions of the detection means 60 should be selected to provide sufficient resolution of the visible indicator produced by amplified target nucleic acid immobilized on the detection means 60. The detection means 60 is preferably small and/or thin in order to shorten the time needed for detection of immobilized target nucleic acid and to minimize material usage. Those skilled in the art will be able to optimize dimensions of the detection means 60 in relation to the volume of the reaction sample 38, the amount of amplified target, and the size of the reaction chamber 30 and the detection chamber 32. The detection chamber 32 may be configured to house the detection means 60.

Typically, different support materials 60 will accept and transport the reaction sample 38 at varying rates depending, for instance, on pore size and thickness of the support. The support should be selected so that it does not transport the reaction sample 38 past specific binding pair members or capture molecules, described further below, at a rate that exceeds the time required for binding amplified target nucleic acid.

The preferred support 60 is a strip 61 that includes a first end 62 at which reaction sample transport begins, a second end 64 at which reaction sample transport ends, and one or more regions 66, 68, 70 containing the mechanisms for allowing amplified target nucleic acid to be isolated in the detection chamber 32.

As shown in FIGS. 2D and 5D, the strip 61 comprises at least two regions, wherein a first region 66 at or near the first end 62 of the strip 61 functions in labeling amplified target nucleic acid present in the reaction sample, and a second region 68 functions in separating the labeled amplified target nucleic acid from the reaction sample by immobilizing the amplified target on the strip 61. The second region 68 may include one or more zones, with each zone including at least one capture site 74 for immobilizing target nucleic acid and providing a visible indication when the target nucleic acid has been immobilized on the capture site. Capture sites 74 may be arranged as continuous bands, as in FIGS. 2D and 3C; as discontinuous bands, as in FIG. 2G; or as individual spots, as in FIGS. 3A and 5A–5D. The significance of multiple capture sites and replicate sites within a capture area is discussed infra.

It will be realized that the labelling function need not occur on the strip itself, but may occur at any point between the reaction sample and the capture sites, including within the reaction sample. For example, a conjugate pad may be attached to the bottom end of a detection support medium. Such a pad might also be placed in the open end 36 of the reaction chamber, in the open end 48 of the detection chamber, or in the orifice 39 or the reservoir 37 of the embodiment shown in FIG. 2. If the conjugate pad is not attached to the strip it appears preferable to at least have it contact the strip.

The strip 61 may include a third region 70 which functions as a control zone or reference standard for the detection system 22. Preferably, all such regions 66, 68, 70 are spatially distinct areas of the support 61. The functions of the regions 66, 68, 70 are described in further detail below in connection with the methods for detection of amplified target nucleic acid(s).

The support 61 may, if necessary, be affixed to an inert substrate preferably made of a transparent material such as glass, plastic or nylon which is sufficiently rigid to provide structural support. In the embodiment depicted in FIGS. 2 and 5, the detection chamber is equipped with pins or fingers 41 which hold the strip rigidly in position. Such pins or fingers 41 can be molded into the chamber housing during manufacture. The support and substrate are preferably in a fixed location or angle within the detection chamber 32 so that detection of amplified target nucleic acid immobilized on the support 61, as described further below in connection with the methods of the invention, can take place at a predetermined location or angle with respect to the detection system 22.

d. Sealing Mechanisms

Detection chamber 32 is designed to sealingly mate with the reaction chamber 30 to prevent the escape of any amplified nucleic acid once the amplification reaction is performed. For this reason, reaction/detection unit 20 includes engagement means for sealably engaging the chambers 30, 32 together. The engagement means may be accomplished by any of several known means. The engagement means should form a secure seal so that the chambers 30, 32 do not leak potentially contaminating fluids; in other words, they should not become unsealed or disconnected under conditions of increased temperature or pressure, or under normal handling and/or disposal FIGS. 4A to 4D illustrate several mechanisms for sealably engaging or mating the two chambers 30, 32 of the unit 20. Perhaps the simplest mechanism is the standard Luer or friction fit. This is illustrated in enlarged detail in FIG. 4A, as well as in FIG. 2 and others. The open top end 36 of the reaction chamber 30 includes an angled facing 44 around its outside perimeter, and the open end 48 of the detection chamber 32 includes an angled facing 50 around its inside perimeter. The angle of the bevel on the two faces 44, 50 is matched so that a tight friction fit is achieved when the two chambers are pressed together as shown in FIGS. 2E, 2F, 3C, 3D and 4A. Although not shown, variations on this sealing mechanism include the Luer lock system and a bayonet locking system.

Figure 4A:
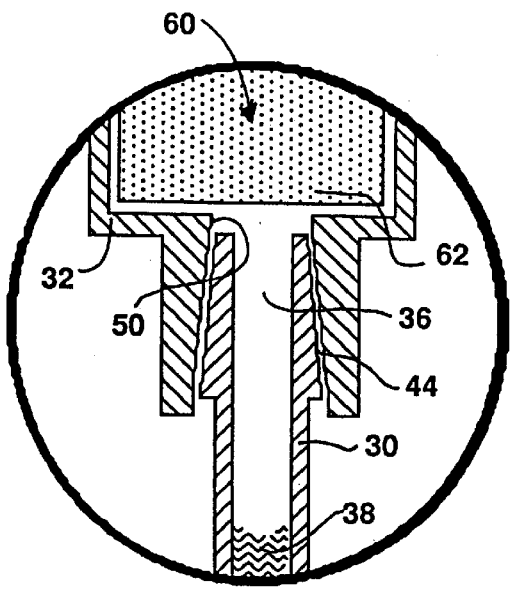
FIGS. 4A to 4D illustrate enlarged views of the sealable engaging means of the assembled reaction/detection unit.
Figure 4B:
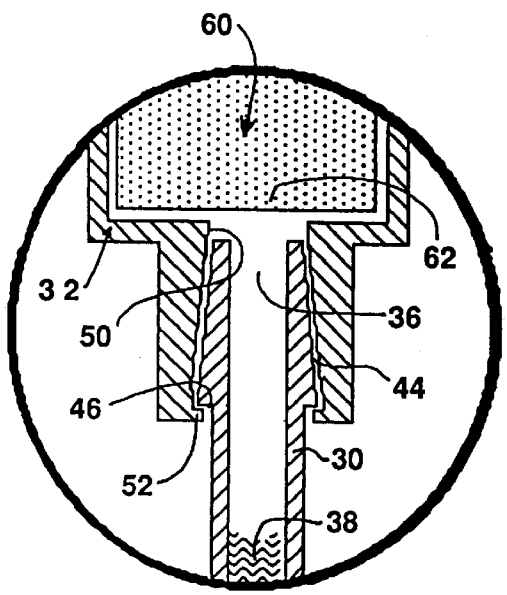

A second sealing mechanism is illustrated in detail in FIG. 4B. This is a snap-fit or pawl variation of the standard Luer fit. The top end 36 includes the beveled face 44 and an annular shoulder or pawl 46 around its outer periphery. The detection chamber 32 includes the beveled face 50 and an annular pawl or shoulder 52. Again, the bevel angle is matched to produce a tight seal, and the annular shoulders 46, 52 lock with one another to prevent the two portions from becoming separated. Another variation of a snap fit seal is illustrated in FIG. 4C. Although shaped somewhat differently, the elements are all similar and have been given identical reference numerals. A snap-fit is achieved by engaging the ends such that shoulder 52 moves over facing 44 and into engagement with shoulder 46.

Figure 4D:
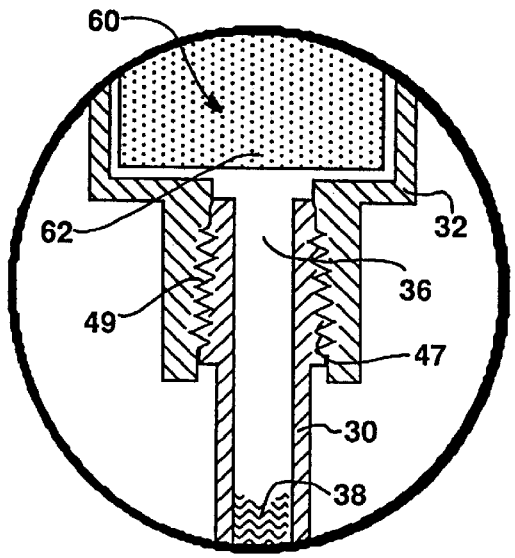
Figure 4C:
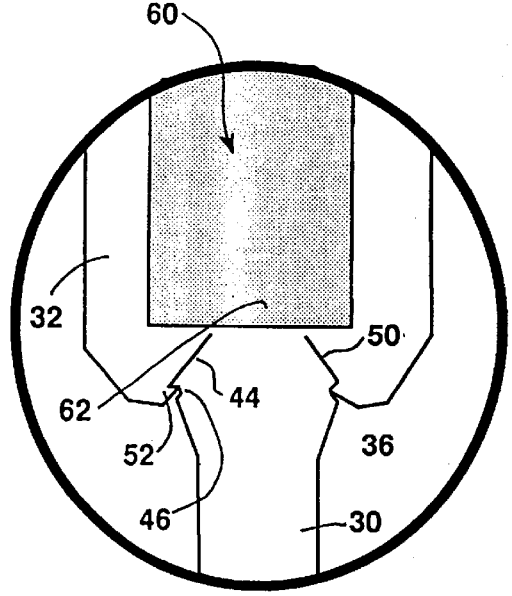

In a final sealing mechanism, illustrated in FIG. 4D, the open end 36 of the reaction chamber 30 is fitted with male screw threads 47. The inside of the open end 48 of the detection chamber 32 is similarly fitted with matching female screw threads 49. By twisting the reaction chamber into the detection chamber, a sealed reaction/detection unit is obtained. Many other equivalent seal variations are possible and within the scope of the invention. Ideally, the seal mechanisms are virtually irreversible under normal handling conditions.

Reaction/detection units 20 according to the invention may be used with either one or two tier thermal cycling devices, as described below.

3. Thermal Cycling and Transfer Device a. Cycler Devices

Figure 6:
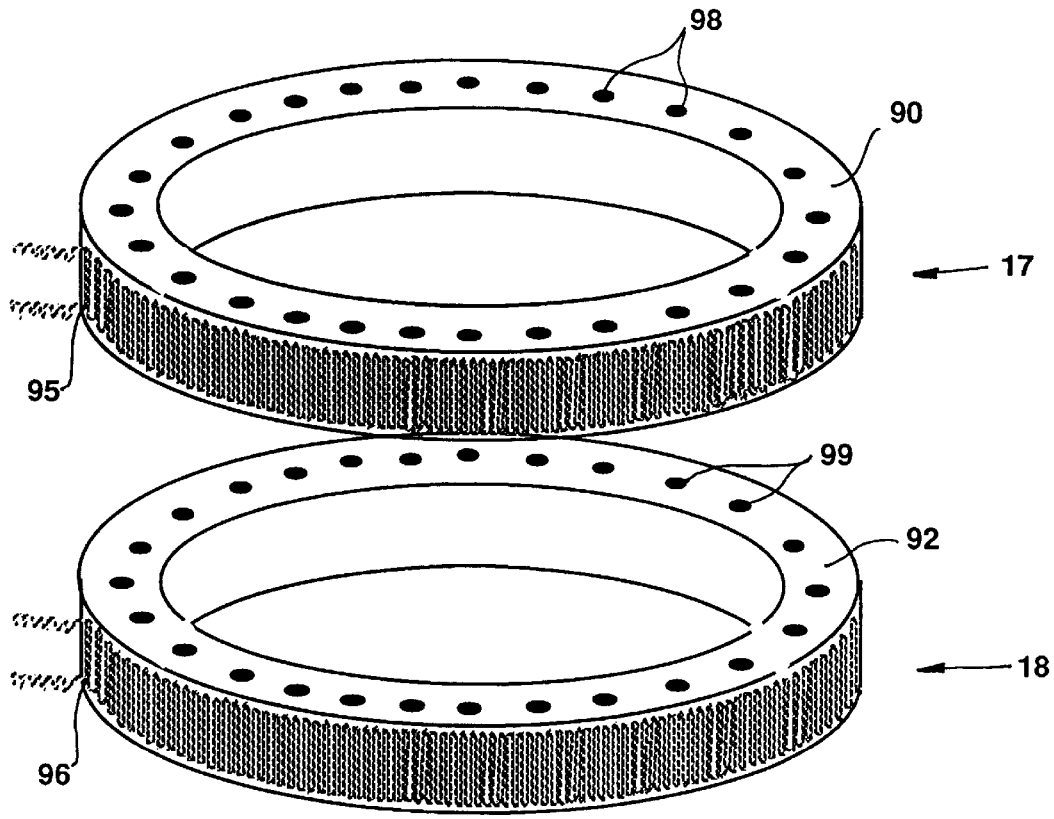
FIG. 6 illustrates a preferred embodiment of a two-tier heating element for use in connection with the invention, each tier being configured as an annular ring.
Figure 7:
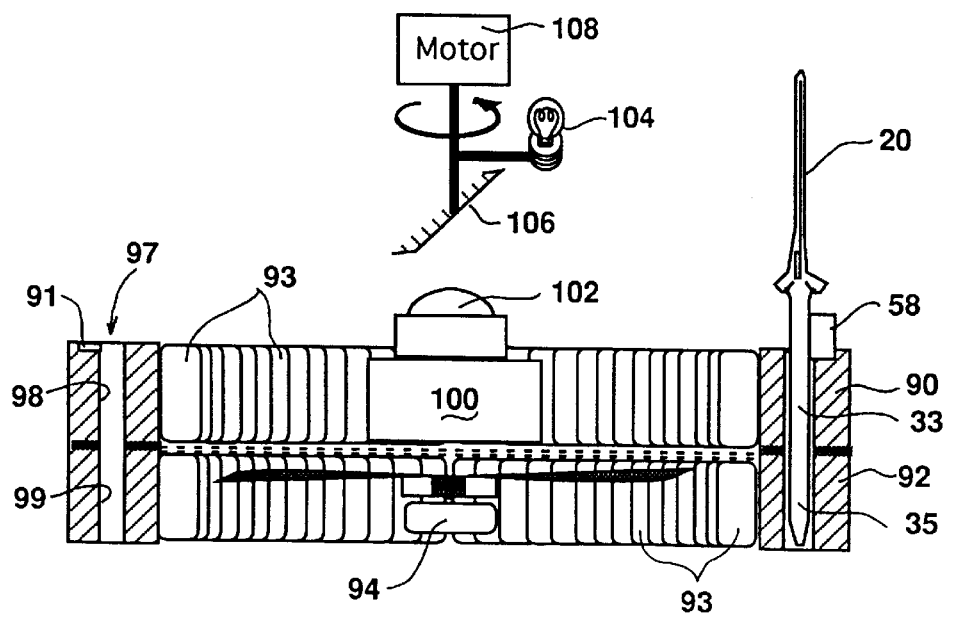
FIG. 7 illustrates a partial cross-sectional view of a preferred thermal cycler device of the invention.

FIGS. 6 and 7 illustrate the details of a preferred embodiment of the thermal cycling and transfer device 16 shown schematically in FIG. 1. It should be understood, however, that both one-tier and multi-tier heating/transfer units are suitable for use with the devices and methods of the invention. Thus, the cycler 16 includes at least one heating tier 17, and optionally two heating tiers 17 and 18 for delivering the desired temperature(s) to the reaction chamber 30 under control of the computer 26. In one embodiment the heating tiers constitute an annular upper heating ring 90 that is spatially separated from an annular lower heating ring 92. The airspace between the heating rings 90, 92 acts as an insulator, although other insulating materials may be employed. The heating tiers may have a variety of other shapes such as linear, planar or wedge (not shown). One or more cooling fins 93 are placed on the rings 90, 92, typically spaced radially inward to assist in reducing the temperature of the rings 90, 92 during cooling periods. A fan 94 is positioned below the cooling fins 93 to further assist in reducing the temperature of the rings 90, 92 during cooling periods.

The heating rings 90, 92 are made from a heat conducting material such as aluminum, copper or gold. Heat may be delivered to the rings 90, 92 via conventional resistive heat strips 95, 96 attached to the rings, preferably along a perimeter surface of the rings 90, 92 as shown in FIG. 6, or by other known means such as a manifold or by conductance. In multi-tier systems, the computer 26 can independently control the temperature of each heating ring 90, 92 by supplying power independently to the each of the heat strips 95, 96. It can also track the two tiers together as if one.

As shown in FIG. 7, the unit 20 is placed inside one of several apertures or wells 97 in the heating rings 90, 92 such that a first longitudinal segment 33 of the reaction chamber 30 is exposed to the upper ring 90, and a second longitudinal segment 35 of the reaction chamber 30 is exposed to the lower ring 92. As shown in FIGS. 6 and 7, the wells 97 are each made from an aperture 98 in the upper ring 90 in registration with an aperture 99 in the lower ring 92. The upper ring apertures 98 extend completely through the upper ring 90. The lower ring apertures 99 may extend wholly through the lower ring 92, as shown in FIGS. 2G and 7, provided there is some means for supporting the reaction/detection unit 20 in the well 97 such as the tab member 58 described earlier. Alternatively, apertures 99 may extend only partially through the lower ring 92 to allow the closed bottom end 34 of the reaction chamber 30 to rest in the lower ring 92.

The computer 26 (see FIG. 1) controls the upper heating ring 90, the optional and lower heating ring 92 and the fan 94 to direct preselected temperature(s) to the reaction sample 38 in the reaction chamber 30. The heating and cooling cycles of the thermal cycling device 16 and their control by the computer 26 are described in more detail below in the disclosure relating to Computer/Circuit Controls. When the amplification reaction is complete, the computer 26 directs the heating element to deliver heat to the propellant 40 at or above its threshold expansion temperature. When the threshold temperature is reached, the propellant 40 expands, thereby forcing the reaction sample 38 upward into the detection chamber 32. In one embodiment the propellant is expanded by heating the lower ring 92 in excess of the upper ring 90.

b. Transfer Methods

FIGS. 5A–5D illustrate the reaction sample 38 as it is transferred from the reaction chamber 30 to the detection chamber 32 in a one tier apparatus. The unit 20 is placed inside aperture 97 in the heating element 16. In an alternate two tier system, the reaction chamber 30 is placed in the apertures such that a first longitudinal segment 33 (FIGS. 2B and 3A) of the reaction chamber 30 is exposed to the upper ring 90, and a second longitudinal segment 35 (FIGS. 2A and 3A) of the reaction chamber 30 is exposed to the lower ring 92.

In FIG. 5A, the amplification reaction has been completed, and the heating element 16 is being raised to the threshold temperature of the propellant 40. In two tier systems the upper ring 90 may initially be held to a temperature below the threshold temperature to reduce the potential for evaporating the reaction sample 38 after the amplification reaction is complete. It is preferred that the propellant threshold temperature be above the highest amplification reaction temperature(s) so that the propellant 40 does not expand during the amplification reaction.

As used in the present invention, "propellant" refers to any substance that expands in response to a stimulus, preferably a non-mechanical stimulus. For instance, the propellant 40 may be a gas (such as air), a liquid, or a solid compound. In the case of liquid and solid propellants, they are generally vaporizable to cause expansion. The stimulus for expanding the propellant 40 may be, for example, heat, light, or a combination thereof, but preferably is heat in the present invention. The reaction sample 38 itself may serve as propellant 40. Mechanical pressures, such as hydraulics or septum deformation do not result in expansion of a propellant.

In FIG. 5B, the heating element 16 has heated the propellant 40 to its threshold temperature, and the propellant 40 has expanded to push the reaction sample 38 upward toward the detection chamber 32. In two tier systems at this point, the upper heating ring 90 may be brought to the threshold temperature to assist in expanding the propellant 40 as it moves up through the first longitudinal segment 33. As will be described later in connection with FIG. 10, the computer 26 is provided with a programmable time delay to allow the upper heating ring 90 to be superheated to the threshold temperature after the lower heating ring 92.

The heating element 16 (or both upper and lower heating rings 90, 92) continue to deliver the threshold temperature to expand the propellant 40, as shown in FIGS. 5B and 5C, until the reaction sample 38 has been transferred completely into the detection chamber 32, preferably into reservoir 37 thereof via side opening 39.

In FIG. 5C, the first region 66 of the detection strip 61 is beginning to become wetted. This region (or a prior portion of the sample path, see above) preferably contains a label (e.g. zone 67) which becomes associated with the amplified target nucleic acid passing through this region. One method for accomplishing this association is by means of a hapten bound to the nucleic acid and a colloidal particle conjugated with anti-hapten antibody. Colloidal gold or selenium are suitable labels, as is colored latex particles. Haptens and haptenation is known in the art, especially bi-haptenation methods in connection with LCR and PCR amplifications of nucleic acid. For example, see EP-A 357 011 and EP-A-439 182. As the haptenated nucleic acid passes through zone 67, label conjugate is solubilized and mobilized by the reaction solution and it binds with the haptens on the nucleic acid. As an alternative, one may attach a detectable label directly to the probe/primer provided it does not interfere with hybridization or any required enzymatic activity, such as extension and ligation.

As the solution migrates up the strip 61, it encounters the capture sites 74 in region 68, and optionally the control sites in region 70. At the capture sites 74, a second antibody against a second hapten is immobilized against transport. All nucleic acid bound to this hapten becomes immobilized at these sites. If the immobilized nucleic acid was amplified and thereby contains the first bapten as well, then conjugate will accumulate at the capture site and become detectable (FIG. 5D). Each capture site 74 may contain immobilized antibody against a different hapten, thus enabling multiplex amplification and detection by the methods of the invention. Alternatively, multiple capture sites 74 may contain antibody against the same hapten, thus enabling an averaging of the signal among each of the sites.

It should also be understood that the transfer by thermal expansion aspects of this invention are not limited to nucleic acid assays or to thermal cyclers. The transfer aspect is useful any time it is desired to move a reaction sample from a reaction location to a detection location. It is especially useful in situations where it is desirable (e.g. for contamination reasons) to make the transfer within a sealed or closed container. However, it may be used in non-amplified and non-nucleic acid assays, such as immunoassays, provided the reagents can tolerate the levels of heat necessary to effect the transfer.

4. Detection Systems

The results of the amplification reaction are detected and analyzed by the detection system 22 and the computer controller 26. The detectable label is preferably a visible label, but other detectable labels, such as UV, IR or fluorescent labels, are also possible. The preferred detection system 22 generates a video image of the support 60 and includes a video camera 100 and a light source 104 (both shown in FIGS. 7 and 8A to 8D) for illuminating the support 60. An image of the support 60 is provided to the camera 100, either directly or by reflection, and the camera 100 generates a video image which is fed to the computer 26. For simplicity, visible labels will be discussed further.

A variety of configurations are suitable for the detection system 22; some are depicted in FIGS. 8A to 8D. In general, the detection system 22 should include a light source 104 for illuminating the detection means 60 and a camera 100 for creating video images of the detection means 60. The camera lens may be pointed directly at the detection means 60, or a mirror may be provided for reflecting an image of the detection means 60 to the camera lens.

Figure 8A:
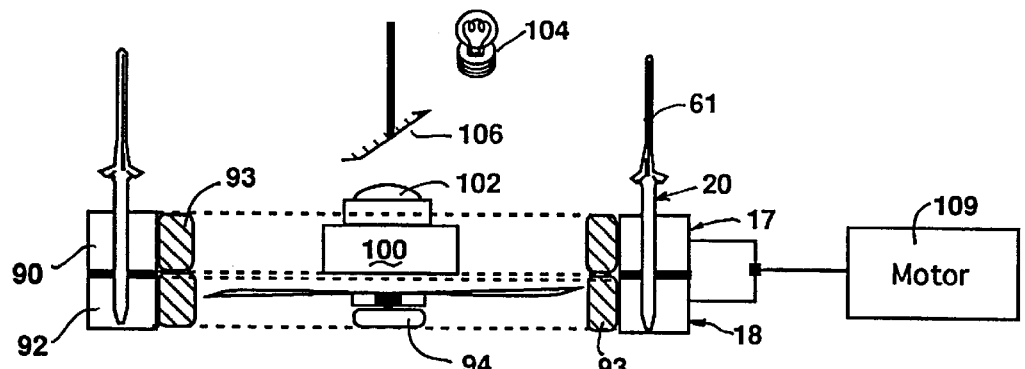
FIGS. 8A to 8D illustrate alternative embodiments of preferred detection systems of the invention.
Figure 8B:
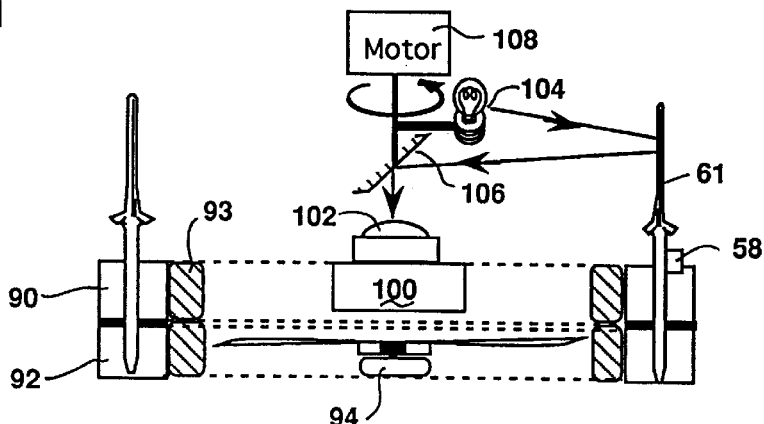

As shown in FIG. 8B, the detection system 22 includes a camera 100, a camera lens 102, a light source 104, a mirror 106 and a motor 108 (preferably a stepper motor) coupled to the mirror 106. The light source 104 is positioned such that the camera lens 102 measures the colorimetric signals reflected from the support 61. The camera 100 and the mirror 106 are positioned axially with respect to the heating rings 90, 92, and the mirror 106 is positioned at an angle such that it reflects an image of the porous support 61 to the camera lens 102. The camera 100 is stationary, and the mirror 106 is rotated by the motor 108 under computer control to successively present an image of the strip 61 of each detection chamber 32 to the camera lens 102. The camera 100 generates a video image of the strip 61 of each detection chamber 32 and passes this image to the computer 26 for analysis. The software for analyzing this image is described later in the Video Processing section.

FIG. 8A illustrates another configuration of the detection system 22. This detection system includes a camera 100, a camera lens 102, a light source 104, a mirror 106, and a motor 109 coupled to the heating rings 90, 92. The light source 104 is positioned such that the camera lens 102 measures the colorimetric signals reflected from the support 61. The camera 100 and the mirror 106 are positioned axially with respect to the heating rings 90, 92, and the mirror 106 is positioned at an angle chosen so that it reflects an image of the support 61 to the camera lens 102. The camera 100 and the mirror 106 are stationary, and the heating rings 90, 92 are rotated by the motor 109 under computer control to successively move each detection means into view to present an image of the strip 61 of each detection chamber 32 to the mirror 106 which reflects the image to the camera lens 102. The camera 100 generates a video image of the support 61 of each detection chamber 32 and passes this image to the computer 26 for analysis.

In an alternative embodiment, the camera lens 100 can be pointed directly at the support 61, thus eliminating the need for the mirror 106. In another alternative, the light source may be inside the ring while the camera is outside the ring, or vice versa These alternatives utilize transmission detection, discussed below in connection with FIG. 8D.

Figure 8C:
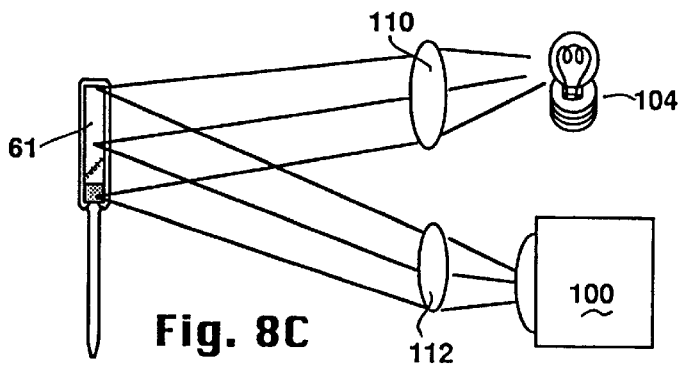

In FIG. 8C, a reflectance fluorescence detection system is provided with a camera 100, a camera lens 102, a light source 104, an excitation filter 110 and an emission filter 112. The light source 104 and the camera 100 are positioned such that the camera lens 102 receives the fluorescent signals emitted from the support 61 in the detection chamber 32. The excitation filter 110 is positioned between the light source 104 and the support 61, and the emission filter 112 is positioned between the support 61 and the camera lens 102.

Figure 8D:
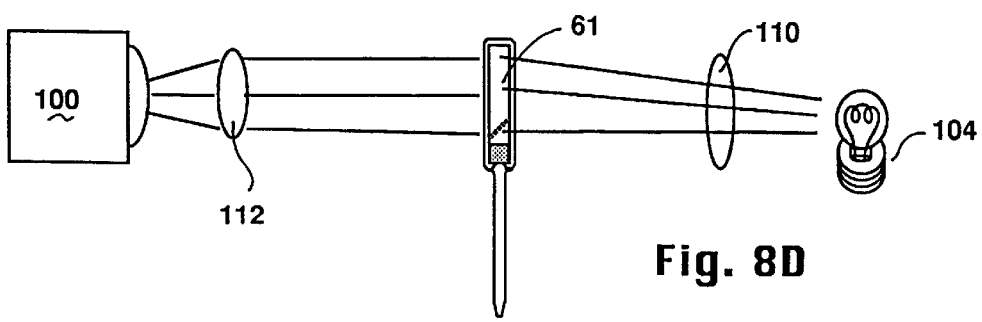

In FIG. 8D, another fluorescence detection system is provided with a camera 100, a camera lens 102, a light source 104, an excitation filter 110 and an emission filter 112. The light source 104 and the camera 100 are positioned such that the support 61 is between the light source 104 and the camera 100. Thus, the camera lens 102 receives the fluorescent signals transmitted through the support 61. The excitation filter 110 is positioned between the light source 104 and the support 61, and the emission filter 112 is positioned between the support 61 and the camera lens 102. A transmission detection system is described in further detail in copending, co-owned U.S. patent application Ser. No. 08/127,387, entitled Quantitative Determination of Analytes Using Transmission Photometry, filed Sep. 27, 1993 (Attorney Docket 5435.U.S.01). Circuitry suitable for transmission detection is generally known, although a particular circuit is described in copending, co-owned U.S. patent application Ser. No. 08/127,470, entitled Light Intensity Detection and Measuring Circuit, also filed Sep. 27, 1993 (Attorney Docket 5367.U.S.01). The entire disclosures of both the above-mentioned applications are incorporated herein by reference.

It is contemplated that detection systems could utilize either the transmission or reflectance methods shown in FIGS. 8C and 8D; and either method for presenting successive detection means 60 to the camera. In particular, the detection systems could incorporate the rotating mirror and motor shown in FIG. 8B, or the rotating heating rings 90, 92 and motor shown in FIG. 5A (with or without the mirror).

5. Computer/Circuit Controls

As shown in FIG. 1, the computer controller 26 may be implemented as an IBM AT-compatible personal computer having a monitor 113, keyboard 114 and data storage means. The computer 26 includes an image frame grabber card 116, a 16-bit analog/digital I/O card 118 and a custom printed circuit board (PCB) 120. A suitable frame grabber card 116 is the Coreco™ OC-300 which is available from Coreco (Montreal, Canada). A suitable analog/digital I/O card 118 is that available from Data Translation Company.

The diagram of FIG. 1 illustrates a simplified representation of the circuitry contained in the frame grabber card 116, I/O card 118 and the PCB 120. The frame grabber card 116 accepts video signals from the camera 100 for processing and analysis. The I/O card 118 and the PCB 120 combine to control the heating and cooling cycles by controlling the heating strips 95, 96 and the fan 19. The PCB 120 contains conventional circuitry which is used to deliver the appropriate power to the heating strips 95, 96 and the fan 19, and also to monitor the actual temperature of the heating strips 95, 96. A pair of thermistors 122, 123 are coupled to the heating rings 90, 92 to sense the temperature of the rings 90, 92. The thermistors 122, 123 generate an output signal representing the temperature of the rings 90, 92, and this signal is fed back to the PCB 120.

The computer 26 includes software programs that control the temperature of the heating rings 90, 92 by controlling the heating strips 95, 96 and the fan 19. The computer 26 also includes software programs for grabbing and analyzing the video signal input at the frame grabber card 116. FIGS. 9A to 9K illustrate a flow chart of a suitable heat control program 200. FIGS. 11A to 11D illustrate a flow chart of a suitable video processing program 600. The heat control program 200 and the video processing program 600 may be implemented using commercially available programming languages such as BASIC or C.

6. Heat Control a. Hardware

In general, the heat control program 200 provides instructions to the PCB 120 via the I/O card 118. For example, the heat control program 200, which communicates with digital signals, sets a desired "set" temperature for the upper and lower heating rings 90, 92. The I/O card 118 converts the digital computer signals into analog signals at the D/A converters 126, 128. One D/A converter is provided for each heating strip and thus, when two heating blocks are employed, the temperature of each may be controlled separately. The analog output from D/A converter 126 is coupled to the upper heating tier 17 via comparator 130 and solid state relay 132, and the analog output from D/A converter 128 is coupled to the lower heating tier 18 via comparator 134 and solid state relay 136.

The output from one relay 132 is coupled to the upper heating strip 95 which is coupled the upper heating ring 90. The output from another relay 136 is coupled to the lower heating strip 96 which is coupled to the lower heating ring 92. The relays 132, 136 enable power to the heating strips 95, 96 which in turn deliver heat to the heating rings 90, 92. Thermistors 122, 123 are coupled to the heating rings 90, 92 for sensing the temperature of the heating rings 90, 92 and developing electric signals corresponding to the sensed temperature. The signals from thermistor 122 are coupled through an operational amplifier 138 to comparator 130, and the signals from the other thermistor 123 are coupled through an operational amplifier 140 to comparator 134. The outputs from the operational amplifiers 138, 140 are also fed to A/D converters 142, 144 on the I/O card 118 to provide the computer 26 and the heat control software with digital signals representing the current temperatures of the upper heating ring 90 and the lower heating ring 92.

The computer 26 generates a digital signal representing the desired or "set" temperature for each tier. These are accepted by the PCB 120 at the D/A converters 126, 128 and converted to analog signals to control the heating strips 95, 96 in order to achieve these set temperatures. Comparators 130, 134 continuously compare the voltages on its two input lines. For comparator 130, the input voltages correspond to the upper heating ring 90 temperature (from thermistor 122) and the set temperature received from the D/A converter 126. For comparator 134, the input voltages correspond to the lower heating ring 92 temperature (from thermistor 123) and the set temperature received from the D/A converter 128. When the sensed temperature of either of the heating rings 90, 92 is less than its set temperature, the corresponding comparator, 130 or 134, continues to output the set temperature to the heating strips 95, 96 via the relays 132, 136. When the sensed temperatures of the heating rings 90, 92 exceed the set temperatures, the comparators 130, 134 cut off the output to the heating strips 95, 96. The program may then direct the PCB via solid state relay 137 to turn on the fan motor 19, and conversely, to turn it off when the cooling period is complete; i.e. when the low set temperature is reached.

b. Software

The flow chart illustrated in FIGS. 9A to 9K uses conventional block symbols to represent the major functions performed by the heat control program. The heat control program 200 has four major sections or routines. The first section is the "Initialize" section 202, shown in FIG. 9A, which gets the computer hardware ready to receive data by defining software variables and fixed hardware parameters in a conventional manner. The initialize section 202 is executed once when the computer 26 is powered up. The second section is the "Edit" section 204, shown in FIGS. 9B to 9D, which allows the operator to set and/or alter the different parameter choices that define the particular denature protocol, if any, and Cycle/Superheat protocol, if any. The third section is the "Denature" section 206, shown in FIGS. 9E to 9G, which instructs the PCB 120 to take the heating rings 90, 92 to the temperature chosen for the denature protocol. The fourth section is the "Cycle/Superheat" section 208, shown in FIGS. 9H to 9K, which instructs the PCB 120 to take the heating rings 90, 92 to the temperatures chosen for the cycling protocols and the superheat, or threshold, protocol. As described earlier in this disclosure, the superheat protocol expands the propellant 40 in the reaction chamber 30 to thereby transfer the reaction sample 38 from the reaction chamber 30 to the detection chamber 32. The program 200 preferably repeats the high and low temperature cycling for a predetermined number of cycles X and then moves to the superheating cycle.

Figure 9A:
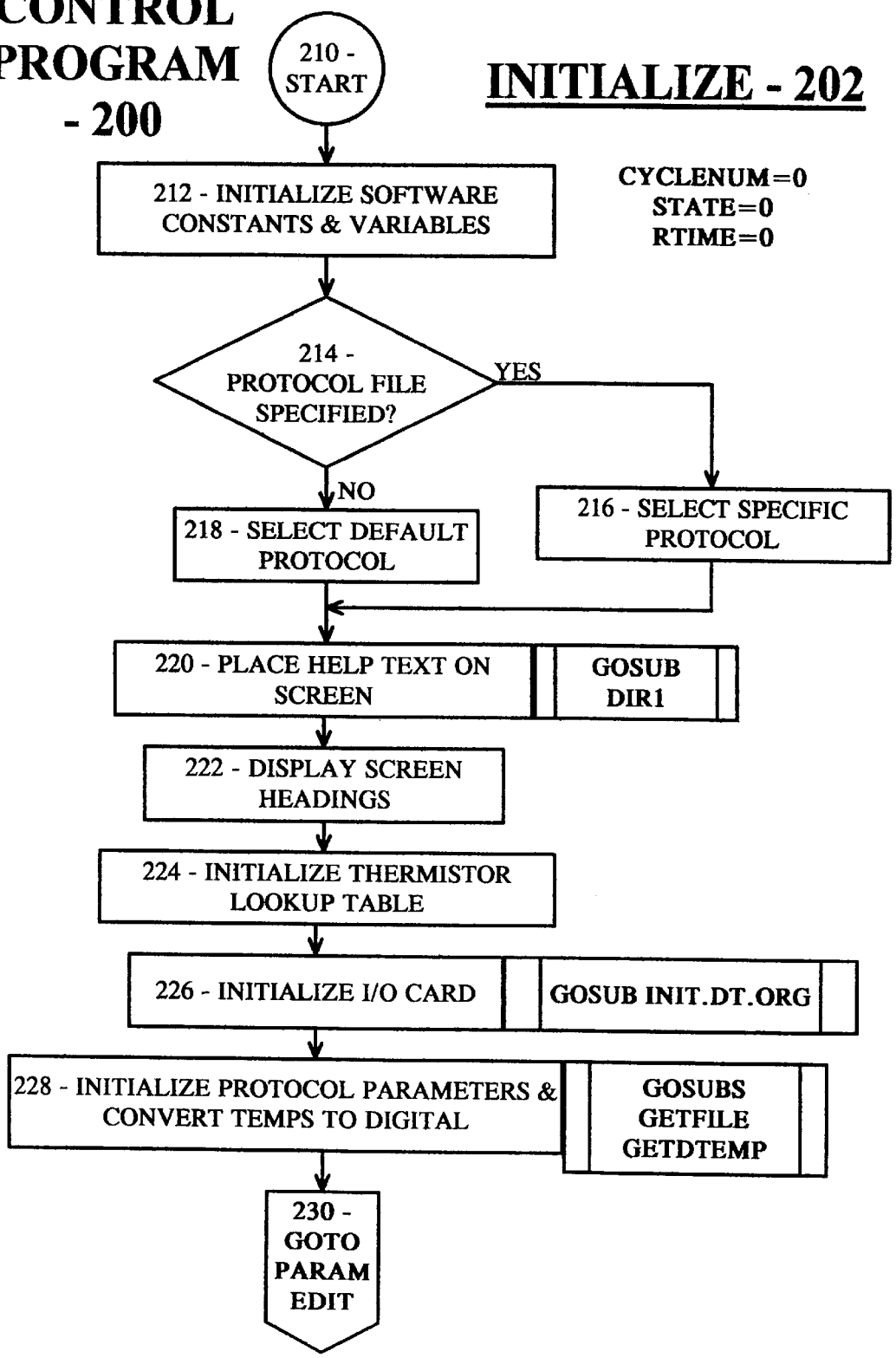
FIGS. 9A to 9K are flow charts illustrating a control program for controlling the heating elements of a two-part thermal cycler according to the invention.

As shown in FIG. 9A, the Initialize section 202 starts the program 200 at block 210 and then initializes the software constants and variables at block 212. Block 212 performs such conventional steps as allocating and defining memory locations on the computer hardware and defining program variables. These steps are necessary in order to allow a computer program to communicate efficiently with the computer hardware. At blocks 214, 216 and 218, the program 200 allows the operator to either specify a desired protocol file (stored in computer memory or data storage) or to accept a set of default protocol values. The protocol file contains values for a set of parameters that define the characteristics of a particular cycling/superheat protocol. In either event, the protocol parameters may be altered by the operator in the Edit section 204 described below. For the disclosed embodiment of the heat control program 200, the following parameters are included in the protocol file, and exemplary values are given in the far right column. In the disclosed program 200 the Shutoff Temperature (which is used only at the end of the operation to turn the fan off) is not an editable parameter, but is preset.

| Param. Name | Description | Example Value |
|---|---|---|
| TEMP.DEN = | Denature Temperature | 95° C. |
| TIME.DEN = | Denature Time | 120 sec |
| TEMPLO = | Low Cycle Temperature | 60° C. |
| TIMELO = | Low Cycle Time | 60 sec |
| TEMPHI = | High Cycle Temperature | 80° C. |
| TIMEHI = | High Cycle Time | 60 sec |
| TIMELEAD = | Lead Time For Superheat | 15 sec |
| TIMESUPER = | Overall Superheat Time | 30 sec |
| TEMPSUPER2 = | Upper Block Superheat Temperature | 95° C. |
| TEMPSUPER = | Lower Block Superheat Temperature | 110° C. |
| CYCLEMAX = | Total Number Of Cycles | 8 |
| TRACK = | Tracking (on/off) | off |
| SHUTOFF = | Shutoff Temperature At End Of Reaction | 50° C. |
| TIMEIMAGE = | Image Delay Time | 120 sec |

Figure 10:
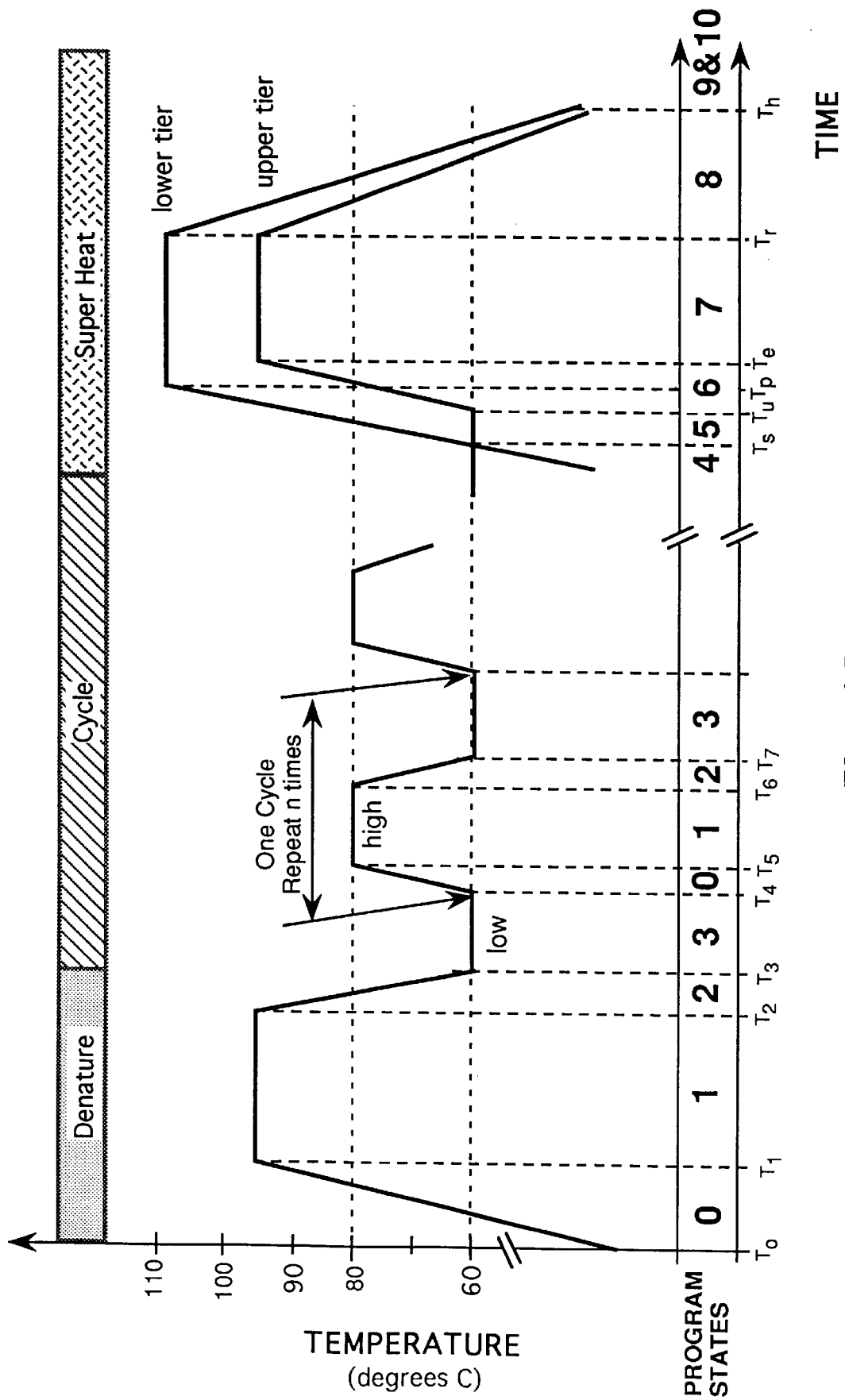
FIG. 10 illustrates a time and temperature profile for various aspects of the system of FIG. 1.
Figure 11A:
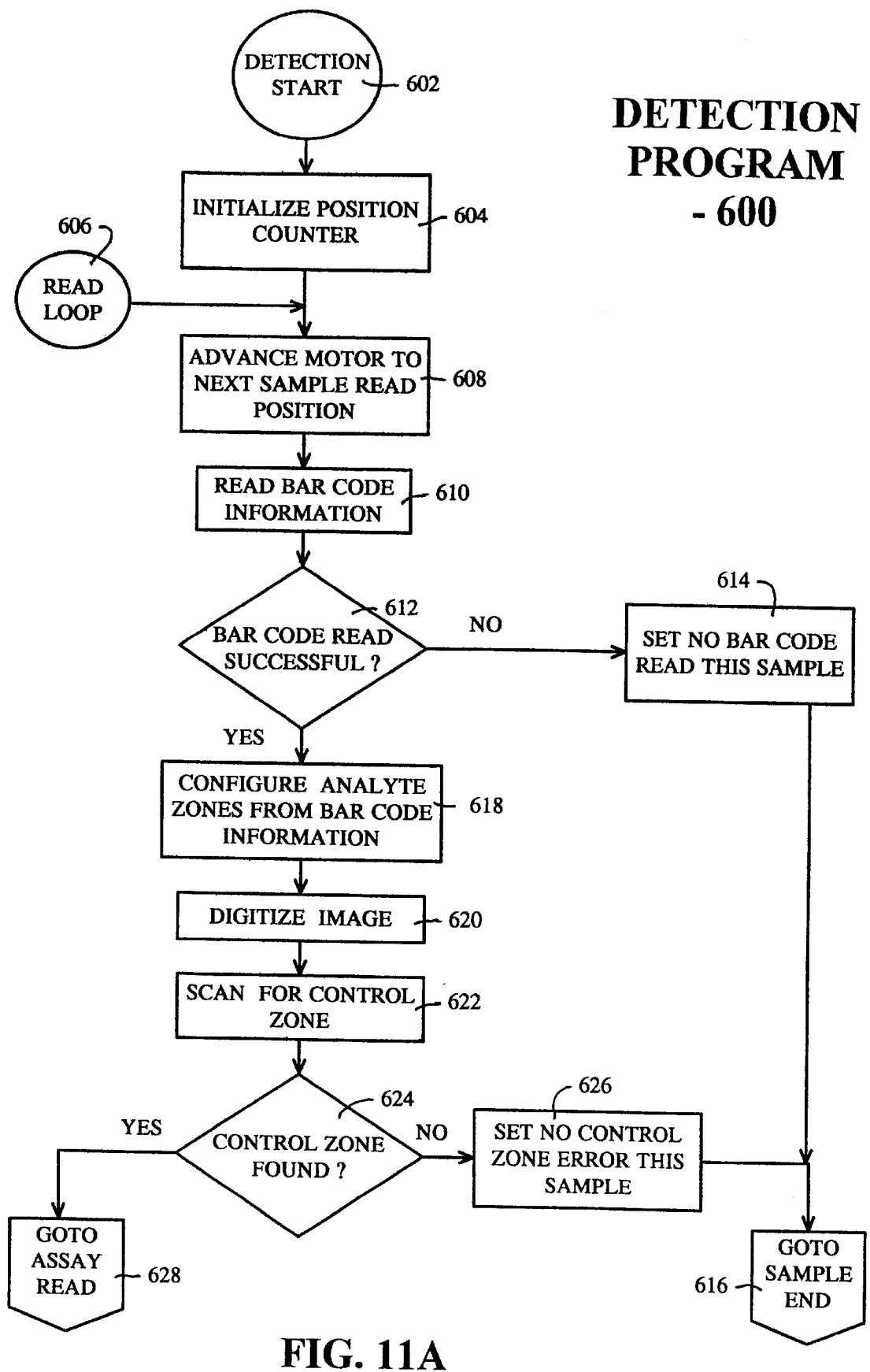
FIGS. 11A to 11D are flow charts illustrating a computer program for processing a video image according to the invention.
Figure 11B:
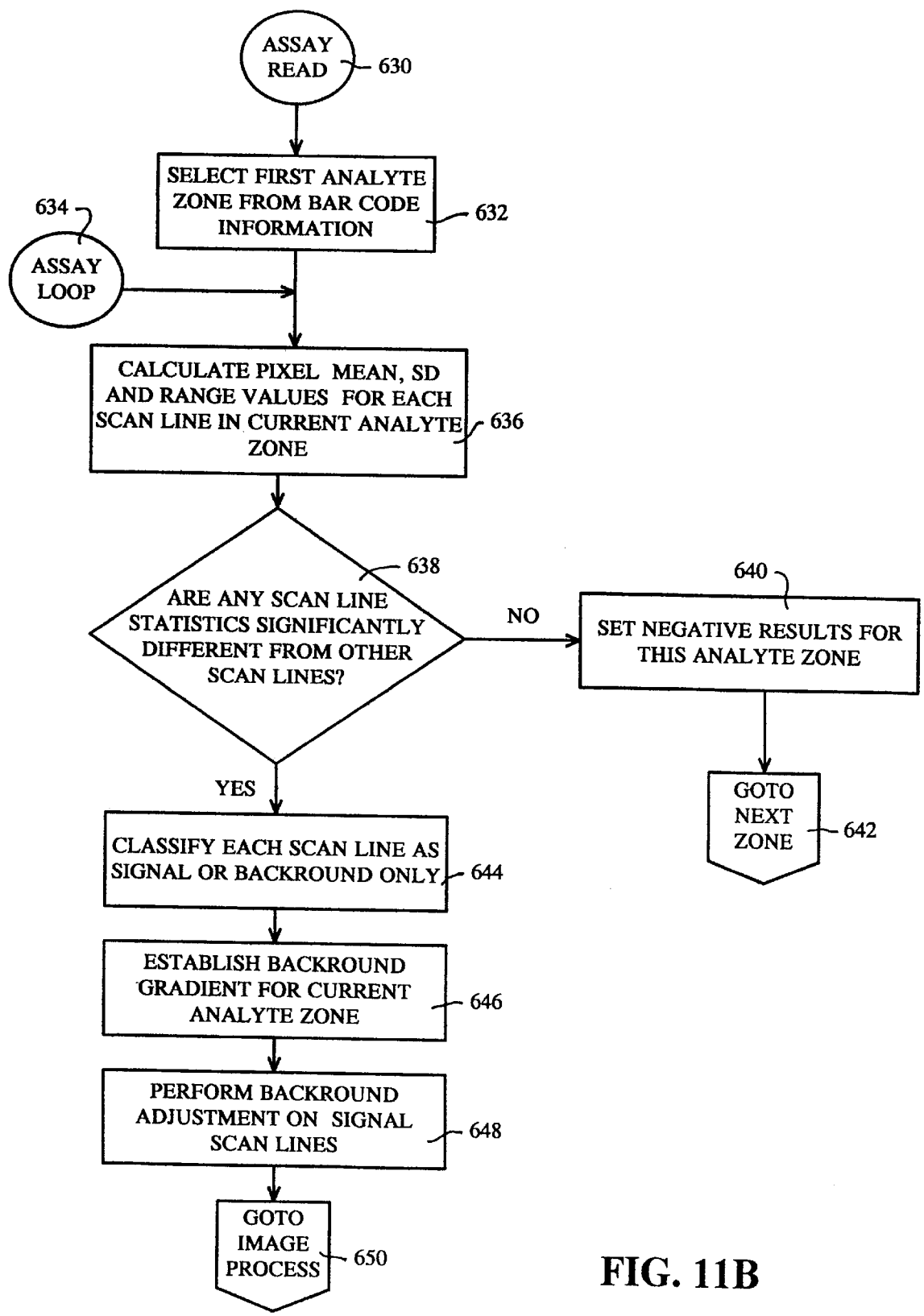
Figure 11C:
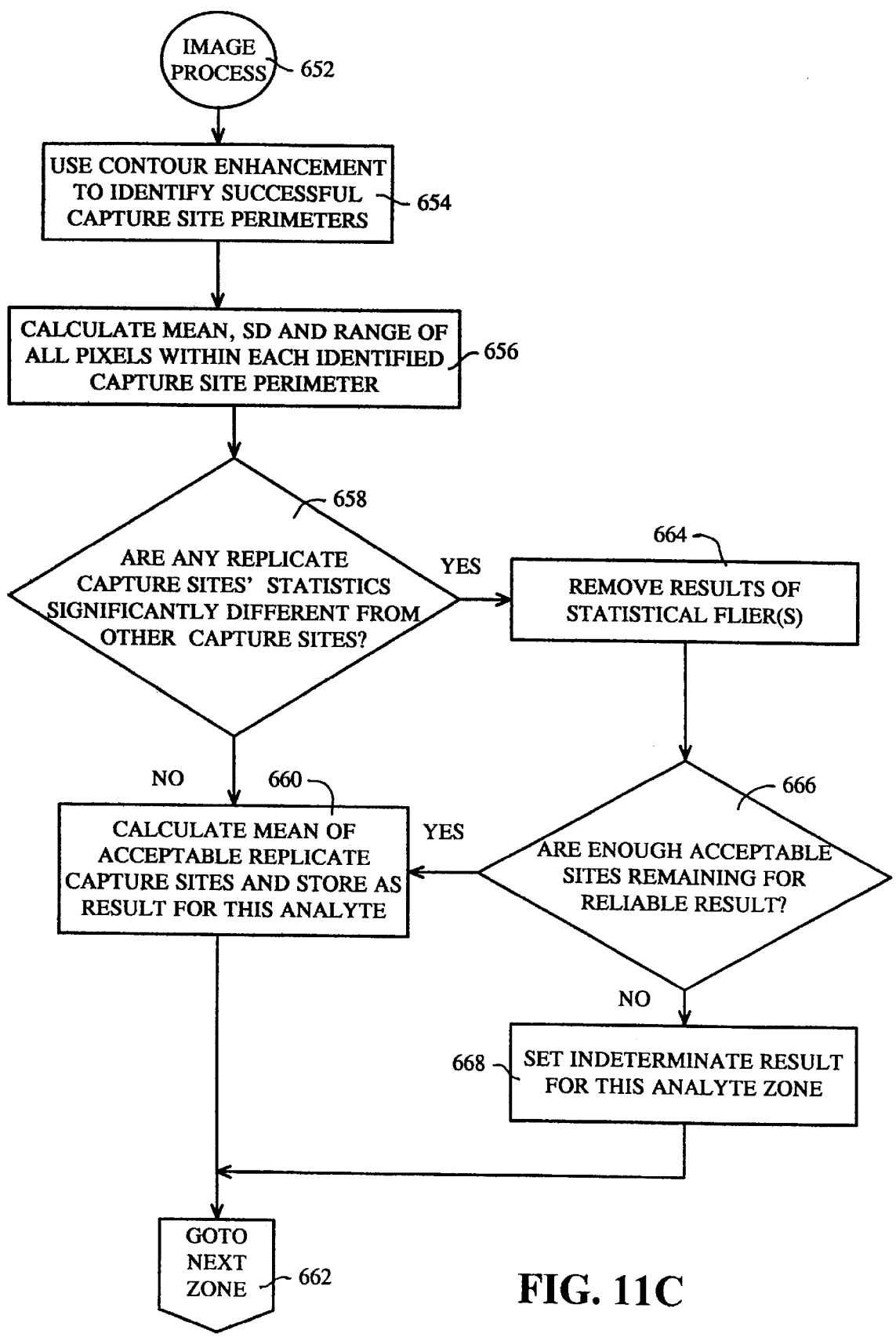
Figure 11D:
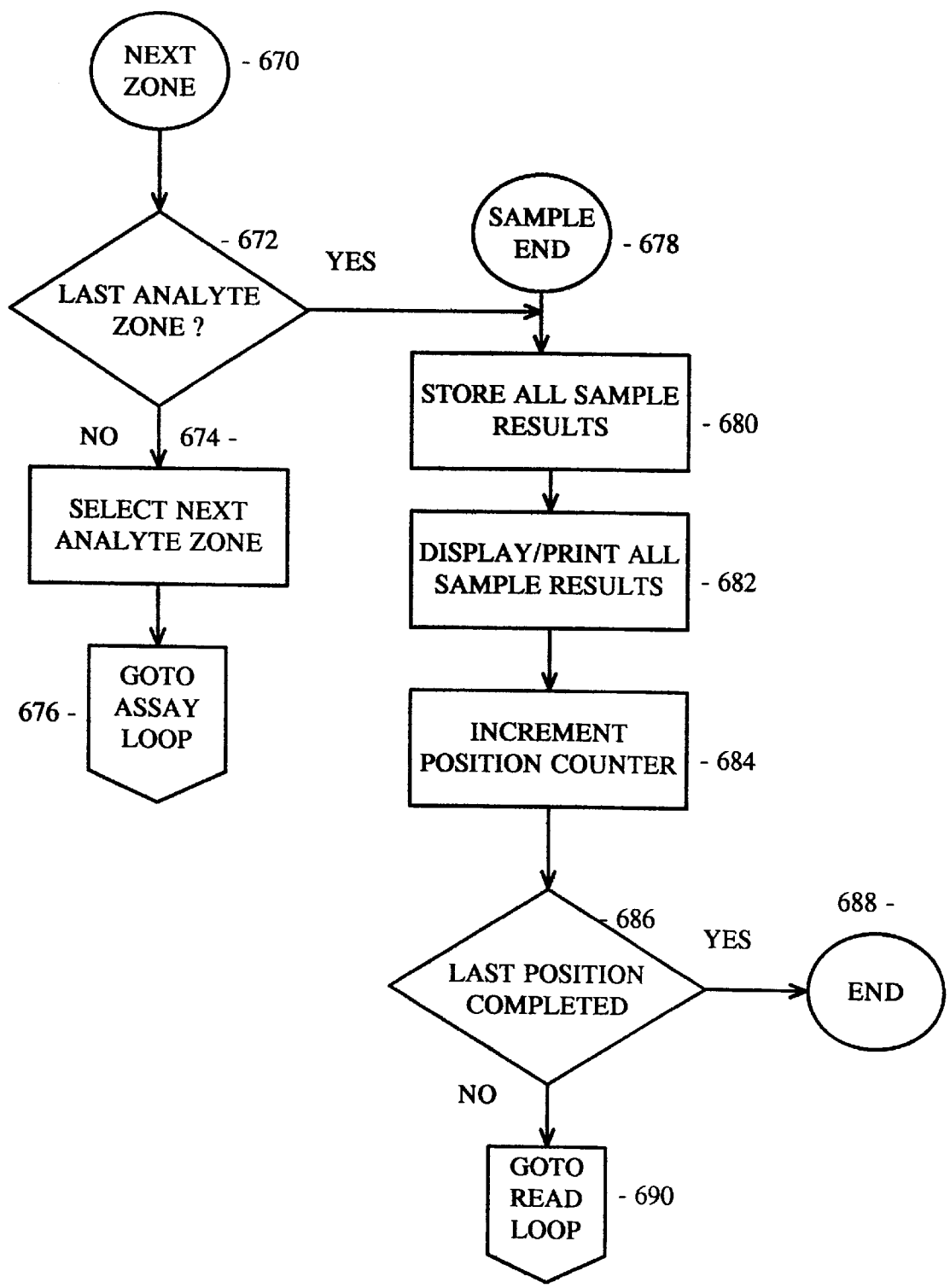

The parameters will be described with reference to FIG. 10, which is a plot of temperature vs. time for the heating ring(s) (and consequently the reaction chamber 30) as they are taken through a denature protocol, a cycling protocol and a superheat protocol. FIG. 10 assumes there are two heating tiers, but that either they parallel one another or only one is in use until the superheat cycle. As shown, the heating ring(s) start at a particular temperature at Time $T_0$. This temperature may be any value at or below the holding temperature from the end of the last amplification reaction. For the illustrated example, the heating ring(s) are about room temperature at $T_0$. After $T_0$, the heat control program 200 instructs the PCB 120 to bring the heating ring(s) to a first "set" temperature, in this case the "Denature Temperature", the value of which is selected for denaturing nucleic acid in the sample and/or any probe or primer reagents. The Denature Temperature typically ranges from about 80–100° C.; the exemplary value is 95° C. As the set temperature cannot be attained instantaneously, the temperature gradually rises or "ramps" up to the set temperature during the period from $T_0$ to $T_1$. Via feedback thermistor(s) the program 200 senses when the heating ring(s) have reached the selected set temperature and holds this temperature for the predetermined period from $T_1$ to $T_2$ (the "Denature Time") in order to denature the sample DNA and any reagent probes or primers.

At the conclusion of the Denature Time ($T_2$) the program resets the set temperature to the "Low Cycling Temperature" and the heating ring(s) "ramp" down to this new set temperature during the period from $T_2$ to $T_3$, which is maintained for the "Low Cycling Time". Preferably the ramp down times (e.g. $T_2$ to $T_3$ and $T_6$ to $T_7$) are minimized by turning on the fan 19 to help cool the heating ring(s). The values for these parameters are selected to provide the temperature and time for reannealing primers or probes to the suspected target or amplicons made from target. Annealing temperatures depend on probe length and the content of guanosine and cytosine residues, as is known in the art, and are typically set several degrees below the predicted $T_m$ for the probes or primers. For typical probe and primer lengths, Low Cycling Temperatures can range from about 45–70° C.; the exemplary value being set at 60° C. This period is shown in FIG. 10 from $T_3$ to $T_4$.

Next, the program resets the set temperature and ramps up to the "High Cycling Temperature" which is held for the "High Cycling Time" as shown in FIG. 10 from $T_4$ to $T_5$ and $T_5$ to $T_6$. Values for the High Cycling Temperature and High Cycling Time are selected to again denature the probes or primers from the target or amplicons. Generally the High Cycling Temperature is slightly lower than the sample Denature Temperature, but it must be greater than the Tm of the amplicons. Values ranging from about 70–95° C. are common; the exemplary value is 80° C.

After the High Cycle Time has expired, the program resets the set temperature to the "Low Cycling Temperature", the heating ring(s) "ramp" down to $T_7$ and the process repeats. Each cycle consists of a high and a low temperature, as shown in FIG. 10. "Total Number of Cycles" is the parameter whose value controls the number of cycles. The number of cycles will vary greatly depending on the assay being performed. For both PCR and LCR, it is not uncommon to have between 10 and 70 cycles, generally between 25 and 50.

After the Total Number of Cycles has been achieved, the program moves into the Superheat aspect to transfer the reaction sample 38 from the reaction chamber 30 to the detection chamber 32 as described above in connection with FIGS. 5A–5E. In two tier systems, this is generally accomplished by superheating the lower tier first and the upper tier second for reasons described above. Optionally, the lower tier is also superheated to a higher temperature than the upper tier as shown in FIG. 10. The Lower Block Superheat Temperature and the Upper Block Superheat Temperature are the parameters that hold the values for these superheat stages. As mentioned earlier, these values are selected to expand a propellant, thereby forcing the reaction sample into the detection chamber. This temperature is generally as high or higher than the denature temperature, but it need not be since the propellant can be shielded from the denaturing temperatures by placing it low in the reaction chamber (i.e. within the lower tier) and not tracking the two tiers. For simplicity, an aqueous reaction sample may serve as propellant and the superheat temperatures will generally range from about 90–120° C.

In two tier systems, the "Lead Time For Superheat" is an optional time period during which the lower heating ring 92 is brought to its superheat temperature before the upper heating ring 90 is brought to its superheat temperature. The Lead Time For Superheat is shown in FIG. 10 from $T_s$ to $T_u$. An exemplary value is given above as 15 seconds. Depending on the value for Lead Time and the slope of the superheat ramp-up, the Lead Time ($T_s$ to $T_u$) may be greater than, equal to or less than the ramp time ($T_s$ to $T_p$); in other words, the relative positions of $T_u$ and $T_p$ may be reversed from that depicted.

The "Overall Superheat Time" holds the time value for the superheat stage, commencing when the upper tier (or the single tier if only one is used) reaches its set temperature (e.g. the Upper Block Superheat Temperature). This time is shown in FIG. 10 from $T_e$ to $T_r$ and needs only be sufficiently long to transfer an adequate volume of the reaction sample to the detection chamber. This of course is dependent on the sample volume and the detection means, but is easily determinable by simple experiment. An exemplary value is 30 seconds. It should be noted, however, that all exemplary times and time ranges are subject to the specific embodiments utilized herein and that the use of other ranges is easily within the ability of those skilled in the art The "Tracking" parameter determines in the case of a two tier heating element whether both the upper and the lower heating rings 90, 92 participate in the denature protocol and the cycling protocols. If the Tracking parameter is on, both heating rings 90, 92 participate in the denature protocol and the cycling protocols. If the Tracking parameter is off, only one of the heating rings 90, 92 participates in the denature protocol and the cycling protocols.

The "Shutoff Temperature At The End Of The Reaction" is the set temperature at which the program 200 turns off the fan motor that cools the heating rings 90, 92 at the end of the testing protocol, represented in FIG. 10 by $T_h$.

The "Image Delay Time" merely signals the computer to wait a specified time before beginning the detection procedures. This time should be sufficient to permit the signal in the detection chamber to fully develop, and may range from about 1–10 minutes or more, depending on the type of signal and detection means employed.

It will be appreciated that one may select an amplification protocol that calls for a high cycle temperature before the first low cycle temperature. In this case, the period from $T_2$ to $T_3$ is simply expanded to include a plateau at the high cycling temperature for a time determined by the selected protocol before continuing its ramp down to the low temperature.

FIG. 10 also shows the Program States for the Denature and Cycle/Superheat routines. These are described below in connection with the software.

Returning again to FIG. 9A, after the protocol file is selected (blocks 214, 216 and 218), the program 200 then places a help text and the current protocol parameters on the monitor 113 screen at blocks 220 and 222. Block 220 provides help information to assist operators in deciding what steps to take to continue the program 200. The screen headings at block 222 also provide prompts regarding keystroke entries to obtain a desired result.

The program 200 initializes a thermistor look-up table at block 224. Although the resistance of the thermistors 122, 123 varies with temperature, these temperature changes are not linear. Thus, a look-up table is provided so that the program 200 does not have to recalculate the temperature every time a reading is delivered from either of the thermistors 122, 123. The I/O card 118 is initialized at block 226. This sets the various values that will be used on the I/O card 118 such as the gain settings on the pre-amp stages or the use of unipolar (0 volts to 10 volts) or bipolar (−5 volts to +5 volts) signal ranges. At block 228, the protocol parameters are initialized and the I/O card 118 is prepared to convert temperatures to digital. Block 230 moves the program 200 to the Edit section 204.

Figure 9B:
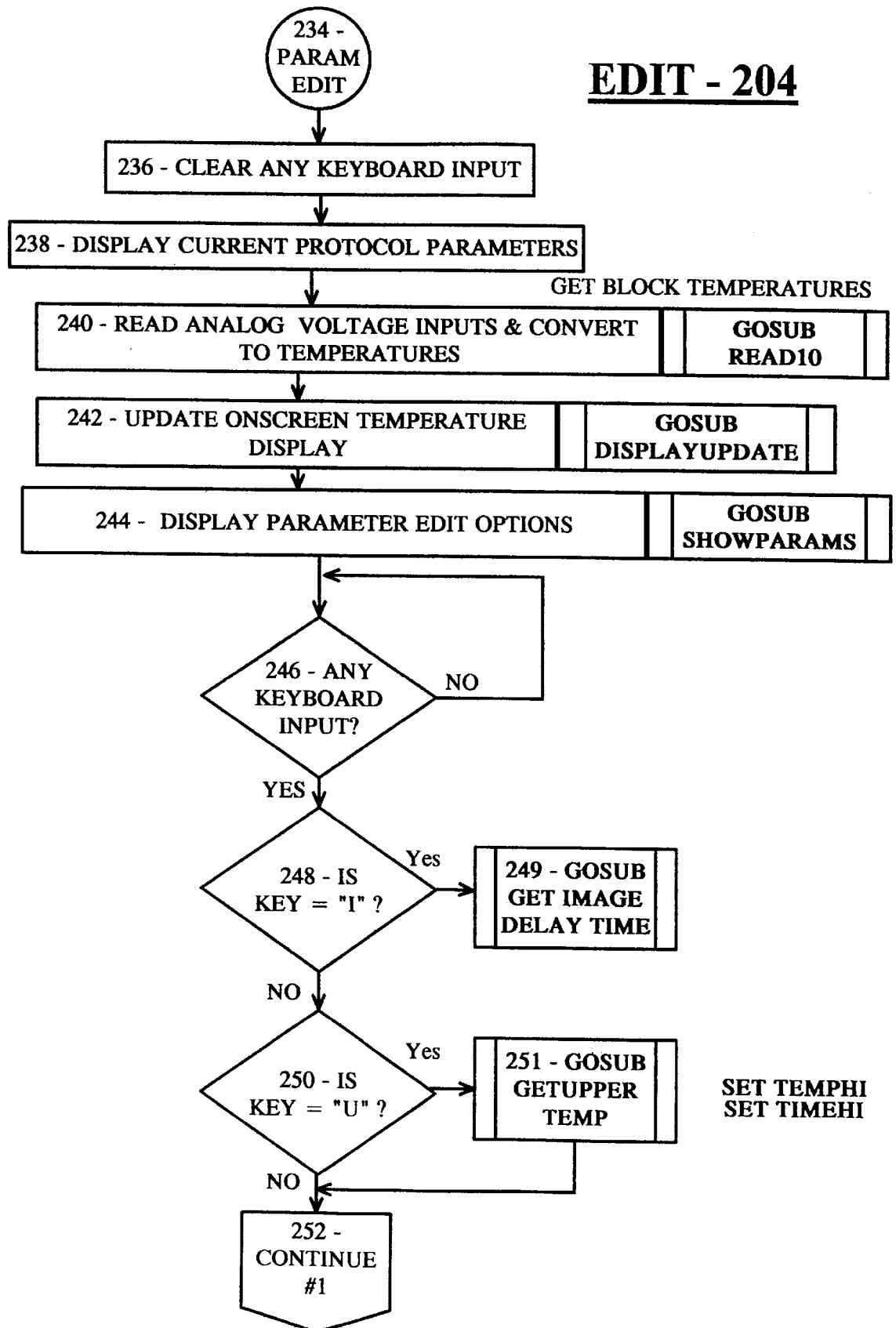
Figure 9C:
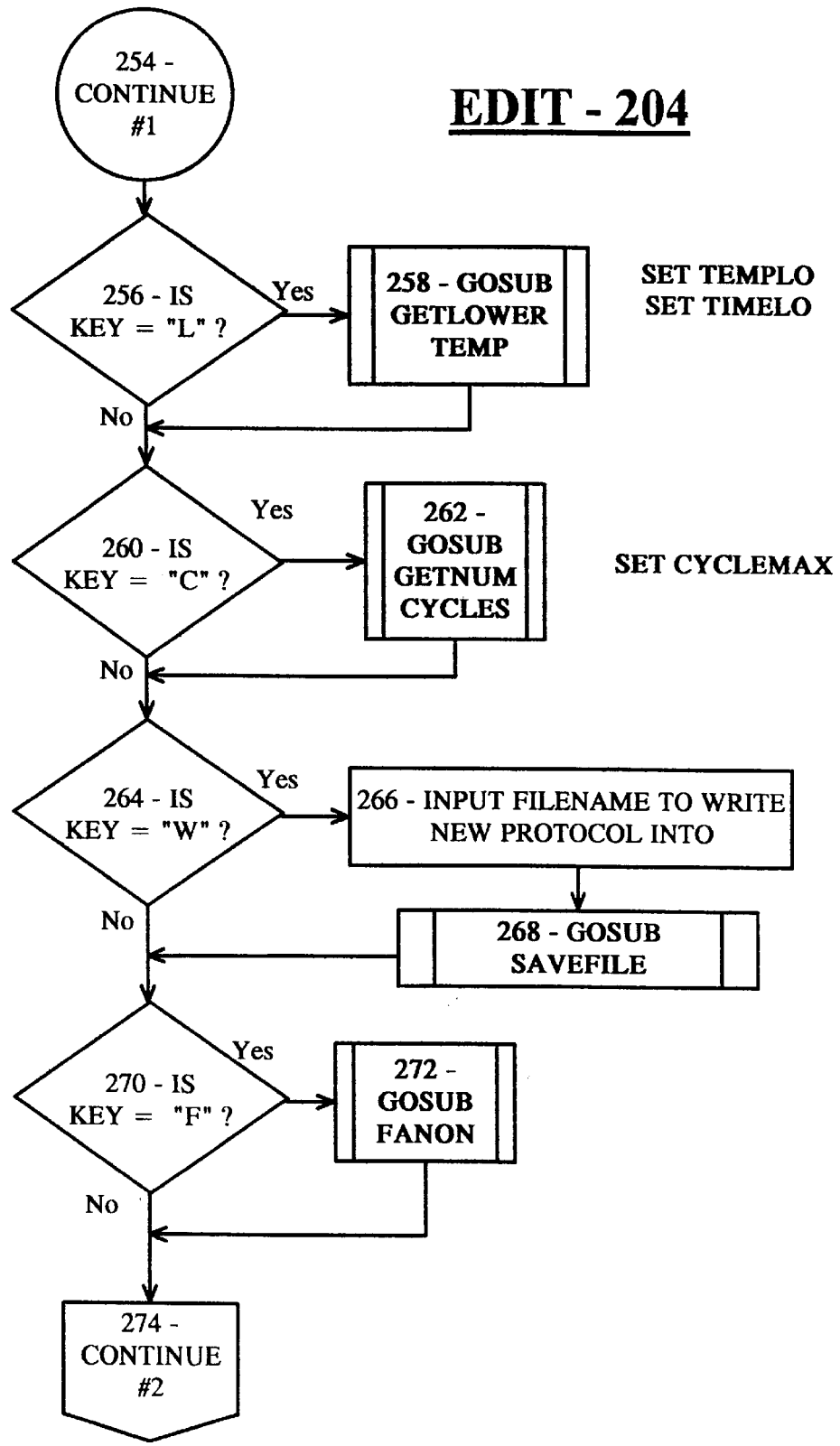
Figure 9D:
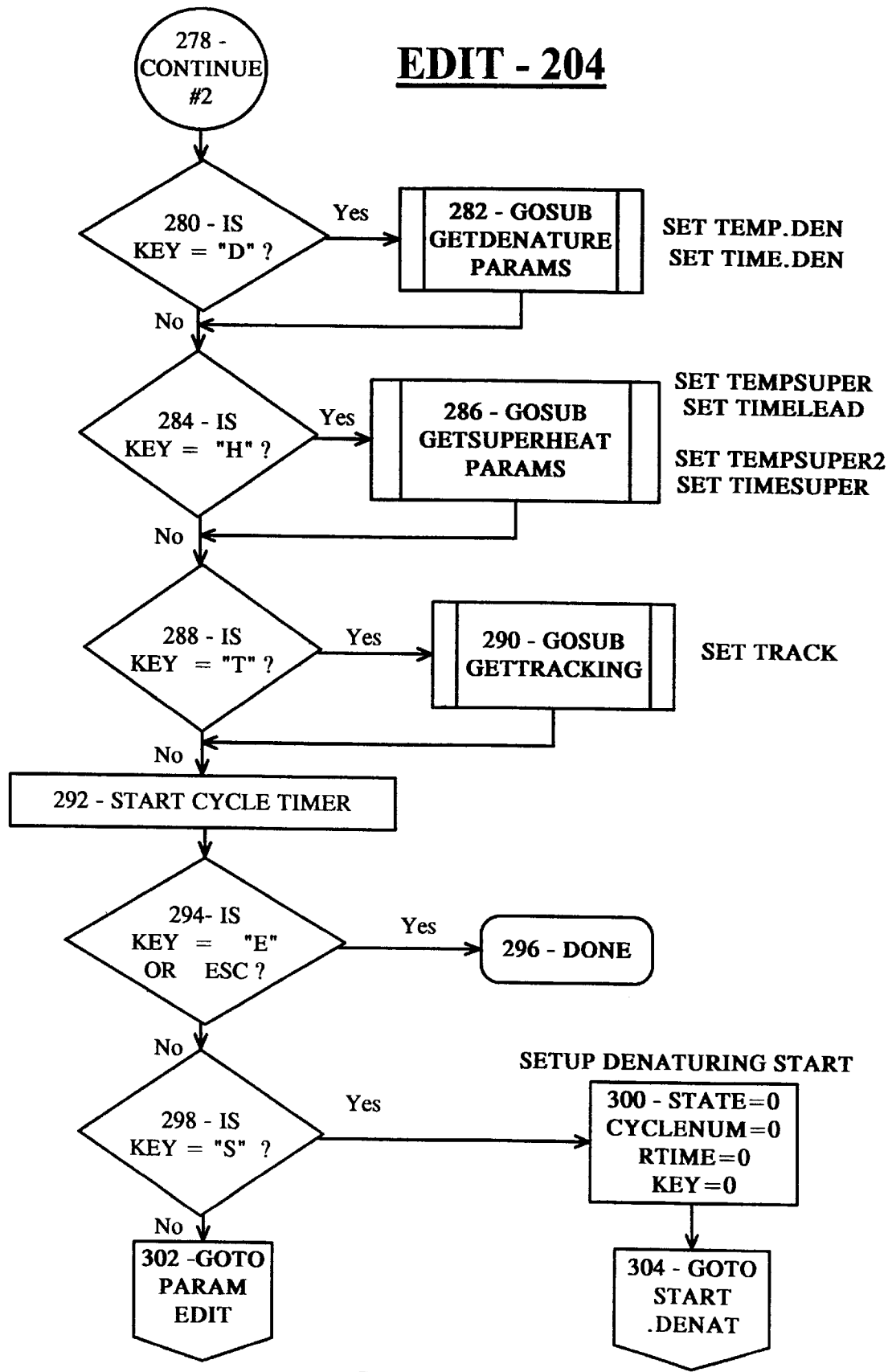
Figure 9E:
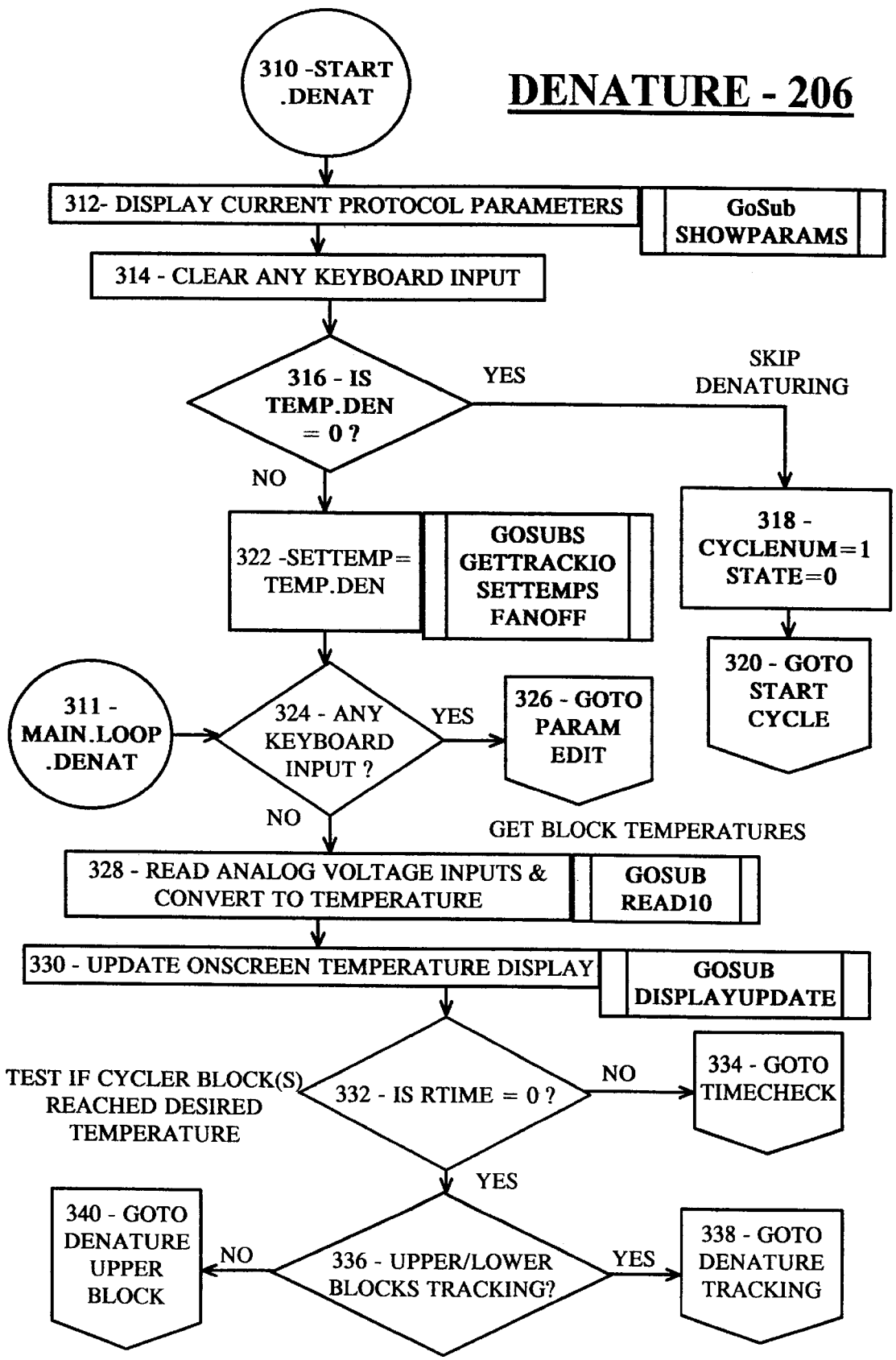
Figure 9F:
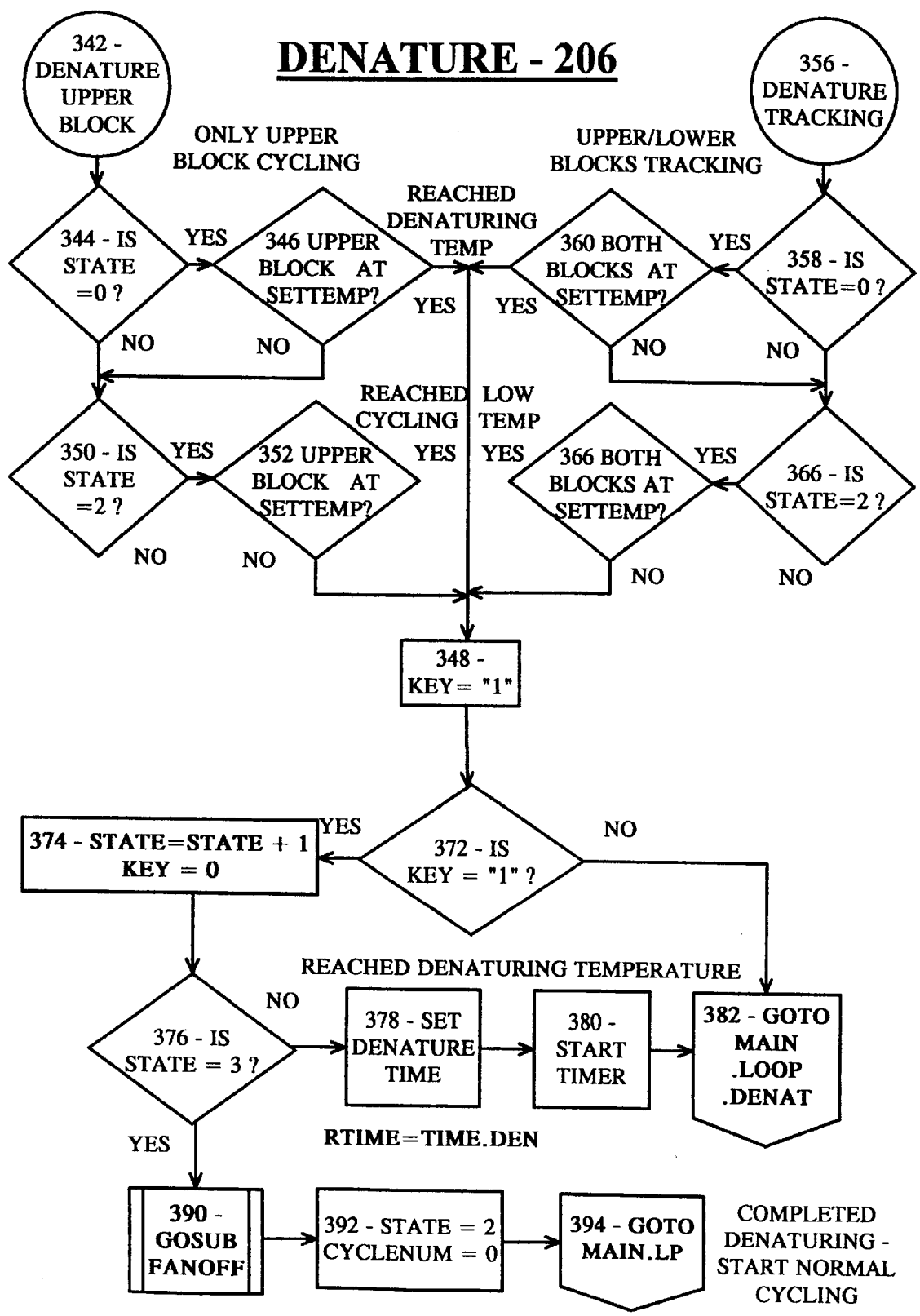
Figure 9G:
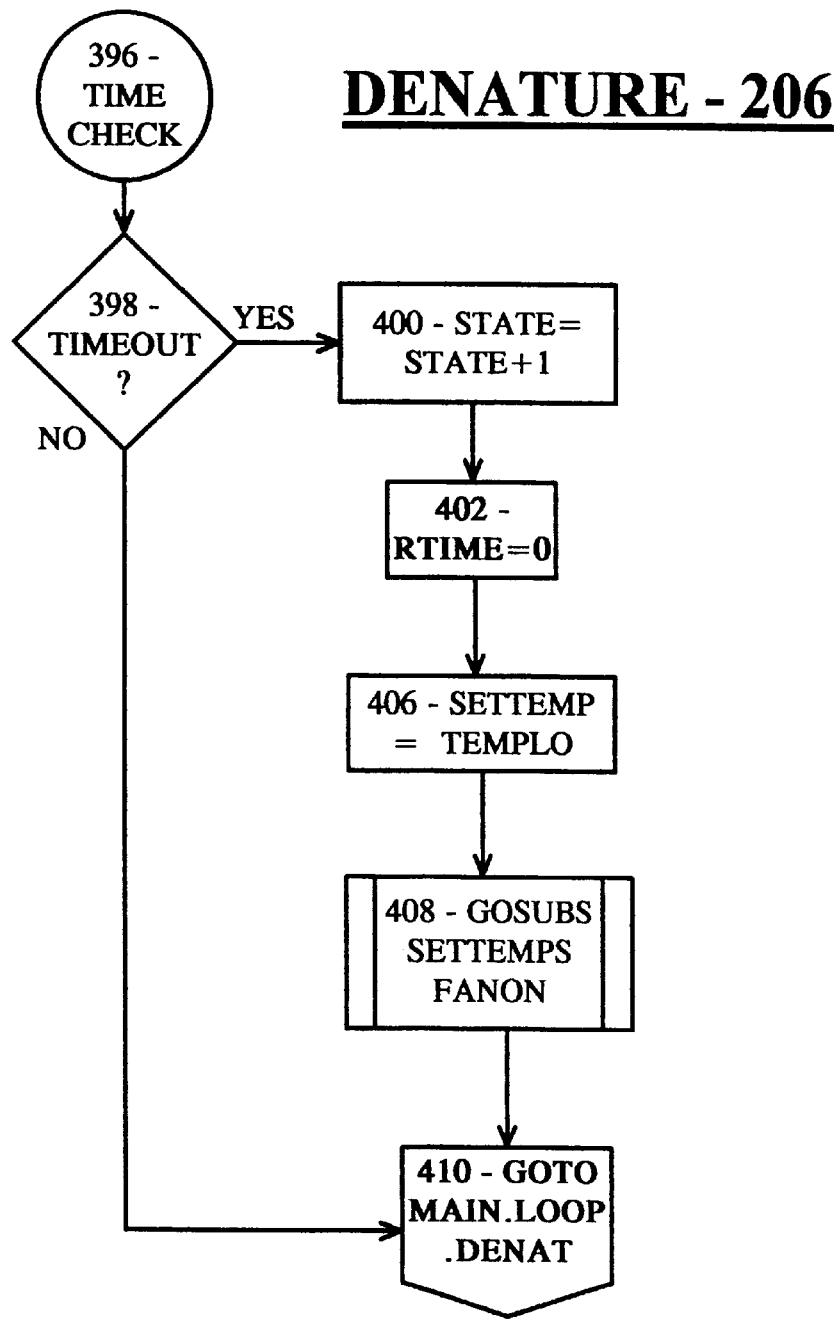
Figure 9H:
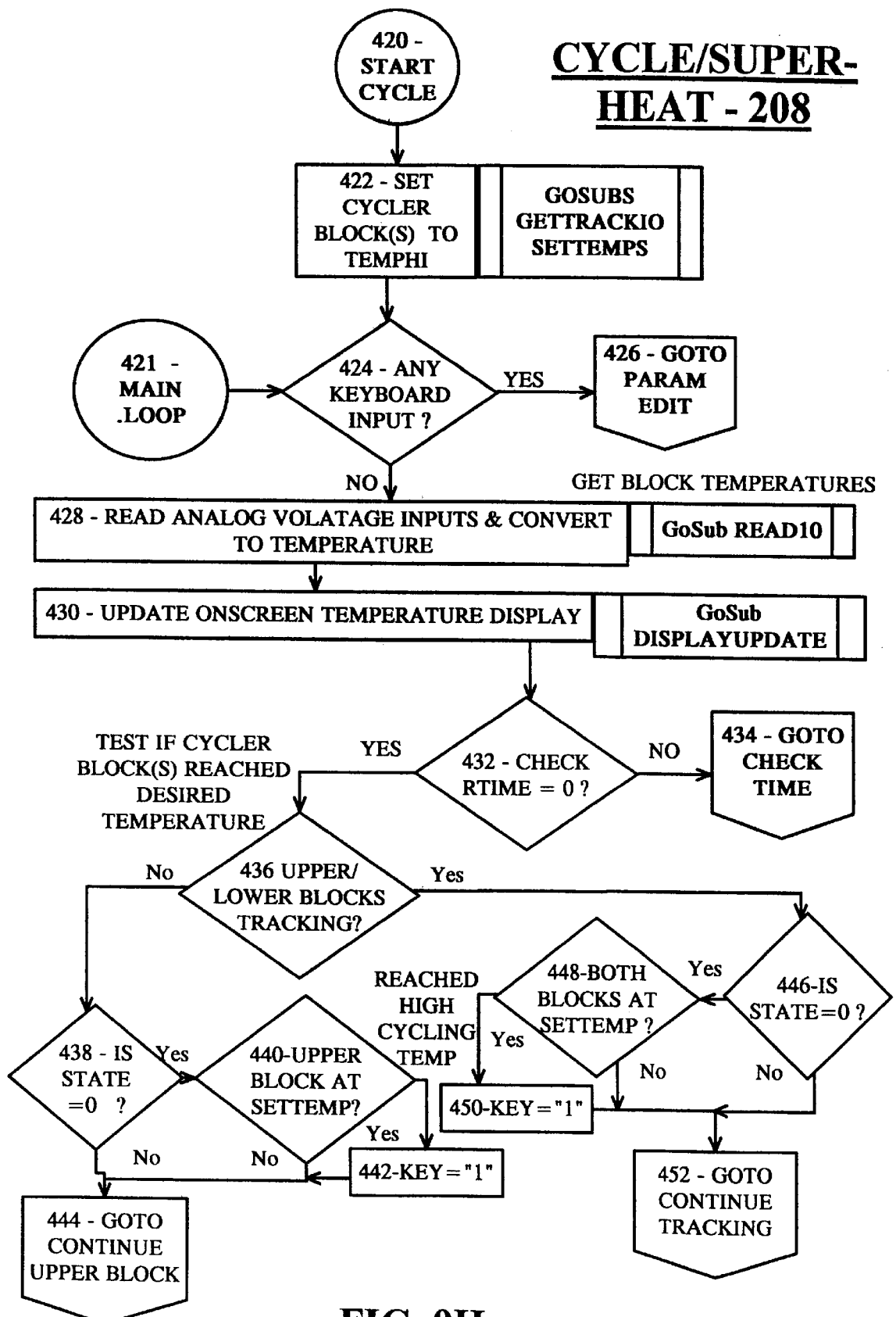
Figure 9I:
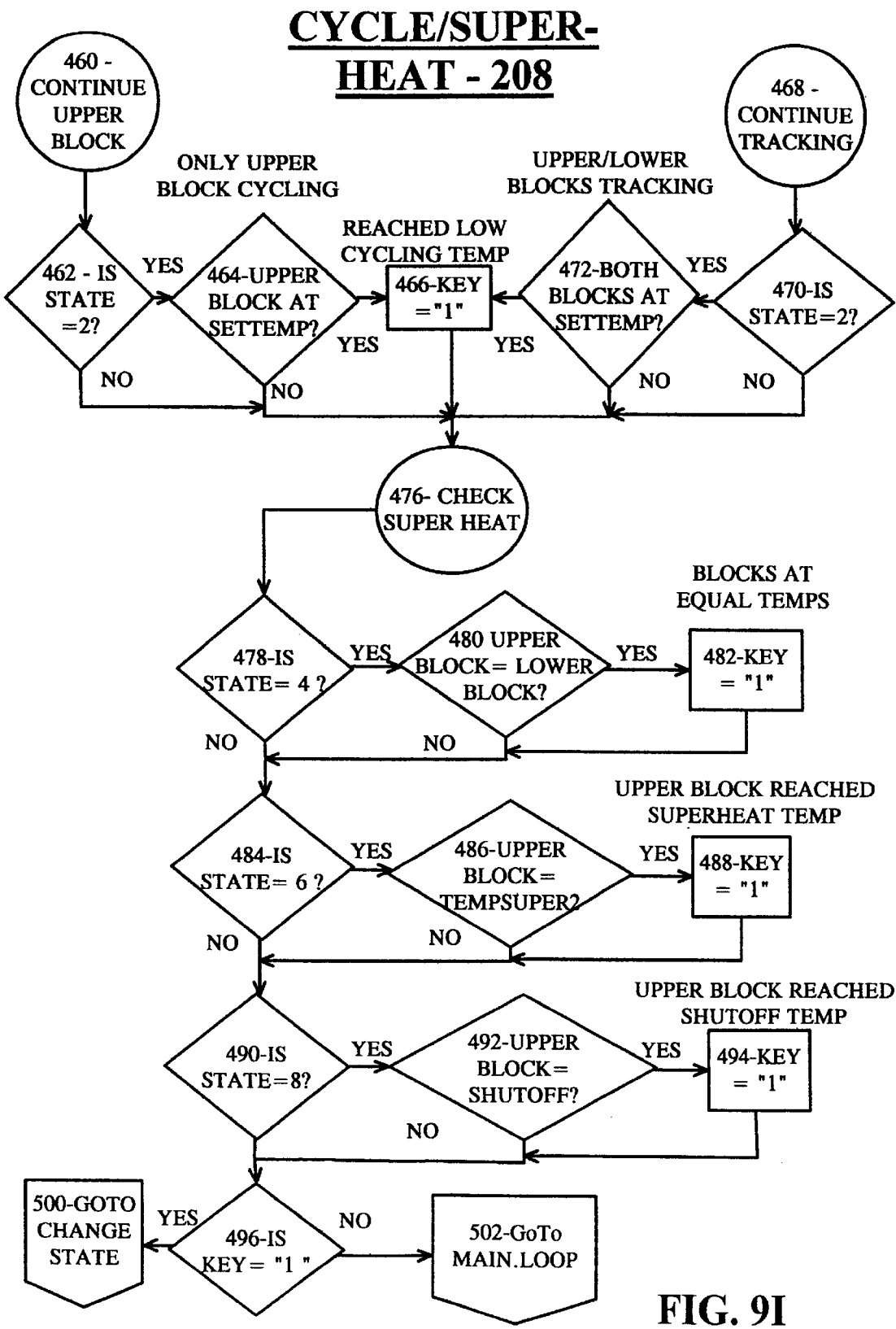
Figure 9J:
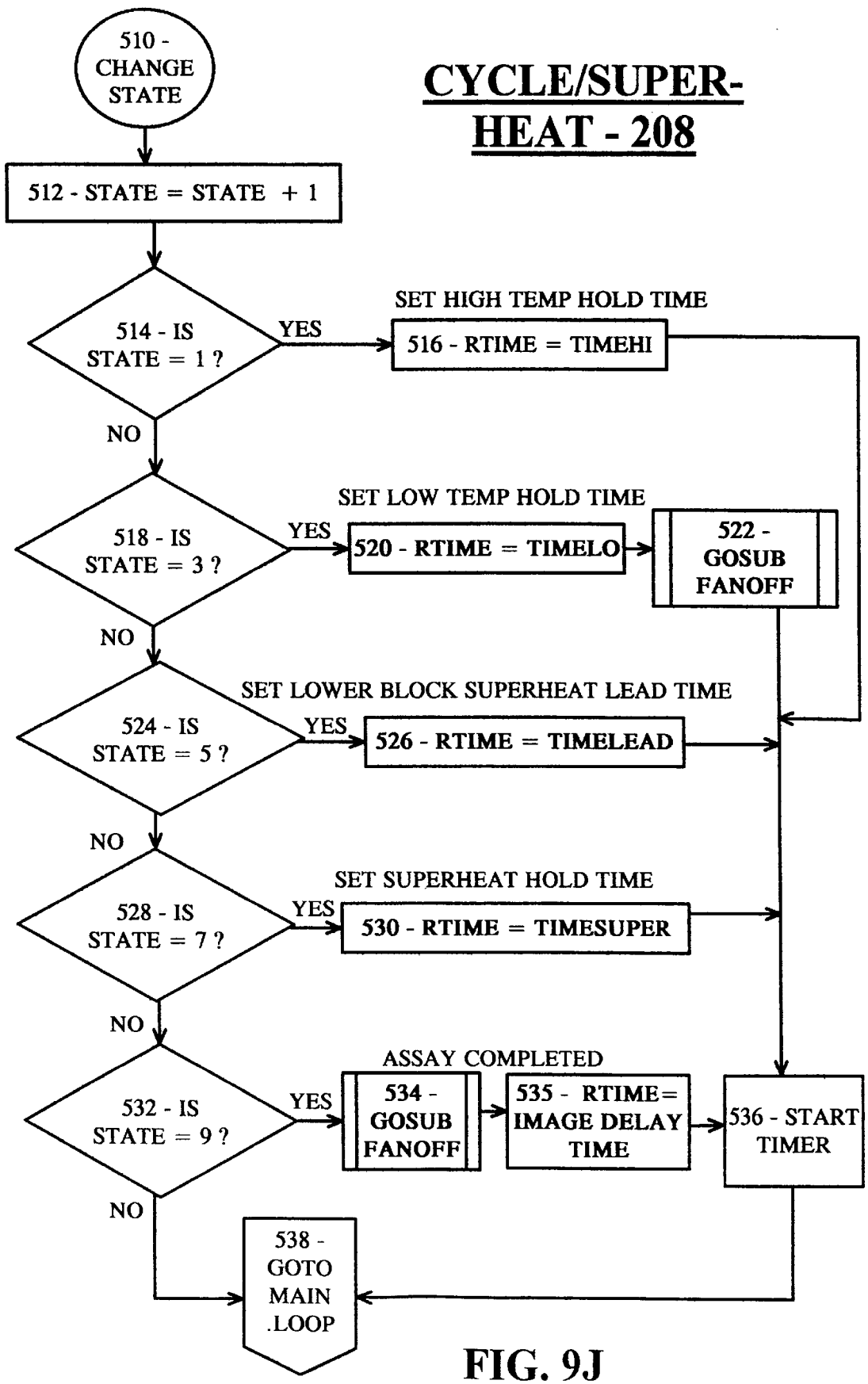
Figure 9K:
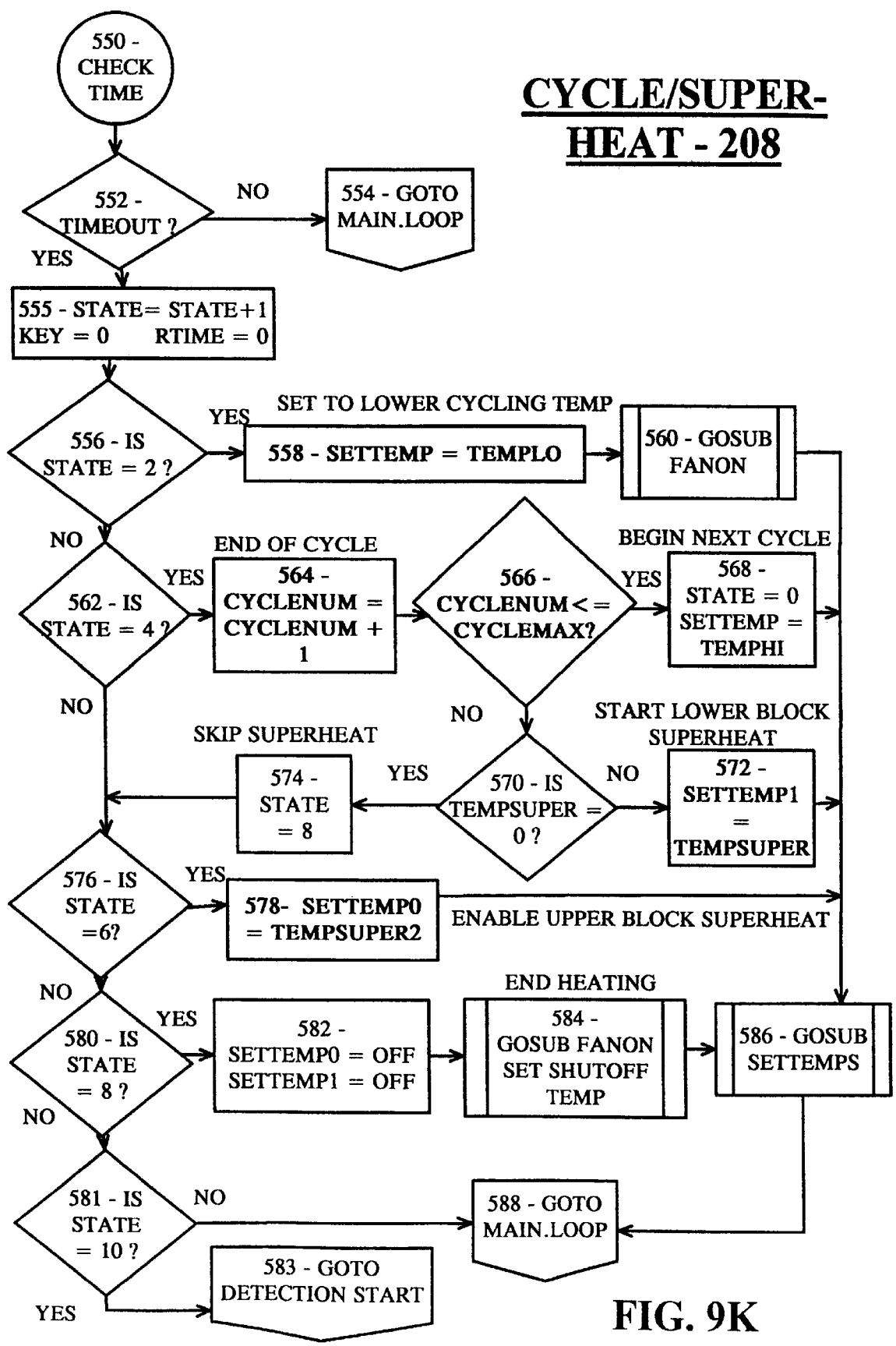

The Edit section 204 of the program 200 is shown in FIGS. 9B, 9C and 9D. In general, the Edit section 204 allows the operator to change some or all of the protocol parameters chosen at blocks 216 and 218 of the Initialize section 202. The Edit section 204 clears the keyboard 114 at block 236, which is equivalent to setting Key=0, and displays the current protocol parameters at block 238. The program 200 provides a continuous display of the current temperature of the heating rings 90, 92. This is accomplished at blocks 240 and 242 by reading the analog inputs from the upper and lower heating rings 90, 92, converting these inputs into temperature values at the thermistor look-up table, and displaying the temperature on the monitor 113. In block 244, the program 200 also displays on the monitor 113 the parameter edit command instructions which provide prompts to the operator for editing the protocol parameters.

The Edit section 204 then looks for a keyboard input at block 246 until one is received. The operator may now edit protocol parameters by hitting any of the keys shown in blocks 250, 256, 260, 264, 270, 280, 284, 288, 294 and 298. The "U" key, shown at block 250, takes the program 200 to block 251 which allows the operator to reset the high cycling temperature and the time duration of the high cycling temperature. Similarly, the "L" key, shown at block 256, takes the program 200 to block 258 which allows the operator to reset the low cycling temperature and the time duration of the low cycling temperature. The "C" key, shown at block 260, takes the program 200 to block 262 which allows the operator to set the maximum number of cycles. The "W" key, shown at block 264, takes the program 200 to blocks 266 and 268 which allow the operator to save the edited parameter protocols in a file in the computer's memory. The "F" key, shown at block 270, takes the program 200 to block 272 which allows the operator to turn on the fan 94 and thereby bring down the temperature of the heating rings 90, 92, if desired. The "D" key, shown at block 280, takes the program 200 to block 282 which allows the operator to edit the denature temperature and the time duration of the denature protocol. The "H" key, shown at block 284, takes the program 200 to block 286 which allows the operator to edit the superheat parameters. The superheat parameters include the superheat temperature for the lower heating ring, the lag-time for superheating the upper heating ring, the superheat temperature of the upper heating ring, and the overall time period for the superheating. The "T" key, shown at block 288, takes the program 200 to block 290 which allows the operator to edit the tracking parameter. After the program 200 polls the T key at block 288, the timers are set at block 292 in anticipation of starting the Denature section 206. The "E" key, shown at block 294, takes the program 200 to block 296 which exits the program 200. The "S" key, shown at block 298, sets the "state," "cycle number", "RTime" and "key" all to 0 (block 300), and moves the program 200 to the Denature section 206 from block 304. If the S key is not pressed, the program 200 returns to the beginning of the Edit section 204.

The Denature section 206 (FIGS. 9E, 9F and 9G) begins at block 310 and displays the current protocol parameters at block 312. Block 314 clears the keyboard inputs, and block 316 examines the value that was entered for the denature temperature (TEMP.DEN). If the denature temperature has been set to 0, the program 200 skips the denature protocol and sets the "cyclenum" flag to 1 and the state flag to 0 (block 318) before moving into the Cycle/Superheat routine via block 320. By entering the Cycle/Superheat section 208 via block 420, the program starts the sample out at the High Cycling Temperature by setting SETTEMP equal to TEMPHI at block 422 and by entering the Cycle/Superheat routine 208 with the state flag at 0.

However, using the example value above, the Denature temperature is set to a value greater than zero (95° C.), so the program 200 initializes the Denature temperature and Denature time at block 322 which includes several subroutines for getting the tracking information, setting the Denature temperature and turning the fan 94 off. "Setting" a temperature or a time involves creating a variable such as SETTEMP, SETTEMP0 or SETTEMP1 for temperature, and RTIME for time, and assigning a value to said variable the value being selected from one of the parameters described above: namely, TEMP.DEN, TEMPLO, TEMPHI, TEMPSUPER and TEMPSUPER2 for temperature variables and TIMB.DEN, TIMELO, TIMEHI, TIMELEAD and TIMESUPER for the time variable. Thus, at block 322, the SETTEMP variable assumes the value stored in the protocol for the Denature Temperature.

Blocks 311, 324 and 326 show that Denature section 206 continuously polls the keyboard 114 for parameter edit inputs from the operator. If a keyboard input is received, the program 200 moves to the Edit section 204, and the operator can then edit any of the current protocol parameters. The program 200 updates the temperature display at blocks 328 and 330.

At block 332 the program 200 branches to poll either temperature or time depending on the value of the program state flag, the key flag and the RTime. Since RTime (as well as other variables) was set to 0 at block 300, the program polls temperature on this first pass through the loop and moves on to block 336. Here, the program 200 examines the TRACK variable to determine if both blocks of a two tier system should be cycled in parallel or not If TRACK=on, block 338 sends the program to block 356 which examines both blocks. If TRACK=off, block 340 causes the program to examine only one block the upper block in this example. For the remainder of this description, is will be assumed that TRACK=off, but one skilled in the art will readily recognize the mirror-like nature of certain sections of the flow diagrams. Of course, in a single heating element system, the TRACK variable is unnecessary and only one block is examined. The following description assumes a two block system wherein the upper block only is used for denaturing and cycling, it being understood that this is just one embodiment.

In the Denature section 206, the program state flag can have four values from 0 to 3. In general, when the program state flag is 0 (see block 344), the program 200 has signaled the PCB 120 to take the heating rings to the denature temperature, and the program 200 (at block 332) polls the A/D converters 142, 144 on the I/O card 118 to determine when the upper heating ring has reached the denature temperature (see block 346). If the upper heating ring has not yet reached the denature temperature, the program 200 moves through blocks 350, 372 and 382, and returns to the main denature loop near the beginning at block 311. From there, the program returns to block 346 and again inquires as to whether the upper heating ring has reached the denature temperature (95° C.).

The program 200 continues this loop until the upper heating ring 90 has reached the denature temperature. The answer at block 346 is now yes, and the program 200 sets the key flag to 1 at block 348. When the heating rings 90, 92 reach the denature temperature, the key flag is set to 1 at block 348, and the program state flag is incremented to 1 at block 374. In addition, the variable RTime is set to assume the value of parameter TIME.DEN (Denature Time) at block 378, the timer is started at block 380 and the program returns to the main denature loop (blocks 382 and 311).

Because RTime now holds a value (120 seconds in the example), the program branches at block 332 to the "Timecheck" subroutine at block 396 and inquires if RTime has timed out RTime "times out" when the period set for the particular activity (in this case, the 120 sec. Denature Time) expires. If the answer to this inquiry is no, the program loops back through the beginning of the Denature section 206 and returns via blocks 332 and 334 to the timeout inquiry at block 398. If the answer to the timeout inquiry is yes, then the program 200 increments the program state flag (to 2 now) at block 400 and resets Key and RTime to 0 at block 402. The program 200 then resets the SETTEMP variable to equal the parameter value TEMPLO (block 406) and turns on the fan (block 408) to ramp the heating block 90 down to the Low Cycling Temperature.

Upon return to the Main Denature Loop (block 311) with the program state flag at 2 and RTime reset to 0, the program 200 branches through blocks 336, 340, 342 and 344 to block 350, and again polls the upper heating block 90 at block 352 to determine if it has reached the SETTEMP (now the Low Cycling temperature). If the upper heating block 90 has not yet reached its set temperature (60° C. in the example), the program 200 loops back to block 352 through blocks 372, 382, 311, 332, 336, 340, 342, 344 and 350. When the Low Cycling SETTEMP is reached, the program increments the Key to 1 and the state flag to 3 (blocks 348 and 374) and turns the fan off (block 390). Then it resets Key to 1 and the state flag to 2 before moving into the main loop of the Cycle/Superheat section 208 (blocks 392 and 394). It should be appreciated that when entering the Cycle/Superheat routine 208 after the denaturing routine, the Cycle/Superheat routine begins at the Low Cycling Temperature, whereas when Denaturingis skipped the program enters the Cycle/Superheat routine at the High Cycling Temperature (see blocks 318, 320, 420 and 422 as described above).

In the example the Cycle/Superheat section 208 (FIGS. 9H to 9K) begins at block 421, the SETTEMP having already been initialized. As with the Denature section 206, the Cycle/Superheat section 208 also continuously polls the keyboard 114 for parameter edits inputs, and returns the program 200 to the Edit section 204 whenever it receives the appropriate input from the keyboard 114. The current temperature of each of the heating blocks 90, 92 is fed to the I/O card 118 and displayed at blocks 428 and 430.

At block 432, the program 200 asks whether it should check time or temperature depending on the value of RTime. The RTime is 0 here (having been reset last at block 402), so the program branches to block 436 to check the temperature of the heating blocks. Tracking is off, so the inquiry at block 436 leads to the state inquiry at block 438 and then to the state inquiry at block 462. In the Cycle/Superheat section 208, the program state flag can have eleven values from 0 to 10, but was set to 2 leaving the Denature Section (block 392), thus the program asks at block 464 whether the upper heating block has reached the Low Cycling temperature of 60° C. Since this temperature was reached at the end of the Denature section 206, (and even if it had not been, block 392 reset Key=1) and thus Key=1 at this point. The program 200 then flows through blocks 476 478,484 and 490 to the inquiry at block 496, which is "yes" at this point, causing the program to move into a "Change State" subroutine.

It can be observed generally that in this program 200 when the program state is zero or an even number the heating block(s) is ramping up or down to a new set temperature and the program branches to poll the A/D converter(s) 142, 144 on the I/O card 118 for temperature information fed from the themiistor(s) 122, 123. Conversely, when the program state is an odd number the set temperature has been reached so the program branches to poll the timer so that it can determine if the heater block(s) have held the set temperature for the appropriate time period. This can be seen in FIG. 10 also.

In the Change State subroutine at block 510, the program state flag is incremented (to 3) at block 512. Block 514 is answered no and block 518 is answered yes, causing the program 200 to reset RTime to assume the value of TIMELO (the Low Cycling Time of 60 seconds in our example) at block 520. The program also turns the fan off at block 522 and starts the timer at block 536 before moving back to the beginning of the Cycle/Superheat section 208 at block 421.

The program 200 moves through the beginning of the Cycle/Superheat section to block 432. Because the RTime now holds a value (60 sec), the program branches from block 432 to the Checktime subroutine beginning at block 550. If the RTime has not expired, the program returns to the main loop until the 60 seconds in the RTime has timed out. When the RTime has timed out, the answer to the inquiry at block 552 is yes, and thus the program 200 increments the state flag to 4 at block 555 and resets RTime and Key to 0 before moving on to block 562 via block 556.

When the program reaches state 4 and block 562, the cyclenum flag is incremented at block 564 (to 1 in our example since the Cycle/Superheat routine 208 was entered via blocks 392 and 394, where cyclenum was set=0). The program then queries the "cyclenum" flag. If the cyclenum flag has not exceeded the maximum number of cycles, stored as protocol parameter CYCLEMAX, the program 200 resets the program state flag to 0 and sets the variable SETTEMP to the value of the High Cycle Temperature parameter and turns the heating element(s) on for beginning the next cycle (blocks 568 and 586) and then returns to the main loop at block 421. For the illustrated example, CYCLEMAX is 8 and TEMPHI is 80° C. Thus, the program returns to block 421 with SETTEMP=80.

This time through the main loop, the program moves through blocks 424,428 and 430 to the RTime test at block 432. Since RTime was reset to 0 at block 555, the program branches to block 436 to check the temperature of the heating block(s). With Tracking off, the inquiry at block 436 leads to the state inquiry at block 438, where the answer is now yes. This sends the program to block 440 to determine if the heating block(s) has reached the new set temperature. If not, the program moves through blocks 444, 460, 462, 476, 478, 484, 490 and 496 to return to the main loop and continue its polling of the heater block temperature. When the heating block(s) reach the set temperature the answer at block 440 increments the key flag to 1 at block 442. Continuing through blocks 444, 460, 462, 476, 478, 484 and 490 to block 496, the program branches over to the "Change State" subroutine because Key=1.

In the Change State subroutine at block 510, the program state flag is incremented (to 1) at block 512 and block 514 is answered yes, causing the program 200 to reset RTime to assume the value of TIMEHI (the High Cycling Tune of 60 seconds in our example) at block 516. The program also starts the timer at block 536 before moving back to the beginning of the Cycle/Superheat section 208 at block 421. The program 200 moves through the beginning of the Cycle/Superheat section 208 to block 432. Because the RTime now holds a value (60 sec), the program branches from block 432 to the Checktime subroutine beginning at block 550. If the RTime has not expired, the program returns to the main loop (block 554) until the 60 seconds in the RTime has timed out. When the RTime has timed out, the answer to the inquiry at block 552 becomes yes, and thus the program 200 increments the state flag to 2 at block 555 and resets RTime and Key to 0 before moving on to block 556.

At block 556 the answer is yes causing the program to reset the variable SETTEMP to the value of the Low Cycle Temperature parameter (TEMPLO) at block 558 and at block 560 turns on the fan for cooling the heating block(s) before returning to the main loop at block 421.

Once again in the main loop, the program reached block 432 and decides to poll the temperature (block 464) since RTime is 0. This continues until the desired (TEMPLO) temperature is reached, upon which key is set to 1 at block 466. This sends the program back to the "Change State" subroutine (block 510) where the state flag is incremented (to 3) and RTime is reset to TIMELO for holding the heating block(s) at TEMPLO for the desired time period. This causes the program to branch at block 432 to the Checktime subroutine (block 550) to poll the timer. As before, when RTime times out, the state flag is incremented at block 555 (to 4), RTime and Key are reset to 0 and the cyclenum flag is again evaluated. The program 200 continues to execute cycles as described above using program states 0, 1, 2 and 3 until CYCLEMAX is reached (e.g. until the cyclenum flag is incremented to 9 at block 564).

When the cyclenum flag exceeds the maximum number of cycles (block 566), the program 200 examines the value of TEMPSUPER at block 570. If it is 0, the superheat portion is skipped by setting the program state flag to 8 at block 574. In the illustrated example, the value of TEMPSUPER is 110° C., which starts the lower ring superheat process by setting the variable SETTEMP1 equal to 110° C. at block 572 before returning the main loop at 421. SETTEMP1 is a variable that holds a value for the set temperature of the lower block only, whereas SETTEMP was applied to the upper block or to both blocks if Tracking was on.

In the main loop, the program once again polls temperature at block 432 since RTime is 0, and skips through inquiries at 438 and 462 to reach the inquiry at 478, which is answered yes. The program assumes here that if Tracking was off, the lower heating block is at a lower temperature than the upper block and state 4 is maintained until the lower block comes up to the temperature of the upper block. When the inquiry at block 480 is yes, the key flag is set to 1 which causes a state change via blocks 496, 500 and 510. This increments the state flag (to 5) and loads the TIMELEAD value into the variable RTime at block 526 and restarts the timer at block 536 before returning to the main loop. The TIMELEAD value is the time period by which the superheat of the lower heating block 92 leads the superheat of the upper heating block 90. This is represented by the exemplary 15 seconds and in FIG. 10 by the time period between $T_s$ and $T_u$.

The main loop now branches at block 432 to the Checktime subroutine and determines when RTime (=TIMELEAD) times out, whereupon the program 200 increments the state flag (to 6). With state flag=6 the program branches at block 576 to load the value of TEMPSUPER2 into the variable SETTEMP0 at block 578 and to enable superheating of the upper block. SETTEMP0 is a variable that holds a value for the set temperature of the upper block only, as distinct from the lower block or both blocks (as when Tracking is on). Returning to the main loop, the program branches to poll temperatures at block 432 and reaches block 484 and 486 to examine whether the upper block has reached its set temperature (TEMPSUPER2). When it has, the key flag is changed to 1 at block 488 to move the program 200 to the Change State subroutine at block 510. This again increments the program state (to 7) which via block 528 causes the variable RTime to assume the value of TIMESUPER at block 530 and to restart the timer at block 536. In the example TIMESUPER was 30 seconds and represents the period of time during which the upper block is maintained at the superheat temperature. In the main loop, block 432 branches to the Checktime subroutine and determines when the RTime (=TIMESUPER) is allowed to time out. When it does, the program 200 increments the state flag (to 8), resets the key flag and RTime and moves to block 580 where the program turns off the temperature outputs to the upper and lower heating rings at block 582. In preparation for cool down, the program at block 584 turns the fan on and resets the SETTEMP variables for both heating blocks to the value of SHUTOFF. This value, 50° C. in the example, is selected so that the fan will not run constantly trying to cool the heating blocks below ambient temperature.

Upon return to the main loop with the program state at 8 and RTime reset to 0, the program branches at block 432 to poll temperatures. At block 490 the answer is yes so at block 492 the program polls the temperature of the upper block to determine if it has cooled to the set temperature of 50° C. When it has, the key flag is set to 1 at block 494, causing a state change via blocks 496, 500, 510 and 512 to state 9. At block 532 the program branches to turn the fan off (block 534) and to load the value of TIMEIMAGE into the variable RTime (block 535) before starting the timer (block 536) and returning to the main loop. As mentioned, the TIMEIMAGE parameter is selected to allow the unit to compete its development of signal before starting the detection process. In the main loop, block 432 branches to the Check Time subroutine and, upon timeout, increments the state flag (to 10) causing the program via blocks 581 and 583 to begin the detection procedures, described below in connection with FIGS. 11A to 11D.

7. Video Processing

The detection system 22, described in an earlier section, utilizes a video processing program such as the Detection Program 600 illustrated in FIGS. 11A–11D. When the computer control program reaches a program state of 10, control is transferred over to the detection program 600. In general, the detection program uses digital video analysis techniques to analyze the video image of the detection means 60 (e.g. strip 61) generated by the camera 100 of the detection system 22. Preferably, the video processing program uses the digital data acquired from replicate capture sites to improve the accuracy and reliability of the overall amplification reaction as described below. First, however, it is important to define terms used in the description. Each detection means 60 includes at least a read zone 68 as shown in FIGS. 2A, 2G and 5A–5D. The read zones 68 of the devices of FIGS. 2A and 5 are shown in enlarged view in FIGS. 12A and 12B. The detection means 60 preferably also includes a reference bar and/or a control zone 70.

As mentioned above, each read zone 68 preferably includes multiple capture sites 74 for the purpose of multiplexing the assay. Multiplexing refers to performing an assay for more than one analyte at the same time; for example, testing for both Chlamydial organisms and gonococcal organisms, or testing for genetic mutations at multiple sites in a gene or even in multiple genes. Multiplexing can also refer to the simultaneous assay of one analyte along with a positive and/or negative control reagent These multiple capture sites 74 are depicted as continuous bands or lines in FIGS. 2A and 12A, and as a diagonal array of "spots" in FIGS. 5 and 12B. They were also described earlier as discontinuous bands or line as seen in FIG. 2G.

Figure 12A:
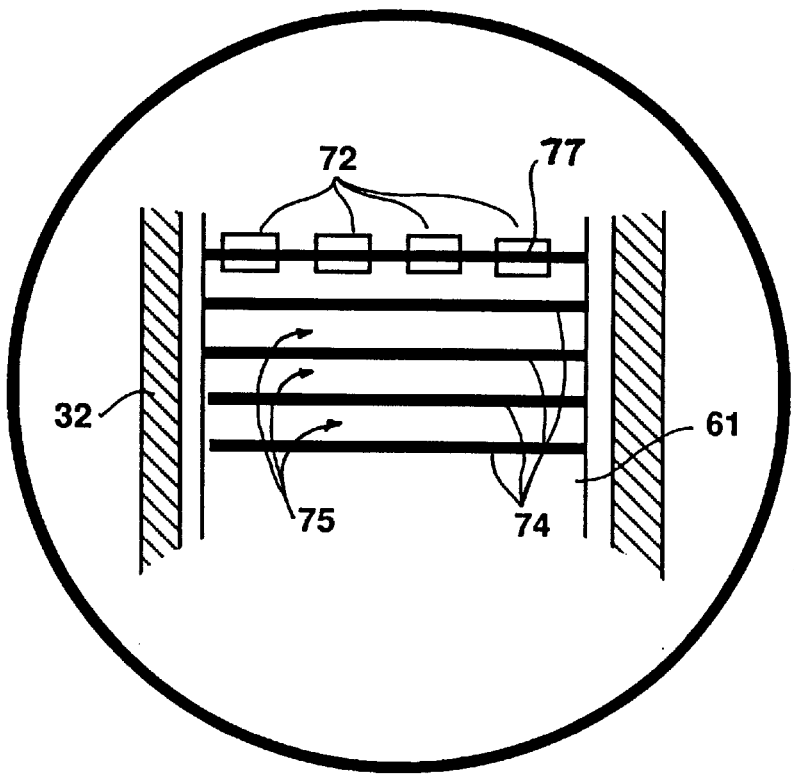
FIGS. 12A and 12B show enlarged read zone portions 68 of the strip supports shown in FIGS. 2A and 3A, respectively.

These multiple capture sites 74 must be distinguished from what will be described below as replicate sites 72 or replicate zones. Preferably the area of each distinct capture site 74 is large enough to support several "reading windows" which are referred to herein as replicate sites or replicate zones. These are depicted in FIG. 12A as the boxed areas on the top capture site 74, and as multiple scan lines on the spot 74 in FIG. 12B. In FIG. 2G, the discontinuous bands create natural replicate zones, while with continuous bands the replicate zones are created arbitrarily (see boxes 72 in FIG. 12A) by the reading software. It should be understood that each replicate site or zone of a capture site 74 contains additional data for the same analyte, as if "replicate" assays were being performed for that analyte. Having a plurality of replicate sites permits discarding of statistical "outliers" and increases the confidence level that the image of the capture site is correctly and faithfully evaluated.

Turning now to the video processing features of the invention, the computer 26 and the video processing program detect the presence of amplified target nucleic acid immobilized on the support 61. In general, the camera 100 detects an image of the support 61, usually in accord with one of the configurations illustrated in FIG. 8. The camera 100 then outputs a video signal to the frame grabber card 116 of the computer 26. The frame grabber card 116 digitizes a video frame and stores the digital values in RAM 124. Thus, the digital values are accessible to the computer 26 and may be manipulated by the video processing program 600. The computer 26 uses an 8-bit gray scale having a resolution of 512×484 pixels. A numerical value is assigned to each pixel such that a zero (0) represents a black image, and two hundred and fifty-five (255) represents a white image. The values between 0 and 255 each represent a particular shade of gray. The digitized representation of the video signal may be shown on the computer monitor 113 for viewing by an operator.

The video processing program 600 is illustrated by the flow chart shown in FIGS. 11A to 11D. The flow chart uses conventional symbols to represent the major functions performed by the video processing program 600. The video processing program 600 has two major sections or loops. The first section is the "Read" section which begins in block 606, and the second section is the "Assay" section which begins in block 634 and is a subroutine of the Read section 606. The Read section is executed once for each reaction/detection unit 20, and the Assay section is executed once for each capture site 74 imaged from the detection means 60 of each unit 20.

The program 600 starts in block 602 and initializes a position counter in block 604. The position counter keeps track of the number of reaction and detection units in a particular batch. For the disclosed dual annular ring embodiments, the heating rings 90, 92 include forty wells 97 for holding reaction/detection units 20. Block 608 advances the motor 108 or 109 to the next sample read position. In detection systems 22 using a mirror 106 for reflecting an image of the detection means 60 to the camera lens 102, the motor 108 would rotate the mirror as well in order to present successive images of each detection means 60 to the camera 100.

The reaction/detection units 20 preferably are provided with a bar code (not shown) which identifies the reaction sample 38 and the unit 20, and contains information about the assay to be performed for this reaction/detection unit. The bar code preferably also provides the computer 26 with information about the configuration of the detection means 60, such as information about the presence, location of and geometry (e.g. bands or spots) of control zones 70, capture sites 74, and replicate zones 72. Preferably, there are a limited number of such configurations and configuration information is stored in the computer's memory, to be retrieved by the computer upon receipt of a bar code signal that is associated with a particular configuration. Alternatively, if only one configuration is used, a single reference bar can provide a frame of reference for image analysis.

The cycler 16 and/or the computer 26 are then provided with a code reader (not shown) for reading the bar code. The program 600 reads the bar code information in block 610 and determines in block 612 whether the bar code was read successfully. If the read was unsuccessful, the program 600 indicates in block 614 that no bar code was read for this unit. In systems where bar code information is needed to locate the position and number of capture sites, the computer will not know how to process the particular unit 20 if the barcode is not successfully read and no result can be reported so the program 600 moves to block 616 which sends the program 600 to the sample end routine at block 678. If the read was successful, the program 600 moves to block 618 in which the zone configuration information is processed in preparation for obtaining and examining the digitized image.

Once the video image is fed from the camera 100 to the frame grabber card 116, the image is digitized at block 620 and scanned for the control zone 70 at block 622. The control zone is typically a prescribed zone that is ordinarily positive for any reaction sample. The control zone generally serves two functions. First, it indicates to the operator that the amplification reaction and transfer of the sample to the detection chamber proceeded properly. Second, it provides a reference point for determining the location of the capture sites as defined by the bar coded configuration information. In block 624, the program inquires whether the control zone was found. If the answer to the inquiry at block 624 is no, the program indicates an error code for the current sample and proceeds to block 616 which sends the program 600 to the sample end routine at block 678. If the answer to the inquiry at block 624 is yes, the program 600 proceeds to block 628 which sends the program 600 to the Assay Read routine at block 630.

The Assay Read routine moves to block 632 and, using the zone configuration information provided by the unit bar code or by other input, selects the first analyte zone for processing. Each analyte zone is divided into a plurality of scan-lines having a plurality of pixels in each scan-line. Each pixel was assigned a grayscale numerical value during the digitizing procedure in block 620. In block 636, the program 600 examines the scan-lines in the current analyte zone and calculates the pixel mean, standard deviation (SD) and range values for each scan-line in the current analyte zone.

The program 600 then moves to block 638 and asks whether any of the scan-lines in the current analyte zone are statistically different from other scan-lines in the current analyte zone. If the answer to the inquiry in block 638 is no, the program moves to block 640 and reports a negative result for the current analyte zone. The program 600 then moves from block 640 to block 642 which sends the program 600 to the next zone routine at block 670. If the answer to the inquiry in block 638 is yes, the program has detected a positive result for the current analyte zone and moves to block 644.

Figure 12B:
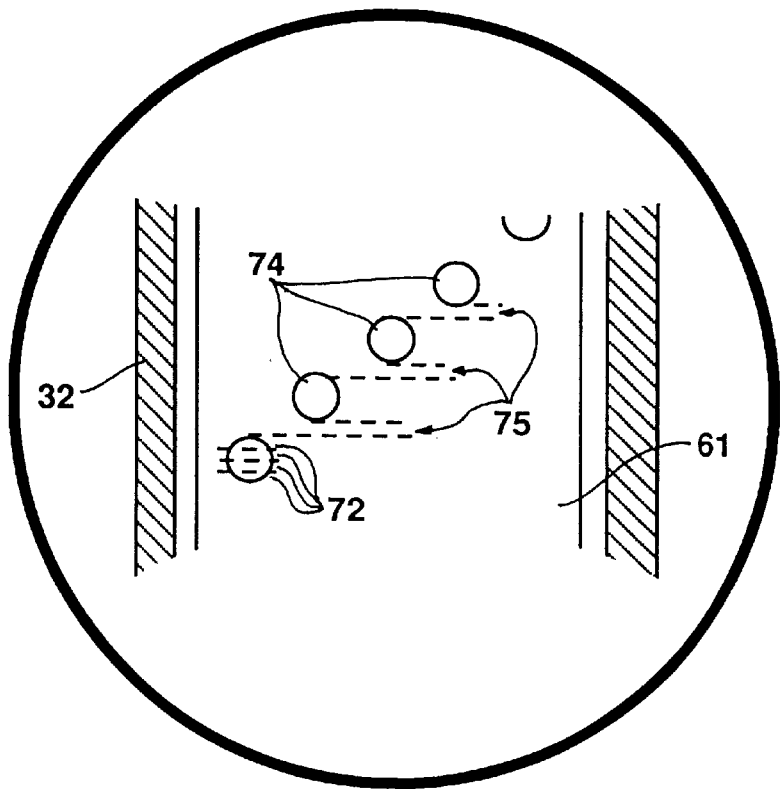

It will be appreciated that for a scan-line to be statistically different from the others it must contain a signal area whereas the other scan lines do not. Thus, it can be seen that the configuration of capture sites 74 and replicate sites 72 must leave some space between the sites. This is depicted in FIGS. 12A and 12B by the spaces 75. In the band configuration, the bands are placed sufficiently far apart that some scan-lines will examine the space between bands. In the spot configuration, adjacent spots should be separated by a vertical space 75 if horizontal scan-lines are employed. If this space 75 is not present and all capture sites 74 yielded positive signals, then all scan lines would contain signal and none would be statistically different.

Block 644 begins a background normalization procedure, where the program classifies each scan-line of the current analyte zone as containing some signal or only background. Using scan-lines classified as background only, the program 600 then establishes a background gradient for the current analyte zone in block 646, and uses this gradient to account for variance in lighting and position. Background gradients may be established in a variety of known ways such as by derivative and row/column analysis as is known in the art. In block 648, the program performs background adjustments or normalizations on the signal scan-lines using the background gradient information. Background normalization is traditionally used to establish a signal baseline and improve data interpretation, and may also be accomplished in a variety of known ways such as by subtraction or horizontal/vertical mean subtraction. The program then moves from block 648 to block 650 which transfers the program 600 to block 652.

The image processing subroutine begins at block 652. In block 654, the program uses contour enhancement to identify the perimeter of signal area 77 in a successful replicate site 72. Contour enhancement is a known digital image processing technique for feature extraction and is applied here to determine the contours or boundaries of the signal area for each replicate site. In block 656, the program calculates the mean, standard deviation and range values for all pixels within the perimeter of each replicate site signal area The analysis is now focused on the signal areas of the replicate sites.

In block 658, the program identifies any anomalous results by asking whether any of the signal area statistics in one replicate site are significantly different from the signal area statistics from other replicate sites 72. If the answer to this inquiry is no, all of the replicate sites 72 are judged to be the same, and the program 600 then calculates at block 660 the mean pixel value of the signal areas within all the replicate sites and stores this value as a result for the current analyte zone. From block 660, the program moves to block 662 which transfers the program to the next zone routine at block 670.

If the answer to the inquiry in block 658 is yes, the program 600 moves to block 664 which removes aberrant results which are referred to as statistical "outliers" or "fliers". Aberrant results can be defined statistically in a number of ways, including results falling too far from the mean, "too far" being defined in terms of the number of standard deviations, or in terms of the statistical significance within preset confidence limits. In block 666, the program determines whether there are enough acceptable sites remaining after discarding the aberrant or anomalous sites to obtain a reliable test result. Any of several criteria may be used to make the determination set forth in block 666. For example, the program may require a fixed percentage (e.g. at least 50%) of the identified replicate sites to be acceptable. If the number of acceptable replicate sites exceeds the established minimum, the program proceeds to block 660 to calculate the mean pixel value of the signal areas within the acceptable replicate sites and stores this value as a result for the current analyte zone. If the number of acceptable capture sites does not exceed the established minimum, the program proceeds to block 668 which sets the indeterminate result flag for the current analyte zone. In other words, the program could not find sufficient reliable data in the scanned image to reach a firm conclusion regarding the assay. The program then moves from block 668 to block 662 which takes the program to the next zone subroutine at block 670.

The program then moves to block 672 and asks whether the current zone is the last zone. If the answer to the inquiry in block 672 is no, the program selects the next analyte zone in block 674 and then moves to block 676 which returns the program to the assay loop at block 634. If the answer to the inquiry in block 672 is yes, the detection for the current reaction/detection unit 20 is complete, and the program moves into the sample end subroutine which begins at block 678.

In block 680, the program 600 stores all of the sample results and then displays and/or prints all sample results in block 682. Alternatively, the program can be configured to store all the data and print it at the end of a run. The position counter is then incremented in block 684, and the program asks in block 686 whether the last position has been completed. If the answer to the inquiry in block 686 is no, the program moves to block 690 which returns the program to the read loop at block 606. If the answer to the inquiry in block 686 is yes, the program ends at block 688.

It should be understood that use of the video imaging aspects of this invention are not limited to the preferred two tier cycling element and, in fact, are not limited to nucleic acid analysis at al. Rather, the video imaging aspects may be utilized on any form of assay, including for example immunoassay, where a signal can be generated such that it can be distinguished from the background using a camera means, and preferably some form of electromagnetic illumination.

8. Methods For Amplifying And Detecting Nucleic Acids

In accordance with another aspect of the invention, there are provided methods for performing nucleic acid amplification and detection. As described in the Background of the Invention, various methods for amplifying nucleic acids are known in the art. Amplification reactions contemplated by the present invention include, but are not limited to, PCR, LCR, 3SR, and SDA. In the present invention, the amplification reaction sample generally comprises target nucleic acid, at least one enzymatic agent that induces amplification, and a buffer. Enzymatic agents contemplated by the invention include, but are not limited to, ligases and polymerases, and combinations thereof. The reaction sample may also include primers or probes, which are described further below. Preferably, primers or probes are added in molar excess of the amount of target nucleic acid in the reaction sample.

It will be readily apparent to those persons skilled in the art that certain additional reagents may be employed, depending on the type of amplification reaction. For instance, for PCR amplification reactions, the reaction sample will generally also include nucleotide triphosphates, dATP, dCTP, dGTP, and dTIP. LCR reaction samples usually include NAD. The amounts of all such reagents in the reaction sample may be determined empirically by those persons skilled in the art Examples of reaction samples for particular amplification reactions are described further in Examples 4, 9, and 11 of this disclosure.

The nucleic acid of interest to be amplified, referred to as the target nucleic acid, may comprise deoxyribonucleic acid (DNA) or ribonucleic acid (RNA), and may be natural or synthetic analogues, fragments, and/or derivatives thereof. The target nucleic acid is preferably a naturally-occurring viral nucleic acid or DNA of prokaryotic or eukaryotic origin.

The terms "primer" and "probe" as used in the present application are intended to refer generally to an oligonucleotide which is capable of sufficiently hybridizing with the target nucleic acid. The term "primer" is typically used in connection with PCR, and the term "probe" is typically used in connection with LCR. The term "primer/probe" will be used in the present application where general discussions can apply to both primer and probe sequences.

In the methods of the invention, the primer/probe is preferably selected to be complementary to various portions of the target nucleic acid. The length of the primer/probe will depend on various factors, including but not limited to, amplification reaction temperature, source of the primer/probe, complexity of the target nucleic acid, and the type of amplification reaction. Preferably, each primer/probe is sufficiently long to have a desired specificity and avoid hybridization with random sequences that may be present in the reaction sample. More preferably, each primer/probe comprises about 15 to about 100 bases, and even more preferably, about 15 to about 40 bases.

The primer/probe may be chemically synthesized using methods known in the art. Preferably, the primer/probe is synthesized using nucleotide phosphoramidite chemistry techniques known in the art and/or instruments commercially available from Applied Biosystems, Inc. (Foster City, Calif.), DuPont (Wilmington, Del.) or Milligen (Bedford, Mass.).

Pimer/probes may be directly linked to detectable label which does not interfere with hybridization. Alternatively, a specific binding pair member is attached to at least one primer/probe employed in the amplification reaction. Preferably, a specific binding pair member is attached to each primer in a primer pair, or to at least two probes in a set of probes employed in the amplification reaction. More preferably, the specific binding pair members thus attached to the primers in the primer pair or to the at least two probes in the set of probes are two different specific binding pair members. As described further below, a first specific binding pair member attached to a primer pair or probe set can be used to couple amplified target with a reporter molecule conjugated to a detectable label. The second specific binding pair member can then be used to bind the labeled amplified target to a capture molecule immobilized on the support 61. Preferably, the two specific binding pair members do not cross react with each other and do not cross react with the labeled reporter molecules or the capture molecules immobilized on the support 61.

Typically, the specific binding pair member comprises an antigen, hapten, chemical compound, or polynucleotide capable of being bound by another molecule such as an antibody or complementary polynucleotide sequence. The specific binding pair member may also be a magnetic particle. Specific binding pair members contemplated by the present invention include, but are not limited to, biotin, T3, oligonucleotides, polynucleotides, and drug compounds such as theophylline, digoxin, and salicylate. Such specific binding pair members are known in the art and are commercially available.

Methods of attaching or linking specific binding pair members to the primer/probe are also known in the art. For example, the specific binding pair member may be attached to the primer/probe through covalent bonding or standard β-cyanoethyl-phosphoramidite chemistry techniques. Enzo Biochemical (New York) and Clontech (Palo Alto, Calif.) have also described and commercialized primer/probe labeling techniques. The methods employed will vary depending, for instance, on the type of specific binding pair member and the position of the binding pair member on the primer/probe sequence. The binding pair member should, however, be attached by thermostable means to survive any temperature cycling employed in the amplification reaction.

To conduct the amplification reaction, the reaction sample 38 is placed in the reaction chamber 30. Because the quantity of reaction sample is typically small, it may be preferable to place the sample 38 in the reaction chamber 30 using a microsyringe pipette (not shown), or to briefly centrifuge the chamber to force the sample 38 to the bottom of the chamber. The reaction chamber 30 and detection chamber 32 are then engaged to form a sealed unit 20, and the unit 20 is placed in a thermal cycling device 16, preferably, a thermal cycling device 16 as shown in FIGS. 6–8 and described herein. The reaction sample 38 is then exposed to temperature conditions sufficient to amplify target nucleic acid present in the reaction sample. For some amplification reactions, such as PCR and LCR, the reaction sample will be exposed to thermal cycling. Other amplification reactions, however, such as SDA and 3SR, may employ isothermal conditions. Under thermal cycling conditions, the reaction samples are typically exposed to a range of temperatures for set periods of time. For LCR, there is usually temperature cycling at two different temperatures. For example, as described in Example 5, the reaction sample is cycled at 85° C. and 55° C. Those skilled in the art can determine empirically, without undue experimentation, suitable temperatures, cycling times, and the number of cycles needed to complete the amplification reaction. Under appropriate temperature conditions, and in the presence of target nucleic acid in the reaction sample, the primers or probes will hybridize to the target nucleic acid as the amplification reaction proceeds.

When the amplification reaction is completed, the reaction sample is transferred from the reaction chamber 30 to the detection chamber 32 so that the reaction sample 38 comes into contact with the support 61 (FIGS. 5A to 5E). During transfer of the reaction sample 38 to the detection chamber 32, the unit 20 remains sealed. The transfer of sample may occur by various means such as by creation of a vapor phase or expansion of fluid or propellant caused by increased temperature.

Preferably, transfer of the reaction sample 38 to the detection chamber 32 occurs by expansion of a propellant 40 at the bottom end of the reaction chamber 30. In the preferred embodiment, the expansion of the propellant 40 is caused by the computer 26 raising the temperature of the lower heating element 18 (or only heating element 17) above the propellant's threshold temperature. More particularly, the computer 26 directs the heating element 17 or 18 to deliver heat to the second longitudinal segment 35 of the reaction chamber 30 so that the propellant 40 is exposed to a temperature above the propellant's threshold temperature. Typically, the element is super-heated to a temperature above 95° C., usually at or above 100° C. The heat thus delivered to the reaction chamber 30 causes the propellant to expand, thereby transferring the reaction sample upward toward the detection chamber 32. The temperature needed to expand the propellant 40 will depend on the nature and composition of the propellant 40. It is preferred that the propellant 40 has a threshold temperature above the amplification reaction temperature(s) so that the propellant 40 does not expand during the course of the amplification reaction.

In a preferred embodiment, one region 66 of the support 61 comprises multiple conjugate molecules capable of binding to a first specific binding pair member attached to the amplified target in the reaction sample. The conjugate molecules are deposited on the support 61 using methods known to persons skilled in the art. For example, the conjugate molecules can be deposited on the support 61 by spotting and drying. Preferably, the conjugate molecules are dried on the support 61 in the presence of meta-soluble proteins, such as casein, to aid in the transport and resolubilization of the conjugate molecules. The conjugate molecules can also be deposited on the support by methods described in U.S. Pat. No. 5,120,643, incorporated herein by reference. The conjugate molecules in the region 66 are not immobilized on the support but rather are capable of resolubilizing in the presence of reaction sample and/or aqueous solvent and move along the support by capillary movement. Examples of conjugate components capable of binding to the specific binding pair members described above include, but are not limited to, antibiotin antibodies, anti-theophyline antibodies, avidin, carbohydrates, lectins, complementary oligonucleotide or polynucleotide sequences, streptavidin, and protein A.

The conjugate molecules thus deposited on the support are conjugated to a label. The term "label" as used in the present application refers to a molecule which can be used to produce a detectable signal. The signal should be able to be detected visually, optically or upon excitation by an external light source. Suitable labels are known in the art and include latex, colored latex particles, and colloidal metals such as gold or selenium. Alternatively, the label may be a fluorescent molecule such as fluorescein, rhodamine, acridine orange, and Texas red. Additional labels which may be employed in the invention are described in U.S. Pat. No. 4,166,105; U.S. Pat. No. 4,452,886; U.S. Pat. No. 4,954,452; and U.S. Pat. No. 5,120,643. Such labels may be conjugated or linked to the reporter molecules according to methods generally known in the art. [See, U.S. Pat. No. 5,120,643; U.S. Pat. No. 4,313,734].

As the reaction sample contacts a first region 66 of the support 61 modified as described above, the amplified target nucleic acid coupled to specific binding pair members binds to the labeled reporter molecules. Also, the reporter molecules on the support are resolubilized and are mobilized with the amplified target nucleic acid in the reaction sample. As has been mentioned, the conjugate need not be present on the strip and is not needed at all if a detectable label is directly linked to the primer/probe.

By capillary movement, the reaction sample, along with the labeled amplified target, is transported to a second region 68 of the support 61. The second region 68 of the support 61 preferably includes a plurality of capture molecules (capture sites 74) capable of binding to a second specific binding pair member attached to the amplified target nucleic acid. Where the second specific binding pair member attached to the amplified target is a magnetic particle, the capture molecule(s) should be selected so as to be able to capture and immobilize the amplified target by magnetic attraction. All such capture molecules are immobilized on the support 61. Methods of immobilizing the capture molecules on the support 61 are known in the art and include adsorption, absorption, and covalent binding, as well as those methods described in U.S. Pat. No. 5,120,643. The amount of capture molecules immobilized on the support 61 will vary, depending, for instance, on the binding affinity for the specific binding pair member. Preferably, the concentration of capture molecules immobilized on the support 61 is in molar excess of the amplified target.

Preferably, the plurality of capture molecules are immobilized on the support 61 at predetermined locations or zones (capture sites 74) on the support 61. The capture molecules can be immobilized in any desired geometric form or configuration, such as a diagonal, vertical, or horizontal configuration, or in the form of circles or bars. It is more preferable to spatially separate any such circles or bars so that the results of the amplification reaction can be suitably detected and resolved.

As the reaction sample and labeled amplified target contacts the second region 68 of the support 61, labeled amplified target nucleic acid in the reaction sample 38 will bind to the immobilized capture molecules (capture sites 74) on the support 61 and will become immobilized at that location. Sample components not bearing the capture hapten will be cleared from the second region 68 to any additional zones and/or to the second end 64 of the support 61 by capillary movement of the reaction sample 38.

Further, the support 61 may also comprise a third region referred to herein as a "control" zone 70. The control zone 70 is modified so as to provide a control or reference standard in the detection method. Preferably, the control zone 70 includes some reagent that will capture a detectable label at a predetermined location on the support 61. The support 61 can, of course, comprise additional regions or zones for conducting further analysis. Alternatively, or additionally, the support 61 may comprise a reference spot or zone including a detectable dye which, while not reactive with reagents, provides a detectable signal that serves as a frame of reference for automated imaging by the camera.

The labeled amplified target nucleic acid immobilized on the support 61 produces a visible indicator, and this visible indicator is detected and analyzed by the detection system 22 and computer 26. The visible indicator thus produced is an indication of the presence or amount of amplified target nucleic acid in the reaction sample 38. If no amplified target nucleic acid is present in the reaction sample 38, no labeled amplified target will bind to the immobilized capture molecules and no visible indicator will be measured. The density or intensity of the indicator on the support 61 can be read optically by any means. As described herein for one embodiment, the signal is reflected onto a video camera lens 102 by a reflecting mirror 106. As the mirror 106 rotates, each of the supports 61 in each of the detection chambers 32 can be read.

In addition to the preferred embodiments described above, the invention contemplates alternative methods for labeling and immobilizing target nucleic acid. For instance, the primer/probe may be coupled to a detectable label during manufacture. Alternatively, the primer/probe may be coupled during manufacture with a specific binding pair member that allows it to bind to a detectable label that is conjugated to a complementary specific binding pair member. The binding of the complementary specific binding pair members can take place either during or after the amplification reaction. Thus, it is contemplated that amplified target nucleic acid in the reaction sample can be coupled to a detectable label prior to being transferred to the detection chamber 32.

In a further embodiment, labeled amplified target nucleic acid is detected in the detection chamber 32 by means of microparticle agglutination. In this embodiment, a pair of primers or a set of probes is coupled during manufacture with the same specific binding pair member. Microparticles conjugated to complementary specific binding pair members are then included as part of the detection means 60. As the reaction sample 38 is transferred to the detection chamber 38 and comes into contact with the detection means 60, amplified target present in the reaction sample 38 binds to the coated microparticles. By virtue of the bivalency of the amplified target, the microparticles agglutinate. Unamplified probes or primers may bind only one microparticle, and will not be able to initiate agglutination. The agglutination can then be detected and analyzed by the detection system 22 as described above.

9. Kits of the Invention

The invention also provides kits for amplifying and detecting nucleic acids. The kits comprise multiple disposable reaction chambers 30, multiple disposable detection chambers 32, and engagement means for sealably securing each reaction chamber 30 to a detection chamber 32. Each of the disposable detection chambers 32 include a support 61 modified for immobilizing amplified target nucleic acid. The kit also comprises one or more containers holding in a suitable buffer reagents for performing amplification reactions. For PCR, such reagents include DNA polymerase, dATP, dCTP, dTTP, dGTP and at least two primers specific for a predetermined target nucleic acid. For LCR, such reagents include DNA ligase, NAD, and at least four probes specific for a predetermined nucleic acid. Suitable containers for the reagents include bottles, vials and test tubes. In a preferred embodiment, the disposable reaction chambers 32 in the kit are pre-packaged with selected reagents and closed with a puncturable seal.

10. EXAMPLES

Example 1: Construction of Thermal Cyclers

A. A dual-ring thermal cycler was constructed from two aluminum rings having the following dimensions: 105 mm outer diameter, 95 mm inner diameter, and 13 mm height. The gap between the rings was 2 mm. Each ring contained 40 aligned wells for holding reaction/detection units 20, each well having a diameter of approximately 2.3 mm. The rings were equipped with radial cooling fins on the internal surface as shown in FIG. 7. Self-adhesive heating strips (Minco Products, Minneapolis, Minn.) were attached to the outer circumference of the upper and lower rings. The heating strips thus attached were capable of delivering about 300 watts of power to each ring. The temperature of the rings was controlled by electronics and the software as described above. A Charge Coupled Device (CCD) camera and movable mirror were installed along the center axis of the rings above the cooling fan.

B. A thermal cycler was constructed from a single annular ring of aluminum with dimensions: outer diameter 105 mm, inner diameter 94 mm, and height 36 mm. The ring contained 36 wells for reaction tubes, each well being 3.5 mm diameter. The ring was equipped with radial cooling fins on the internal surface. A self-adhesive heating strip (Minco Products, Minneapolis, Minn.) was attached to the outer circumference. The temperature of the ring was controlled by control electronics and the software as described above. A CCD camera was installed external to the ring and a light source was installed in the center.

C. A dual-tier thermal cycler was constructed from two rectangular aluminum blocks having the following dimensions: 84 mm×25 mm×6 mm. Each block contained 12 wells for holding reaction/detection units 20, each well having a diameter of approximately 0.31 cm. The blocks were equipped with cooling fins on one surface. Self-adhesive heating strips (Minco Products, Minneapolis, Minn.) were attached to the other surface. The temperature of the blocks was controlled by electronics and software as described above.

Example 2: Preparation of Antibody Reagents

A. Antiserum: Antiserum to biotin, adamantane, quinoline, dibenzofuran, thiophene-carbazole, and acridine were raised in rabbits against each hapten conjugated to BSA. Details of preparing antibodies to adamantane, quinoline, dibenzofuran, thiophene-carbazole, and acridine are found in co-owned, co-pending applications Ser. Nos. 07/808,508, 07/808,839, 07/808,839, 07/808,839 and 07/858,929, respectively. These applications are incorporated by reference, but are not deemed essential to the invention. Monoclonal antibody to fluorescein was raised in mouse using standard techniques. Antiserum against dansyl was a mouse monoclonal obtained from the University of Pennsylvania (S-T. Fan and F. Karush, *Molecular Immunology*, 21, 1023–1029 (1984). The antisera were purified by passage through protein A Sepharose® or protein G Sepharose® (Pharmacia, Piscataway, N.J.) and diluted in 0.1 M TRIS pH 7.8, 0.9% NaCl, 0.1% BSA, 1% sucrose, 1% isopropanol, and a trace of phenol red.

B. Conjugates: Colloidal selenium was prepared following the procedure of D. A. Yost, et al (U.S. Pat. No. 4,954,452 (1990)). The colloid was diluted in water to achieve an optical density of 16 at 545 nm. To 1 mL of this suspension was added 1 μL of anti-biotin at 1 mg/mL and 60 μL of BSA at 100 mg/mL. This suspension was mixed on a vortex mixer for 1 minute. A 0.5 mL portion of this mixture was diluted with 0.5 mL of 40 mM TRIS pH 7.8, 4% casein, and allowed to soak into a 10×1.25 cm glass fiber-based pad (Lypore 9254, Lydall Inc., Rochester, N.Y.). The pad was lyophilized and cut into 6×6 mm sections.

Anti-biotin antiserum was also conjugated to polystyrene uniformly-dyed blue latex particles (Bangs Laboratories, Carmel, Ind.). The latex particles (380 nm diameter) were diluted 1:25 in water to give 1 mL at 0.4% solids, and 10 μL of anti-biotin at 1 mg/mL was added. The suspension was mixed on a vortex mixer for 45 seconds, and 5 μL of 5% casein in 0.1 M TRIS (pH 7.8) was added. A 0.5 mL portion of this mixture was diluted with 0.5 mL of 40 mM TRIS (pH 7.8), 4% casein, and allowed to soak into a 10×1.25 cm pad (Lypore 254™, Lydall, Inc., Rochester, N.Y.). The pad was lyophilized.

C. Solid supports: Anti-dansyl antibody (1 mg/mL) was applied to nitrocellulose sheets (5 μm pore size, precast onto Mylar®, Schleicher and Schuell, Keen, N.H.) using a motor-driven microsyringe. In addition, anti-adamantane, anti-acridine, anti-quinoline, anti-dibenzofuran, anti-thiophenecarbazole, and anti-fluorescein antibodies at 0.5–1 mg/mL were applied to different nitrocellulose sheets (5 μm pore size, Schleicher and Schuell, Keen, N.H.) by reagent jetting as described in U.S. Pat. No. 4,877,745 (Abbott) to form a multiplex capture support.

Example 3: Preparation of Detection Chambers

A. Tubular: Tubular detection chambers were constructed of plexiglass tubes of approximately 3 mm internal diameter. The top ends of the detection chambers were closed, and the bottom ends were tapped to fit threaded microtube reaction chambers described in Example 4A below.

The Lydall antibiotin conjugate pad of Example 2B was affixed to the bottom of the antidansyl nitrocellulose supports 61 (Example 2C) with adhesive tape. The nitrocellulose-Lydall pad support was then sliced into 3×50 mm strips, which were inserted, with the Lydall pad portion downward, into detection chambers made of plexiglass tubes of approximately 3 mm internal diameter.

B. Rectangular Chamber with Reservoir: Strip holders of the design shown in FIG. 2A–2E were molded of polycarbonate. Into the base, in the orifice leading from the reaction tube to the reservoir, was placed a 6×6 mm section of the selenium antibiotin conjugate pad of example 2B. A multiplex capture support strip with immobilized antibody (example 2C), was placed in the strip holder. The lid was welded to the base of the strip holder by ultrasound such that the strip was held in place by the pins.

Example 4: Reaction Chamber Preparation

Figure 13:
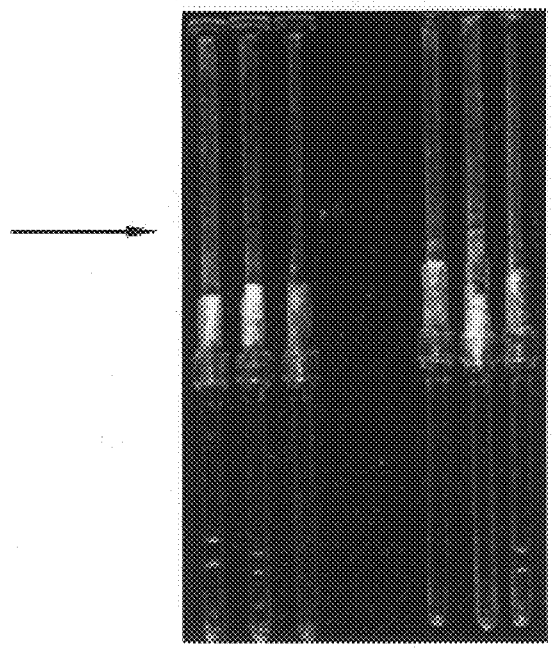
FIGS. 13 and 14 are digitized photographic images of the results of six reaction samples as described in Examples 6 and 12, respectively. In each Figure, the three samples on the left contained target DNA and a spot or band is visible; the three on the right did not.

A. P.C.R. Microsyringe Tips, were purchased from Tri-Continent Scientific, Inc., Grass Valley, Calif. and the open tips (bottoms) were sealed closed with heat These reaction chambers were made of polypropylene, had a volume of 100 μL and an internal diameter of 1.8 mm. The tops were threaded as shown in FIG. 13.

B. Custom reaction chambers were ordered from Varivest, Inc. Grass Valley, Calif. These chambers were constructed of polypropylene capillary tubes to have a volume of 100 μL, 3.5 mm OD, 2 mm ID and a length of 3.5 cm. Curiously, in tests where the reaction sample alone served as propellant, these tubes performed very poorly unless the already sealed bottoms were first melted, presumably introducing surface irregularities at or near the lower, closed end.

Example 5: Reaction Sample Preparation, J3.11

Oligonucleotide probes were synthesized by phosphoramidite chemistry on an ABI DNA synthesizer and were haptenated with either biotin or dansyl haptens as indicated. The sequences (SEQ ID NOS 1, 2, 3 and 4 shown below) were used to amplify a portion of human chromosome 7 coding for the J3.11 polymorphism which is loosely linked to cystic fibrosis. (I. Bartels, et al., *Am J. Human Genetics,* 38:280–7 (1986). They align on the target (50-base synthetic target: SEQ ID NO. 5) as shown below:

| SEQ ID NO. | SEQUENCE and ALIGNMENT |
|---|---|
| 1. | 5'-biotin-GTGTCAGGACCAGCATTCC-3' |
| 2. | GTAAAGGGGAGCAATAAGGT-3' |
| 5. | 5'-ATATTGTTGTGTCAGGACCAGCATTCCGGGAAAGGGGAGCAATAAGGTCA-3' |
| 5'. | (3'-TATAACAACACAGTCCTGGTGCTAAGGCCCTTTCCCCTCGTTATTCCAGT-5') |
| 3. | 3'-biotin-CACAGTCCTGGTCGTAAG |
| 4. | CCATTTCCCCTCGTTATTCCA-dansyl-5' |

To perform "double-gap" LCR as described in Backman, et al. European Patent Application 439 182, reaction sample mixtures contained the following reagent concentrations in a total volume of 100 μL: 50 mM EPPS, titrated with KOH to achieve pH 7.8; 20 mM K+; 30 mM $MgCl_2$; 10 μM NAD, 1.7 μM dGTP, 9000 units DNA ligase from *Thermus thermophilus;* 1 unit DNA polymerase from *Thermus aquaticus;* 1 μg herring sperm carrier DNA; $4 \times 10^{12}$ copies (6.7 nmole) of each oligonucleotide probe (SEQ ID NOS. 1, 2, 3 and 4); and $10^7$ copies target DNA (SEQ ID NO. 5).

The reaction samples were pipetted into reaction chambers of example 4A. The reaction chambers were then centrifuged briefly to force the reaction sample to the bottom of the chamber. The reaction chambers were screw-threaded to the detection chambers described in Example 3A to form sealed reaction/detection units 20.

Example 6: Amplifying DNA and Transferring Reaction Sample From Reaction Chamber To Detection Chamber The sealed reaction/detection units of Example 5 were inserted into a split ring thermal cycler. (See Example 1A). The upper and lower rings were subject to the following protocol of temperature in order to effect the LCR reaction: 40 cycles of 82° C. for 5 seconds and 55° C. for 60 seconds. Each cycle took approximately 2 minutes to complete, for a total LCR time of about 80 minutes.

Following completion of the temperature cycling, the lower ring was heated to 110° C., and the upper ring was heated to 100° C. These temperatures were held for 25 seconds. By thermal expansion and vaporization of the reaction sample in the reaction chamber, the sample was transferred from the reaction chamber to the detection chamber, where the reaction sample contacted the first end of the support 61 containing the labeled anti-biotin conjugate. The labeled anti-biotin was re-solubilized, and the reaction sample proceeded by chromatography up the nitrocellulose support 61. In reaction samples containing amplified target DNA, the amplification product was bound at the anti-dansyl capture sites on the support 61 and visible color development was observed. The results of six reaction samples are shown in FIG. 13. The three samples on the left contained target DNA and dark spots are visible on the detection strip (see arrow). The three samples on the right contained no target DNA and no spots are visible.

Example 7: Detection Imaging

The detection chambers of Example 6 were scanned to a TIFF file with a flatbed scanner (ScanJet C, Hewlett-Packard, Palo Alto, Calif.) using grayscale settings of brightness 140 and contrast 150. The TIFF file was imported into Image™ (available from the National Institutes of Health, Research Services Branch, N.H.) and the images of the developed bands analyzed for pixel density. The results are tabulated in Table 1 below, where maximum density and minimum density refer to the gray level of the image in the immediate vicinity of the band.

TABLE 1

|  | strip 1 (pos) | strip 2 (pos) | strip 3 (pos) | strip 4 (neg) | strip 5 (neg) | strip 6 (neg) |
|---|---|---|---|---|---|---|
| max density | 183 | 203 | 210 | 164 | 159 | 183 |
| min density | 143 | 147 | 186 | 135 | 129 | 159 |
| difference | 40 | 56 | 34 | 29 | 30 | 24 |

Example 8: Video Processing

A photographic image of the color reaction product described in Example 6 was taken by the CCD camera. The presence or absence and amount of color reaction in the specified regions of the support 61 was determined by analysis of gray scale data files generated from the image, using software described earlier in this disclosure.

Example 9: Alcohol Propellant

The reaction sample of Example 5 is prepared in a microsyringe-barrel reaction vessel, except that 2 μL of 1-propanol is placed at the bottom end of the reaction chamber, and the reaction sample is placed in the chamber so that the sample and the 1-propanol are separated by about 2.5 μL air. The reaction chamber is then sealably fitted with the detection chamber 32 to form a sealed reaction/detection unit 20 as in Example 5. DNA amplification, and the post-heating protocol of Example 6 are executed, except that the upper and lower ring are both heated to 100° C. The vaporization of the 1-propanol forces the reaction sample upwards so as to contact the support 61 in the detection chamber. The color reaction product on the support strips 61 can then be analyzed by the imaging detection system described in Example 7 or 8.

Example 10: Nucleation of Propellant Expansion

The reaction sample of Example 5 was prepared except that several glass microbeads (average diameter 0.2 mm)

(Homogenizing beads, Virtis Corporation, Gardiner, N.Y.) were added. The steps described in Examples 6 and 7 were then performed. The glass beads act as nuclei for initiation and localization of boiling at the bottom end of the reaction chamber, and the vapor thus generated serves to transfer the reaction sample into the detection chamber. The color reaction product on the support strips 61 were then analyzed by the imaging detection system and procedure described in Example 7.

Example 11: Reaction Sample Preparation, β-globin

Figure 14:
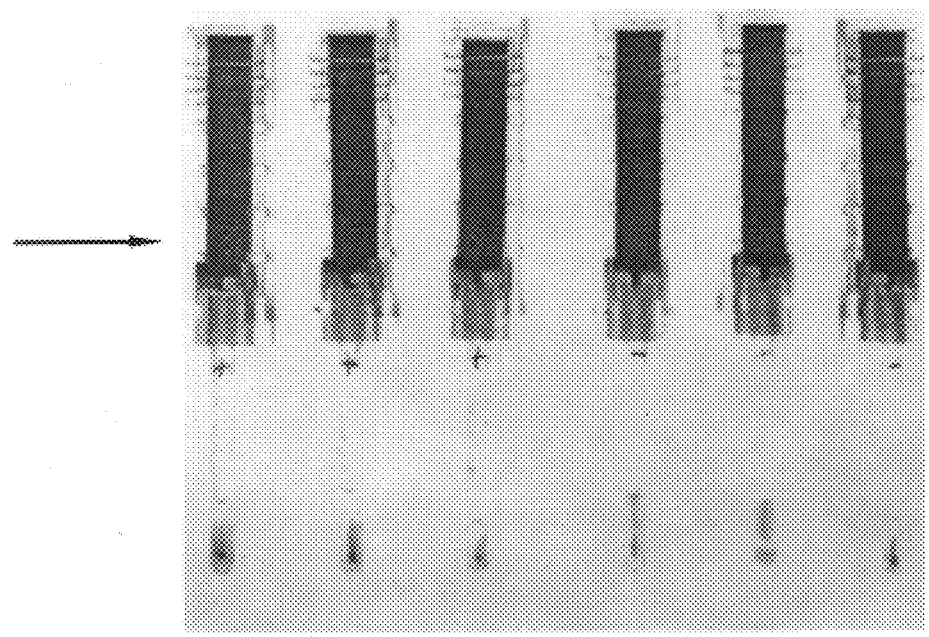

Oligonucleotide probes (SEQ. ID NOS. 6, 7, 8, and 9) which hybridize with the human β-globin gene (SEQ. ID NO. 10) were synthesized by phosphoramidite chemistry on an ABI DNA synthesizer and were haptenated with biotin or adamantane as shown.

amplification product was retained at the anti-adamantane capture site and visible color development was seen. No color was seen at any other antibody locus. The reaction units are shown in FIG. 14.

Example 13: Video Processing

The reaction/detection units of examples 11 and 12 are imaged and processed according to the procedures of Examples 7 and 8.

Example 14: Multiplex Supports

Support strips 61 were prepared as in Example 3B with a plurality of antibody binding sites, each antibody specific for a different hapten. The strips also contain biotin-labeled egg albumin at a specific location on the support. The biotin labeled protein serves as a control or reference standard.

| SEQ ID NO. | SEQUENCE and ALIGNMENT |
| --- | --- |
| 6. | 5'-adam-GGGCAAGGTGAACGTGGA |
| 7. | GAAGTTGGTGGTGAGGCC-biotin-3' |
| 10. | 5'-CCTGTGGGGCAAGGTGAACGTGGATGAAGTTGGTGGTGAGGCCCTGG-3' |
| 10'. | (3'-GACACCCCGTTCCACTTGCACCTACTTCAACCACCACTCCGGGACCC-5') |
| 8. | 3'-CCCGTTCCACTTGCACC |
| 9. | ACTTCAACCACCACTCCGG-biotin-5' |

To perform the so-called "double-gap" LCR method described by Backman, et al European Patent Application 0 439 182 (1991) reaction sample mixtures contained the following final concentrations in a total volume of 100 μL: 50 mM EPPS pH 7.8, KCl titrated with KOH to achieve pH 7.8 and 20 mM K+, 30 mM MgCl2, 10 μM NAD, 1.7 μM dGTP, 9000 units DNA ligase (from *Thermus thermophilus*), 1 unit DNA polymerase (from *Thermus aquaticus*), and $1 \times 10^{12}$ copies (1.7 pmole) of each oligonucleotide (SEQ ID NOS. 6, 7, 8 and 9). Targets were 250 ng human placental DNA (about $10^5$ copies), which contain SEQ ID NO. 10, or water.

Reaction mixtures were pipetted into 100 μL reaction chambers according to example 4B, the bottoms of which had been melted and cooled. The reaction chambers were centifuged briefly to force the reaction mixture to the bottom of the tube. The tubes were capped with the detection units of Example 3B to form sealed reaction/detection units.

Example 12: Amplifying DNA and Transferring Reaction Sample From Reaction Chamber To Detection Chamber The combined reaction/detection units of example 11 were inserted into the thermal cycler of example 1B and subjected to the following sequence of temperature in order to effect the LCR reaction: 35 cycles of 88° C. for 10 seconds and 53° C. for 60 seconds. Each cycle took approximately 2 minutes to complete, for a total LCR time of about 80 minutes. Following the completion of the amplification cycles, the ring was heated to 104° C. This temperatures was held for 25 seconds. By virtue of thermal expansion and vaporization of the reaction mixture, the liquid sample was ejected from each reaction element to the affixed detection element, where the amplified sample entered the dried pad containing anti-biotin conjugate. The labeled antibody in the pad was solubilized, and the mixture proceeded by chromatography up the nitrocellulose strip. When the appropriate DNA sequence was present in the test sample, the resultant Example 15: Multiplex Detection Oligonucleotide probes are synthesized as described in Example 5 or 11, and:

The four probes of example 11 hybridize with the human β-globin gene. Two of the probes contain terminal biotin moieties, allowing them to bind with anti-biotin-latex conjugate and one contains terminal adamantane, allowing them to bind with anti-adamantane at a specific binding zone on the support strip. This serves as a positive control.

Four other probes hybridize with a sequence unknown in nature. Two of the probes contain terminal biotin moieties, allowing them to bind with anti-biotin-latex conjugate, and two of them contain terminal dibenzofuran, allowing them to bind with anti-dibenzofuran at a specific binding zone on the support strip. This serves as a negative control.

Four other probes hybridize with the portion of human chromosome 7 coding for the $\Delta F_{508}$ mutation of cystic fibrosis. Two of the probes contain terminal biotin moieties, allowing them to bind with anti-biotin-latex conjugate, and two of them contain terminal fluorescein, allowing them to bind with anti-fluorescein at a specific binding zone on the support strip.

Four other probes hybridize with the portion of human chromosome 7 coding for the $G_{551}D$ mutation of cystic fibrosis. Two of the probes contain terminal biotin moieties, allowing them to bind with anti-biotin-latex conjugate, and two of them contain terminal thiophene-carbazole, allowing them to bind with anti-thiophene-carbazole at a specific binding zone on the support strip.

Four other probes hybridize with the portion of human chromosome 7 coding for the $G_{542}X$ mutation of cystic fibrosis. Two of the probes contain terminal biotin moieties, allowing them to bind with anti-biotin-latex conjugate, and two of them contain terminal quinoline, allowing them to bind anti-quinoline at a specific binding zone on the support strip.

Four other probes hybridize with the portion of human chromosome 7 coding for the $W_{1282}X$ mutation of cystic fibrosis. Two of the probes contain terminal biotin moieties, allowing them to bind with anti-biotin-latex conjugate, and two of them contain terminal dansyl, allowing them to bind with anti-dansyl at a specific binding zone on the support strip.

The DNA sequences surrounding each of these mutations can be found in the literature. LCR amplification is then performed using conditions of examples 5–6 and 11–12, the strips are developed, and the spots are visualized as described in Examples 7–8.

Example 16: Multiplex Video Processing

Support strips 61 are prepared as in Example 11, except that each antibody (or biotin-labeled protein) appears at three or more specific locations on the strip. A plurality of specific capture sites 74 or binding areas allows the video processing program 600 to average the signal from similar spots, thus increasing the confidence of the assignment of a particular result. In addition spurious signal may be rejected if similar spots do not exhibit color.

While the above-described embodiments of the invention are preferred, those skilled in this art wilt recognize modifications of structure, arrangement, composition and the like which do not depart from the true scope of the invention. The invention for which protection is sought is defined by the appended claims.

We claim:

1. A method for transferring a fluid sample between a reaction chamber and a detection chamber within a device, comprising the steps of:

a) providing a device having a reaction chamber and a detection chamber connected by means for fluid communication between the reaction and detection chambers, and having a reaction sample disposed in said reaction chamber, wherein a propellant is also disposed in said reaction chamber such that the sample is between the propellant and the means for fluid communication, and wherein further the propellant is non-mechanically inducible to expand; and b) non-mechanically inducing the propellant to expand to occupy a larger volume, thereby forcing the sample through the means for fluid communication into the detection chamber.

2. The method of claim 1 wherein said reaction chamber is an elongated chamber and said inducing step comprises the application of heat to said propellant.

3. The method of claim 2 wherein said heat is applied to a localized area of said elongated reaction chamber, said localized area containing the propellant.

4. The method of claim 1 wherein said reaction chamber is a thermal cycling chamber for amplifying nucleic acids and wherein said inducing step is performed after completion of a thermal cycling reaction.

5. The method of claim 1 wherein said reaction chamber is an elongated thermal cycling chamber for amplifying nucleic acids and wherein said inducing step comprises the application of heat to said propellant.

6. The method of claim 1 wherein said propellant is a vaporizable fluid.

7. The method of claim 5 wherein said propellant is a vaporizable fluid.

8. The method of claim 1 wherein said propellant is air.

9. The method of claim 1 wherein said inducing step is effected by non-mechanical means.

10. The method of claim 4 wherein said inducing step is effected by non-mechanical means.

11. The method of claim 4 wherein said reaction chamber is an elongated chamber having at least two distinct longitudinal segments and wherein said method further comprises:

a) perforating said thermal cycling reaction by intermittently applying heat to a first longitudinal segment; and b) inducing expansion of said propellant by applying heat to a different longitudinal segment, thereby transferring said reaction sample to said detection chamber.

12. The method of claim 4 wherein said reaction chamber is an elongated chamber having a longitudinal segment and wherein said method further comprises:

a) performing said thermal cycling reaction by intermittently applying a first maximum amount of heat to said longitudinal segment, and b) inducing expansion of said propellant by applying heat in excess of said first maximum to said longitudinal segment, thereby transferring said reaction sample to said detection chamber.

13. The method of claim 4 wherein said thermal cycling reaction comprises a ligase chain reaction or a polymerase chain reaction.

14. The method of claim 5 wherein said thermal cycling reaction comprises a ligase chain reaction or a polymerase chain reaction.

15. In a method for amplifying and detecting target nucleic acid, the method including steps of reacting in a reaction chamber a plurality of primers or probes with a sample suspected of containing target nucleic acid to amplify said target nucleic acid; and transferring said sample to a detection area distinct from said reaction chamber in order to detect the presence of amplified target, the improvement comprising:

transferring said sample to the detection area by using heat to propel said sample from said reaction chamber to said detection area.

16. A method for transferring a fluid sample between a reaction chamber and a detection chamber within a device, comprising the steps of:

a) providing a device having a reaction chamber and a detection chamber connected by means for fluid communication between the reaction and detection chambers, with a reaction sample in said reaction chamber, wherein the sample is a propellant non-mechanically inducible to expand;

b) expanding the sample to thereby force the sample through the means for fluid communication into the detection chamber.

17. The method of claim 16 wherein said reaction chamber is an elongated chamber.

18. The method of claim 16 wherein said heat is applied to a localized area of said elongated reaction chamber.

19. The method of claim 17 wherein said expanding step is effected by vaporizing said propellant and wherein said vaporization is localized by the use of a nucleation site in said elongated chamber.

20. The method of claim 16 wherein said reaction chamber is a thermal cycling chamber for amplifying nucleic acids and wherein said expanding step is performed after completion of a thermal cycling reaction.

21. The method of claim 20 wherein said thermal cycling reaction comprises a ligase chain reaction or a polymerase chain reaction.

\* \* \* \* \*

UNITED STATES PATENT AND TRADEMARK OFFICE
CERTIFICATE OF CORRECTION

PATENT NO. : 6,068,978
DATED : May 30, 2000
INVENTOR(S) : Peter Zaun et al.

It is certified that error appears in the above-identified patent and that said Letters Patent is hereby corrected as shown below:

<u>Column 46,</u>
Line 24, replace "perforating" with --performing--.

Signed and Sealed this

Thirty-first Day of July, 2001

*Attest:*

NICHOLAS P. GODICI
*Attesting Officer*     *Acting Director of the United States Patent and Trademark Office*